(12) United States Patent
Ogiwara et al.

(10) Patent No.: US 11,456,425 B2
(45) Date of Patent: Sep. 27, 2022

(54) ORGANIC ELECTROLUMINESCENT ELEMENT, AND ELECTRONIC APPARATUS

(71) Applicant: IDEMITSU KOSAN CO., LTD., Chiyoda-ku (JP)

(72) Inventors: Toshinari Ogiwara, Sodegaura (JP); Kei Yoshida, Sodegaura (JP); Masatoshi Saito, Sodegaura (JP); Yuichiro Kawamura, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 961 days.

(21) Appl. No.: 16/066,004

(22) PCT Filed: Dec. 27, 2016

(86) PCT No.: PCT/JP2016/088862
§ 371 (c)(1),
(2) Date: Jun. 25, 2018

(87) PCT Pub. No.: WO2017/115788
PCT Pub. Date: Jul. 6, 2017

(65) Prior Publication Data
US 2019/0044073 A1  Feb. 7, 2019

(30) Foreign Application Priority Data
Dec. 28, 2015  (JP) .............. JP2015-257286

(51) Int. Cl.
*H01L 51/00* (2006.01)
*C07D 491/048* (2006.01)
(Continued)

(52) U.S. Cl.
CPC ...... *H01L 51/0072* (2013.01); *C07D 491/048* (2013.01); *C09K 11/06* (2013.01);
(Continued)

(58) Field of Classification Search
None
See application file for complete search history.

(56) References Cited

U.S. PATENT DOCUMENTS

| 2006/0251925 | A1  | 11/2006 | Hosokawa et al. |
| 2014/0131665 | A1* | 5/2014  | Xia ............ H01L 51/0074 257/40 |

(Continued)

FOREIGN PATENT DOCUMENTS

| JP | 2006-298793 A | 11/2006 |
| JP | 5669163 B1    | 2/2015  |

(Continued)

OTHER PUBLICATIONS

International Search Report dated Apr. 4, 2017 in PCT/JP2016/088862 filed Dec. 27, 2016.

(Continued)

*Primary Examiner* — Jay Yang
(74) *Attorney, Agent, or Firm* — Oblon, McClelland, Maier & Neustadt, L.L.P.

(57) ABSTRACT

An organic electroluminescence device includes an anode, an emitting layer, and a cathode. The emitting layer contains a delayed fluorescent first compound, a fluorescent second compound, and a third compound represented by Cz-Az. The second compound emits light with a main peak wavelength ranging from 430 nm to 540 nm. Az is a cyclic structure selected from the group consisting of a substituted or unsubstituted pyridine ring, a substituted or unsubstituted pyrimidine ring, a substituted or unsubstituted triazine ring, and a substituted or unsubstituted pyrazine ring. Cz is represented by a formula (3B) below.

(Continued)

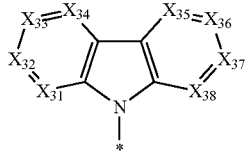

(3B)

20 Claims, 4 Drawing Sheets

(51) Int. Cl.
*C09K 11/06* (2006.01)
*H01L 51/50* (2006.01)

(52) U.S. Cl.
CPC ........ *H01L 51/008* (2013.01); *H01L 51/0067* (2013.01); *H01L 51/0071* (2013.01); *H01L 51/5012* (2013.01); *C09K 2211/1018* (2013.01); *H01L 51/5056* (2013.01); *H01L 51/5072* (2013.01); *H01L 2251/5384* (2013.01)

(56) References Cited

U.S. PATENT DOCUMENTS

2015/0333267 A1* 11/2015 Kamatani ............. C07C 13/567
257/40
2016/0190478 A1 6/2016 Nakanotani et al.
2017/0077418 A1 3/2017 Stoessel et al.

FOREIGN PATENT DOCUMENTS

| WO | WO 2008/059713 A1 | 5/2008 |
| WO | WO 2010/122810 A1 | 10/2010 |
| WO | WO 2013/024872 A1 | 2/2013 |
| WO | WO 2013/180241 A1 | 12/2013 |
| WO | WO-2014/054552 A1 * | 4/2014 |
| WO | WO 2014/092083 A1 | 6/2014 |
| WO | WO 2014/104346 A1 | 7/2014 |
| WO | WO 2015/135624 A1 | 9/2015 |

OTHER PUBLICATIONS

Chihaya Adachi, "Yuki Hando-tai no Debaisu Bussei," Device Physics of Organic Semiconductors, Apr. 1, 2012, 19 Pages (with English language translation).

Hajime Nakanotani, et al., "High-efficiency organic light-emitting diodes with fluorescent emitters," Nature Communications, vol. 5, No. 4016, 2014, 7 Pages.

Keiro Nasu, et al., "A highly luminescent spiro-anthracenone-based organic light-emitting diode exhibiting thermally activated delayed fluorescence," Chemical Communications, vol. 49, 2013, pp. 10385-10387.

Qisheng Zhang, et al., "Efficient blue organic light-emitting diodes employing thermally activated delayed fluorescence," Nature Photonics, vol. 8, No. 4, Apr. 2014, 9 Pages.

Hiroki Uoyama, et al., "Highly efficient organic light-emitting diodes from delayed fluorescence," Nature, vol. 492, Dec. 13, 2012, 7 Pages.

* cited by examiner

ORGANIC ELECTROLUMINESCENT ELEMENT, AND ELECTRONIC APPARATUS

TECHNICAL FIELD

The present invention relates to an organic electroluminescence device and an electronic device.

BACKGROUND ART

When a voltage is applied to an organic electroluminescence device (hereinafter occasionally referred to as "organic EL device"), holes are injected into an emitting layer from an anode and electrons are injected into the emitting layer from a cathode. The holes and the electrons are recombined in the emitting layer to generate excitons. According to the electron spin statistics theory, singlet excitons and triplet excitons are generated at a ratio of 25%:75%.

A fluorescent organic EL device using luminescence from the singlet excitons, which has come into use in full-color displays for, for instance, mobile phones and televisions, is supposed to have an internal quantum efficiency of 25% at a maximum. Using triplet excitons in addition to the singlet excitons is thus expected to allow the organic EL device to emit light with improved efficiency.

Accordingly, a highly efficient fluorescent organic EL device using delayed fluorescence has been suggested and studied.

For instance, a TADF (Thermally Activated Delayed Fluorescence) mechanism has been studied. The TADF mechanism uses a phenomenon in which inverse intersystem crossing from triplet excitons to singlet excitons thermally occurs when a material having a small energy gap ($\Delta ST$) between a singlet energy level and a triplet energy level is used. As for thermally activated delayed fluorescence, refer to, for instance, "ADACHI, Chihaya, ed., *Yuki Hando-tai no Debaisu Bussei* (*Device Physics of Organic Semiconductors*), Kodansha, published on Apr. 1, 2012, pp. 261-262." Organic EL devices using the TADF mechanism are disclosed in, for instance, Patent Literature 1 and Non-patent Literature.

The organic EL device of Patent Literature 1 includes an emitting layer containing a TADF compound, luminescent material or rubrene, and a matrix material. This emitting layer emits orange light.

The organic EL device of Non-patent Literature 1 includes an emitting layer containing an assist dopant or TADF compound, a luminescent material or perylene derivative (TBPe; 2,5,8,11-tetra-tert-butylperylene), and a host material or DPEPO (bis-(2-(diphenylphosphino)phenyl)ether oxide). This emitting layer emits blue light.

CITATION LIST

Patent Literatures

Patent Literature 1: International Publication No. WO 2015/135624

Non-Patent Literature(s)

Non-patent Literature 1: Hajime Nakanotani et al, *High-efficiency organic light-emitting diodes with fluorescent emitters*, NATURE COMMUNICATIONS, 5, 4016, 2014

SUMMARY OF THE INVENTION

Problems to be Solved by the Invention

A high-performance organic electroluminescence device with an excellent luminous efficiency capable of emitting light in a wavelength range from blue to green has been demanded.

An object of the invention is to provide a high-performance organic electroluminescence device capable of emitting light in a wavelength range from blue to green. Another object of the invention is to provide an electronic device including the organic electroluminescence device.

Means for Solving the Problems

According to an aspect of the invention, an organic electroluminescence device includes: an anode; an emitting layer; and a cathode, in which the emitting layer contains: a delayed fluorescent first compound; a fluorescent second compound; and a third compound represented by a formula (3A) below, and the second compound emits light with a main peak wavelength ranging from 430 nm to 540 nm.

$$Cz\text{-}Az \quad (3A)$$

In the formula (3A):

Az is a cyclic structure selected from the group consisting of a substituted or unsubstituted pyridine ring, a substituted or unsubstituted pyrimidine ring, a substituted or unsubstituted triazine ring, and a substituted or unsubstituted pyrazine ring; and Cz is represented by a formula (3B) below.

[Chemical Formula 1]

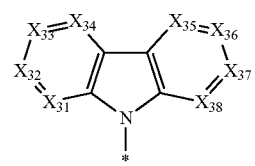

(3B)

In the formula (3B):

$X_{31}$ to $X_{38}$ are each independently a nitrogen atom or C-Rx;

Rx are each independently a hydrogen atom or a substituent, Rx as a substituent being a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group;

plural Rx are mutually the same or different;

when two or more of $X_{31}$ to $X_{38}$ are each C-Rx and Rx is a substituent, Rx are bonded together to form a ring or form no ring; and

* represents a bonding site to a carbon atom in the cyclic structure represented by Az.

According to another aspect of the invention, an electronic device includes the organic EL device.

According to the above aspects of the invention, a high-performance organic electroluminescence device capable of emitting light in a wavelength range from blue to green, and an electronic device including the organic electroluminescence device can be provided.

DESCRIPTION OF EMBODIMENTS

First Exemplary Embodiment

Arrangement of Organic EL Device

An organic EL device according to a first exemplary embodiment includes a pair of electrodes, and an organic layer provided between the pair of electrodes. The organic layer includes at least one layer containing an organic compound. Alternatively, the organic layer is provided by layering a plurality of layers each containing an organic compound. The organic layer may further contain an inorganic compound. In the organic EL device of the first exemplary embodiment, at least one layer forming the organic layer is an emitting layer. Accordingly, the organic layer may consist of a single emitting layer or, alternatively, may further include layers usable in organic EL devices, such as a hole injecting layer, a hole transporting layer, an electron injecting layer, an electron transporting layer, and a blocking layer.

The organic EL device may have the following typical arrangements (a) to (f).

(a) anode/emitting layer/cathode
(b) anode/hole injecting-transporting layer/emitting layer/cathode
(c) anode/emitting layer/electron injecting-transporting layer/cathode
(d) anode/hole injecting-transporting layer/emitting layer/electron injecting-transporting layer/cathode
(e) anode/hole injecting-transporting layer/emitting layer/blocking layer/electron injecting-transporting layer/cathode
(f) anode/hole injecting-transporting layer/blocking layer/emitting layer/blocking layer/electron injecting-transporting layer/cathode Among the above, the arrangement (d) is preferably usable. However, the invention is not limited to these arrangements. It should be noted that the term "emitting layer" means an organic layer with a luminescent function. The term "hole injecting/transporting layer" means "at least one of a hole injecting layer and a hole transporting layer." The term "electron injecting/transporting layer" means "at least one of an electron injecting layer and an electron transporting layer." When the organic EL device includes a hole injecting layer and a hole transporting layer, the hole injecting layer is preferably provided between the hole transporting layer and the anode. When the organic EL device includes an electron injecting layer and an electron transporting layer, the electron injecting layer is preferably provided between the electron transporting layer and the cathode. Each of the hole injecting layer, the hole transporting layer, the electron transporting layer and the electron injecting layer may be in the form of a single layer or in the form of a plurality of layers.

Figure 1:
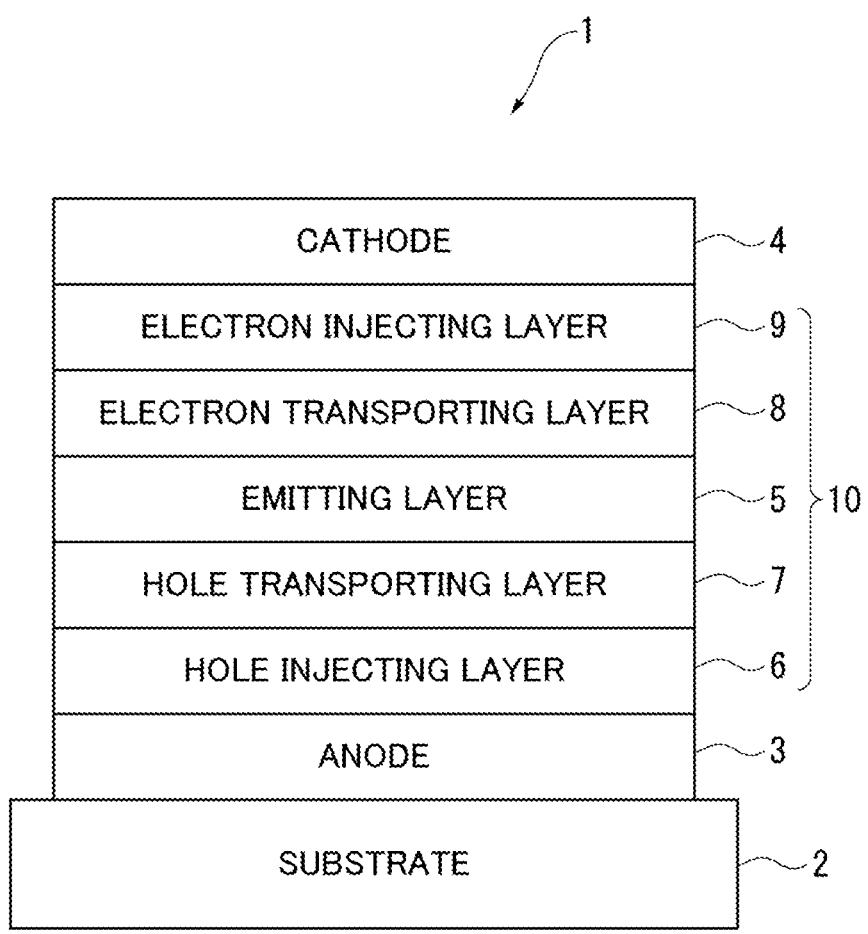
FIG. 1 schematically shows an exemplary arrangement of an organic electroluminescence device according to an exemplary embodiment of the invention.

FIG. 1 schematically shows an exemplary arrangement of the organic EL device according to the first exemplary embodiment.

An organic EL device 1 includes a translucent substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8 and an electron injecting layer 9, which are layered on one another in this sequence from the anode 3.

Emitting Layer

The emitting layer 5 of the organic EL device 1 contains a first compound, a second compound, and a third compound. The emitting layer 5 may contain a metal complex. The emitting layer 5 preferably contains no phosphorescent metal complex.

Further, the first compound and the third compound are each preferably a host material (occasionally referred to as a matrix material) and the second compound is preferably a dopant material (occasionally referred to as a guest material, emitter or luminescent material).

First Compound

The first compound is a delayed fluorescent compound.

The first compound is also preferably represented by a formula (1) below.

[Chemical Formula 2]

In the formula (1):

A is a group with a moiety selected from formulae (a-1) to (a-7) below, plural A being mutually the same or different and being bonded together to form a saturated or unsaturated ring or forming no ring;

B is a group with a moiety selected from formulae (b-1) to (b-6) below, plural B being mutually the same or different and being bonded together to form a saturated or unsaturated ring or forming no ring;

a, b and d are each independently an integer of 1 to 5;

c is an integer of 0 to 5;

when c is 0, A and B are single-bonded or spiro-bonded to each other; and when c is an integer of 1 to 5, L is a linking group selected from the group consisting of a substituted or unsubstituted aromatic hydrocarbon group having 6 to 30 ring carbon atoms and a substituted or unsubstituted heterocyclic group having 5 to 30 ring atoms, plural L being mutually the same or different and being bonded together to form a saturated or unsaturated ring or forming no ring.

[Chemical Formula 3]

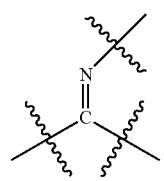

(a-1)

-continued (a-2) 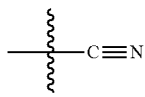

(a-3) 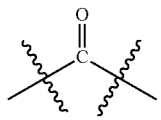

(a-4) 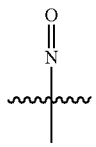

(a-5) 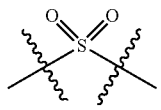

(a-6) 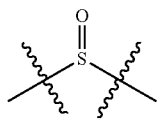

(a-7) 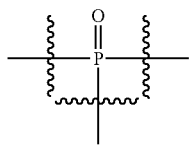

[Chemical Formula 4]

(b-1) 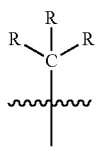

(b-2) 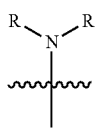

(b-3) 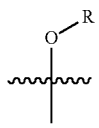

(b-4) 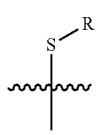

(b-5) 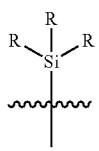

(b-6) 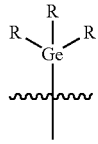

In the formulae (b-1) to (b-6), R are each independently a hydrogen atom or a substituent, R as a substituent being selected from the group consisting of a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 20 carbon atoms, plural R being mutually the same or different and being bonded together to form a saturated or unsaturated ring or forming no ring.

With regard to the group with the moiety selected from the formulae (a-1) to (a-7), for instance, the group with the moiety of the formula (a-3) may be a group represented by a formula (a-3-1) below.

[Chemical Formula 5]

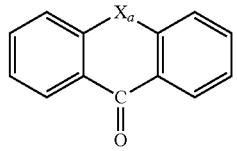

(a-3-1)

In the formula (a-3-1), Xa is a single bond, an oxygen atom, a sulfur atom, or a carbon atom bonded to L or B in the formula (1).

With regard to the group with the moiety selected from the formulae (b-1) to (b-6), for instance, the group with the moiety of the formula (b-2) may be a group represented by a formula (b-2-1) below.

[Chemical Formula 6]

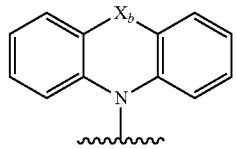

(b-2-1)

In the formula (b-2-1), Xb is a single bond, an oxygen atom, a sulfur atom, $CR_{b1}R_{b2}$, or a carbon atom bonded to L or A in the formula (1).

$R_{b1}$ and $R_{b2}$ are each independently a hydrogen atom or a substituent, $R_{b1}$ and $R_{b2}$ as substituents being each independently selected from the group consisting of a substituted or unsubstituted alkyl group having 1 to 30 carbon atoms and a substituted or unsubstituted aromatic hydrocarbon group having 6 to 30 ring carbon atoms.

$R_{b1}$ and $R_{b2}$ are each preferably a substituent selected from the group consisting of a substituted or unsubstituted alkyl group having 1 to 30 carbon atoms and a substituted or unsubstituted aromatic hydrocarbon group having 6 to 30 ring carbon atoms, more preferably a substituent selected from the group consisting of a substituted or unsubstituted alkyl group having 1 to 30 carbon atoms.

A bonding pattern of the compound represented by the formula (1) is exemplified by bonding patterns shown in Table 1 below.

TABLE 1

| No. | a | b | c | d | Bonding Pattern |
|-----|---|---|---|---|-----------------|
| (1A) | 1 | 1 | 0 | 1 | B—A |
| (1B) | 1 | 1 | 1 | 1 | B—L—A |
| (1C) | 2 | 1 | 0 | 1 | B—A—A, <br> B<A\A |
| (1D) | 1 | 2 | 0 | 1 | B—B—A, <br> B\A\B |
| (1E) | 2 | 1 | 1 | 1 | B—L—A—A, <br> B—L<A\A |
| (1F) | 1 | 2 | 1 | 1 | B—B—L—A, <br> B\L—A\B |
| (1G) | 1 | 1 | 2 | 1 | B—L—L—A |
| (1H) | 1 | 1 | 1 | 2 | B—L\A\B—L, <br> B—L—B—L—A |

In the first exemplary embodiment, B in the formula (1) is preferably represented by a formula (100) below.

[Chemical Formula 7]

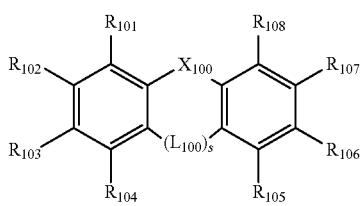

(100)

In the formula (100):

$R_{101}$ to $R_{108}$ are each independently a hydrogen atom or a substituent, $R_{101}$ to $R_{108}$ as substituents being each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted silyl group, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, and a substituted or unsubstituted arylthio group having 6 to 30 ring carbon atoms, such that any one of a pair of $R_{101}$ and $R_{102}$, a pair of $R_{102}$ and $R_{103}$, a pair of $R_{103}$ and $R_{104}$, a pair of $R_{105}$ and $R_{106}$, a pair of $R_{106}$ and $R_{107}$ and a pair of $R_{107}$ and $R_{108}$ forms a saturated or unsaturated cyclic structure or forms no cyclic structure;

$L_{100}$ is a linking group selected from formulae (111) to (117) below;

s is an integer of 1 to 3, plural $L_{100}$ being mutually the same or different when s is 2 or 3; and $X_{100}$ is a linking group selected from formulae (121) to (125) below.

[Chemical Formula 8]

(111)

(112)

(113)

(114)

(115)

(116)

(117)

In the formulae (113) to (117), $R_{109}$ each independently mean the same as $R_{101}$ to $R_{108}$ in the formula (100).

It should be noted that one of $R_{101}$ to $R_{108}$ or one of $R_{109}$ in the formula (100) is a single bond to L or A in the formula (1).

$R_{109}$ and $R_{104}$ or $R_{105}$ in the formula (100) are bonded to each other to form a saturated or unsaturated cyclic structure or form no ring.

Plural $R_{109}$ are mutually the same or different.

[Chemical Formula 9]

(121)

(122)

(123)

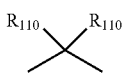

(124)

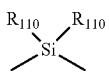

(125)

In the formulae (123) to (125):

$R_{110}$ are each independently a hydrogen atom or a substituent, $R_{110}$ as a substituent being selected from the group consisting of a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 30 carbon atoms, plural $R_{110}$ being mutually the same or different; and $R_{110}$ and $R_{101}$ or $R_{108}$ in the formula (100) are bonded to each other to form a saturated or unsaturated cyclic structure or form no ring.

In the first exemplary embodiment, $L_{100}$ is preferably represented by any one of the formulae (111) to (114), more preferably represented by the formula (113) or (114).

In the first exemplary embodiment, $X_{100}$ is preferably represented by any one of the formulae (121) to (124), more preferably represented by the formula (123) or (124).

An example of the compound represented by the formula (1) is a compound represented by a formula (10) below.

[Chemical Formula 10]

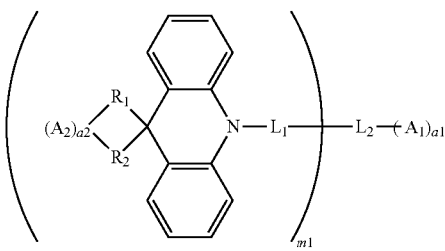

(10)

In the formula (10):
a1 is 0 or 1;
a2 is 0 or 1;
a1+a2≥1;
m1 is an integer of 1 to 5;
when a2 is 0, $R_1$ and $R_2$ are each independently a hydrogen atom or a monovalent substituent, $R_1$ and $R_2$ as substituents being each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group;

when a2 is 1, $R_1$ and $R_2$ are each independently a linking group selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group;

when m1 is 2 or more, plural $R_1$ are mutually the same or different and plural $R_2$ are mutually the same or different;

$A_1$ and $A_2$ are each independently a group with a moiety selected from the formulae (a-1) to (a-7), plural $A_2$ being mutually the same or different when m1 is 2 or more;

when a1 is 0, $L_2$ is a hydrogen atom or a monovalent substituent, $L_2$ as a monovalent substituent being selected from the group consisting of a substituted or unsubstituted aromatic hydrocarbon group having 6 to 30 ring carbon atoms, and a substituted or unsubstituted heterocyclic group having 5 to 30 ring atoms;

when a1 is 1, $L_2$ is a single bond or a linking group, $L_2$ as a linking group being selected from the group consisting of a substituted or unsubstituted aromatic hydrocarbon group having 6 to 30 ring carbon atoms, and a substituted or unsubstituted heterocyclic group having 5 to 30 ring atoms; and $L_1$ is a single bond or a linking group, $L_1$ as a linking group being selected from the group consisting of a substituted or unsubstituted aromatic hydrocarbon group having 6 to 30 ring carbon atoms, and a substituted or unsubstituted heterocyclic group having 5 to 30 ring atoms, plural $L_1$ being mutually the same or different when m1 is 2 or more.

In the first exemplary embodiment, when a2 is 0, $R_1$ and $R_2$ are each preferably a substituent selected from the group consisting of a substituted or unsubstituted aromatic hydrocarbon group having 6 to 30 ring carbon atoms, a substituted or unsubstituted heterocyclic group having 5 to 30 ring atoms, and a substituted silyl group, more preferably a substituent selected from the group consisting of a substituted or unsubstituted aromatic hydrocarbon group having 6 to 30 ring carbon atoms, and a substituted or unsubstituted heterocyclic group having 5 to 30 ring atoms.

In the first exemplary embodiment, when a2 is 1, $R_1$ and $R_2$ are each preferably a linking group selected from the group consisting of a substituted or unsubstituted aromatic hydrocarbon group having 6 to 30 ring carbon atoms, a substituted or unsubstituted heterocyclic group having 5 to 30 ring atoms, and a substituted silyl group, more preferably a linking group selected from the group consisting of a substituted or unsubstituted aromatic hydrocarbon group having 6 to 30 ring carbon atoms, and a substituted or unsubstituted heterocyclic group having 5 to 30 ring atoms.

An example of the compound represented by the formula (1) is a compound represented by a formula (10') below.

[Chemical Formula 11]

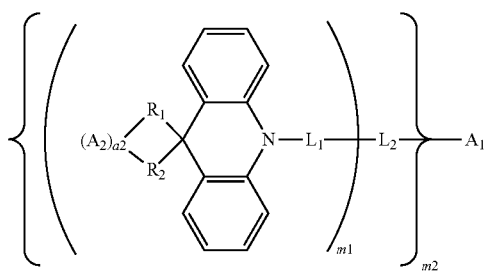

(10')

In the formula (10'):
m2 is 2;
a2 is 0 or 1, plural a2 being mutually the same or different;
m1 is an integer of 1 to 5, plural m1 being mutually the same or different;
when a2 is 0, $R_1$ and $R_2$ are each independently a hydrogen atom or a monovalent substituent, $R_1$ and $R_2$ as substituents being each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group;
when a2 is 1, $R_1$ and $R_2$ are each independently a linking group selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkoxy group having 1 to 30 carbon atoms, a substituted or unsubstituted aralkyl group having 7 to 30 carbon atoms, a substituted or unsubstituted aryloxy group having 6 to 30 ring carbon atoms, and a substituted silyl group;
plural $R_1$ are mutually the same or different and plural $R_2$ are mutually the same or different;
$A_1$ and $A_2$ are each independently a group with a moiety selected from the formulae (a-1) to (a-7), plural $A_2$ being mutually the same or different;
$L_2$ is a single bond or a linking group, $L_2$ as a linking group being selected from the group consisting of a substituted or unsubstituted aromatic hydrocarbon group having 6 to 30 ring carbon atoms, and a substituted or unsubstituted heterocyclic group having 5 to 30 ring atoms, plural $L_2$ being mutually the same or different; and
$L_1$ is a single bond or a linking group, $L_1$ as a linking group being selected from the group consisting of a substituted or unsubstituted aromatic hydrocarbon group having 6 to 30 ring carbon atoms, and a substituted or unsubstituted heterocyclic group having 5 to 30 ring atoms, plural $L_1$ being mutually the same or different.
An example of the compound represented by the formula (10) is a compound represented by a formula (10A) below.

[Chemical Formula 12]

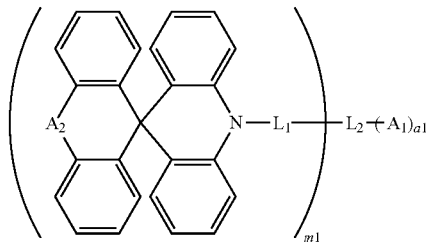

(10A)

In the formula (10A), a1, m1, $A_1$, $A_2$, $L_1$ and $L_2$ respectively mean the same as a1, m1, $A_1$, $A_2$, $L_1$ and $L_2$ in the formula (10).

Examples of the compounds represented by the formula (10) and the formula (10') are compounds represented by formulae (10B) to (10E) below.

[Chemical Formula 13]

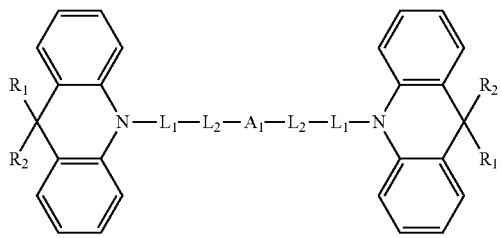

(10B)

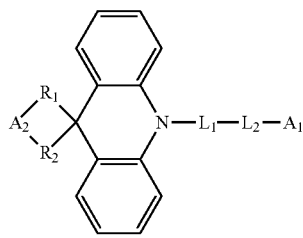

(10C)

[Chemical Formula 14]

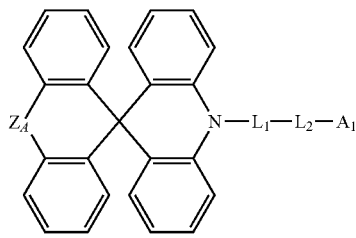

(10D)

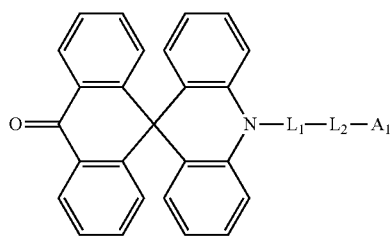

(10E)

In the formula (10D), $Z_A$ is selected from the group consisting of =N-$L_1$-$L_2$-$A_1$, oxygen atom, sulfur atom and selenium atom. In the formulae (10B), (10C), (10D) and (10E), $R_1$, $R_2$, $A_1$, $A_2$, $L_1$ and $L_2$ respectively mean the same as $R_1$, $R_2$, $A_1$, $A_2$, $L_1$ and $L_2$ in the formula (10).

The first compound is also preferably represented by a formula (110) below.

[Chemical Formula 15]

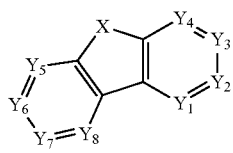
(110)

In the formula (110):

X is an oxygen atom, a sulfur atom or a selenium atom;

$Y_1$ to $Y_8$ are each independently $CR_{1a}$ (a carbon atom bonded to $R_{1a}$), $CR_{1b}$ (a carbon atom bonded to $R_{1b}$) or a nitrogen atom;

at least two of $Y_1$ to $Y_8$ are each an nitrogen atom and at least one of $Y_1$ to $Y_8$ is $CR_{1a}$;

$R_{1a}$ are each independently one selected from the group consisting of groups represented by formulae (A) to (L) below, plural $R_{1a}$ being mutually the same or different;

$R_{1b}$ are each independently a hydrogen atom or a substituent;

$R_{1b}$ as a substituent are each independently selected from the group consisting of a halogen atom, a substituted or unsubstituted alkyl group having 1 to 30 carbon atoms, a substituted or unsubstituted cycloalkyl group having 3 to 30 ring carbon atoms, a substituted or unsubstituted aralkyl group having 5 to 30 carbon atoms, a substituted or unsubstituted alkoxy group having 1 to 30 carbon atoms, a substituted or unsubstituted arylalkoxy group having 5 to 30 carbon atoms, a substituted or unsubstituted amino group, a substituted or unsubstituted silyl group, a substituted or unsubstituted alkenyl group having 2 to 30 carbon atoms, a substituted or unsubstituted cycloalkenyl group having 3 to 30 carbon atoms, a substituted or unsubstituted alkynyl group having 2 to 30 carbon atoms, a substituted or unsubstituted cycloalkynyl group having 3 to 30 carbon atoms, a substituted or unsubstituted aromatic hydrocarbon group having 6 to 30 ring carbon atoms, a substituted or unsubstituted heterocyclic group having 5 to 30 ring atoms, a substituted or unsubstituted carbonyl group, a substituted or unsubstituted alkoxycarbonyl group, a substituted or unsubstituted carboxy group, a cyano group; a substituted or unsubstituted sulfanyl group, a substituted sulfinyl group, a substituted sulfonyl group, and a substituted or unsubstituted phosphoryl group; and plural $R_{1b}$ as substituents are mutually the same or different.

[Chemical Formula 16]

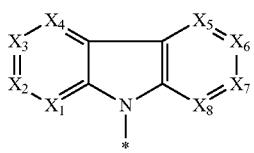
(A)

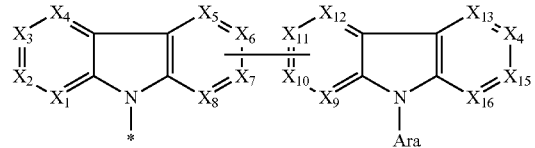
(B)

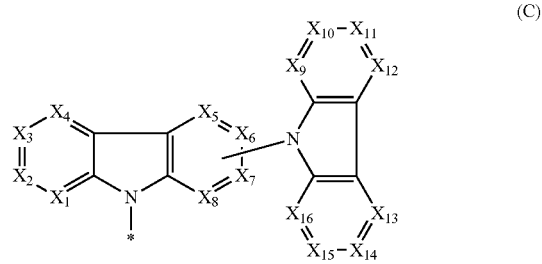
(C)

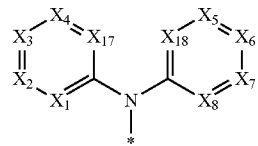
(D)

[Chemical Formula 17]

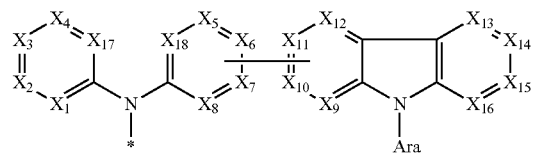
(E)

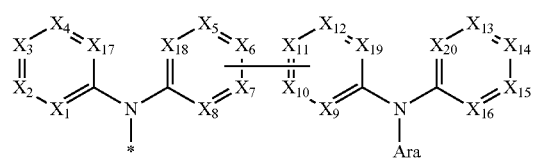
(F)

[Chemical Formula 18]

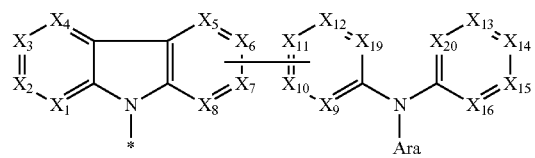
(G)

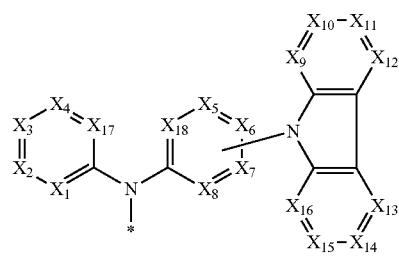
(H)

-continued

[Chemical Formula 19]

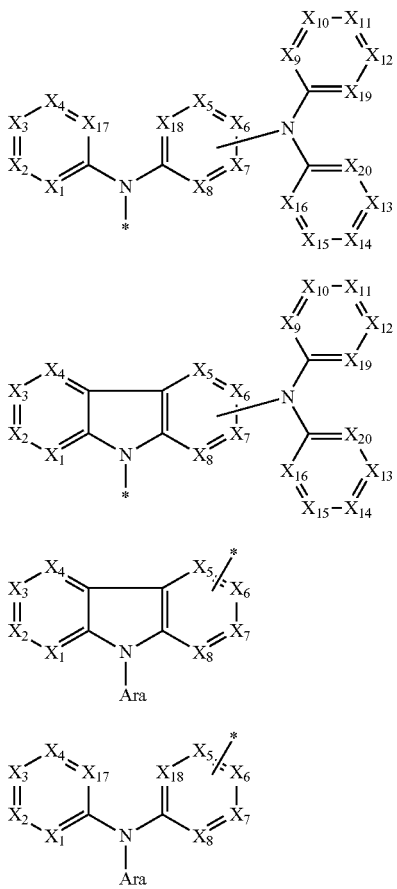

In the formulae (A) to (L):

$X_1$ to $X_{20}$ are each independently a nitrogen atom or CRz (a carbon atom bonded to Rz);

in the formula (B), one of $X_5$ to $X_8$ is a carbon atom bonded to one of $X_9$ to $X_{12}$ and one of $X_9$ to $X_{12}$ is a carbon atom bonded to one of $X_5$ to $X_8$;

in the formula (C), one of $X_5$ to $X_8$ is a carbon atom bonded to a nitrogen atom in a five-membered ring of a fused ring having $X_9$ to $X_{12}$ and $X_{13}$ to $X_{16}$;

in the formula (E), one of $X_5$ to $X_8$ and $X_{18}$ is a carbon atom bonded to one of $X_9$ to $X_{12}$ and one of $X_9$ to $X_{12}$ is a carbon atom bonded to one of $X_5$ to $X_8$ and $X_{18}$;

in the formula (F), one of $X_5$ to $X_8$ and $X_{18}$ is a carbon atom bonded to one of $X_9$ to $X_{12}$ and $X_{19}$ and one of $X_9$ to $X_{12}$ and $X_{19}$ is a carbon atom bonded to one of $X_5$ to $X_8$ and $X_{18}$;

in the formula (G), one of $X_5$ to $X_8$ is a carbon atom bonded to one of $X_9$ to $X_{12}$ and $X_{19}$ and one of $X_9$ to $X_{12}$ and $X_{19}$ is a carbon atom bonded to one of $X_5$ to $X_8$;

in the formula (H), one of $X_5$ to $X_8$ and $X_{18}$ is a carbon atom bonded to a nitrogen atom in a five-membered ring of a fused ring having $X_9$ to $X_{12}$ and $X_{13}$ to $X_{16}$;

in the formula (I), one of $X_5$ to $X_8$ and $X_{18}$ is a carbon atom bonded to a nitrogen atom that links a ring having $X_9$ to $X_{12}$ and $X_{19}$ and a ring having $X_{13}$ to $X_{16}$ and $X_{20}$;

in the formula (J), one of $X_5$ to $X_8$ is a carbon atom bonded to a nitrogen atom that links a ring having $X_9$ to $X_{12}$ and $X_{19}$ and a ring having $X_{13}$ to $X_{16}$ and $X_{20}$;

in the formula (K), one of $X_5$ to $X_8$ is a carbon atom bonded to one of $Y_1$ to $Y_8$;

in the formula (L), one of $X_5$ to $X_8$ and $X_{18}$ is a carbon atom bonded to one of $Y_1$ to $Y_8$;

Rz are each independently a hydrogen atom or a substituent;

Rz as a substituent are each independently selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted phosphoryl group, a substituted or unsubstituted silyl group, a cyano group, a nitro group, and a substituted or unsubstituted carboxy group; and plural Rz as substituents are mutually the same or different, plural Rz as substituents being directly bonded together to form a ring or forming no ring, or forming a ring via a hetero atom or forming no ring;

Ara is selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted phosphoryl group, and a substituted or unsubstituted silyl group; and

* represents a bonding site for bonding to one of $Y_1$ to $Y_8$.

In the first exemplary embodiment, $X_1$ to $X_{20}$ are each preferably CRz.

In the first exemplary embodiment, plural Rz are preferably directly bonded together to form a saturated or unsaturated ring. The ring formed by bonding Rz together may be a fused ring or a non-fused ring.

In the first exemplary embodiment, Rz also preferably form no ring.

The first compound is also preferably represented by a formula (150) below.

[Chemical Formula 20]

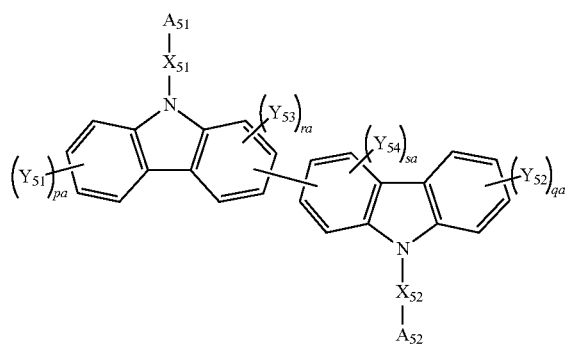

(150)

In the formula (150):

$A_{51}$ is a substituted or unsubstituted nitrogen-containing heterocyclic group having 1 to 30 ring carbon atoms;

$A_{52}$ is a substituted or unsubstituted aromatic hydrocarbon group having 6 to 30 ring carbon atoms or a substituted or unsubstituted nitrogen-containing heterocyclic group having 1 to 30 ring carbon atoms;

$X_{51}$ and $X_{52}$ are each independently a single bond or a linking group, $X_{51}$ and $X_{52}$ as a linking group being each independently selected from the group consisting of a substituted or unsubstituted aromatic hydrocarbon group having 6 to 30 ring carbon atoms, a substituted or unsubstituted fused aromatic hydrocarbon group having 10 to 30 ring carbon atoms, a substituted or unsubstituted aromatic hydrocarbon group having 2 to 30 ring carbon atoms, and a substituted or unsubstituted fused aromatic heterocyclic group having 2 to 30 ring carbon atoms;

$Y_{51}$ to $Y_{54}$ are each independently a hydrogen atom or a substituent, $Y_{51}$ to $Y_{54}$ as substituents being each independently selected from the group consisting of a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, and a substituted or unsubstituted heterocyclic group having 5 to 30 ring atoms;

pa is an integer of 1 to 4, qa is an integer of 1 to 4, ra is an integer of 1 to 3, and sa is an integer of 1 to 3;

plural $Y_{51}$ are mutually the same or different and are bonded together to form a cyclic structure or form no cyclic structure;

plural $Y_{52}$ are mutually the same or different and are bonded together to form a cyclic structure or form no cyclic structure;

plural $Y_{53}$ are mutually the same or different and are bonded together to form a cyclic structure or form no cyclic structure; and plural $Y_{54}$ are mutually the same or different and are bonded together to form a cyclic structure or form no cyclic structure;

The first compound represented by the formula (150) is also preferably represented by a formula (151) below.

[Chemical Formula 21]

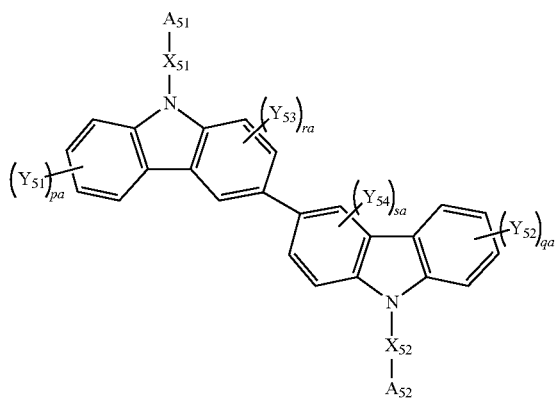

(151)

In the formula (151), $A_{51}$, $A_{52}$, $X_{51}$, $X_{52}$, $Y_{51}$ to $Y_{54}$, pa, qa, ra and sa mean the same as $A_{51}$, $A_{52}$, $X_{51}$, $X_{52}$, $Y_{51}$ to $Y_{54}$, pa, qa, ra and sa in the formula (150).

$A_{51}$ is preferably selected from the group consisting of a substituted or unsubstituted pyridine ring, a substituted or unsubstituted pyrimidine ring and a substituted or unsubstituted triazine ring, more preferably selected from the group consisting of a substituted or unsubstituted pyrimidine ring and a substituted or unsubstituted triazine ring.

$A_{51}$ is also preferably a substituted or unsubstituted pyrimidine ring.

$A_{51}$ is also preferably a substituted or unsubstituted triazine ring.

The first compound represented by the formula (150) is also preferably represented by a formula (152) below.

[Chemical Formula 22]

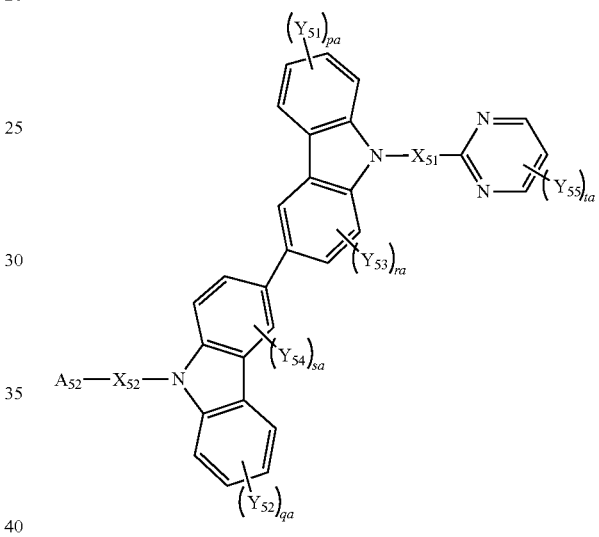

(152)

In the formula (152):

$A_{52}$, $X_{51}$, $X_{52}$, $Y_{51}$ to $Y_{54}$, pa, qa, ra and sa respectively mean the same as $A_{52}$, $X_{51}$, $X_{52}$, $Y_{51}$ to $Y_{54}$, pa, qa, ra and sa in the formula (151);

$Y_{55}$ means the same as $Y_{51}$ to $Y_{54}$ in the formula (150); and ta is an integer of 1 to 3, plural $Y_{55}$ being mutually the same of different.

Delayed Fluorescence

Delayed fluorescence (thermally activated delayed fluorescence) is explained in "*Yuki Hando-tai no Debaisu Bussei (Device Physics of Organic Semiconductors)*" (ADACHI, Chihaya, ed., published by Kodansha), pp. 261-268. According to this literature, reducing an energy gap $\Delta E_{13}$ between the singlet state and the triplet state of a luminescent material highly efficiently enables a reverse energy transfer from the triplet state to the singlet state, which usually occurs with a low transition probability, thus achieving thermally activated delayed fluorescence (thermally activated delayed fluorescence, TADF). Further, FIG. 10.38 in this literature illustrates a mechanism for occurrence of delayed fluorescence. The first compound according to the first exemplary embodiment is a compound allowing for thermally activated delayed fluorescence based on this mechanism.

Emission of delayed fluorescence can be determined by transient PL (Photo Luminescence) measurement.

A behavior of delayed fluorescence can be analyzed with reference to a decay curve obtained by the transient PL measurement. According to the transient PL measurement, a sample is irradiated with a pulsed laser to be excited and an attenuation behavior (transient property) of PL emission appearing after the irradiation is stopped is measured. The PL emission of a TADF material is divided into a luminescence component from singlet excitons generated by the first PL excitation and a luminescence component from singlet excitons generated through transition to triplet excitons. The singlet excitons generated by the first PL excitation has a considerably short lifetime in a nanosecond order. Luminescence from the singlet excitons thus decays immediately after the irradiation with the pulsed laser.

In contrast, delayed fluorescence, which is luminescence from the singlet excitons generated through transition to long-life triplet excitons, gradually decays. In other words, the luminescence from the singlet excitons generated by the first PL excitation is considerably different in time from the luminescence from the singlet excitons generated through transition to the triplet excitons. A luminous intensity attributed to delayed fluorescence can thus be calculated.

Figure 2:
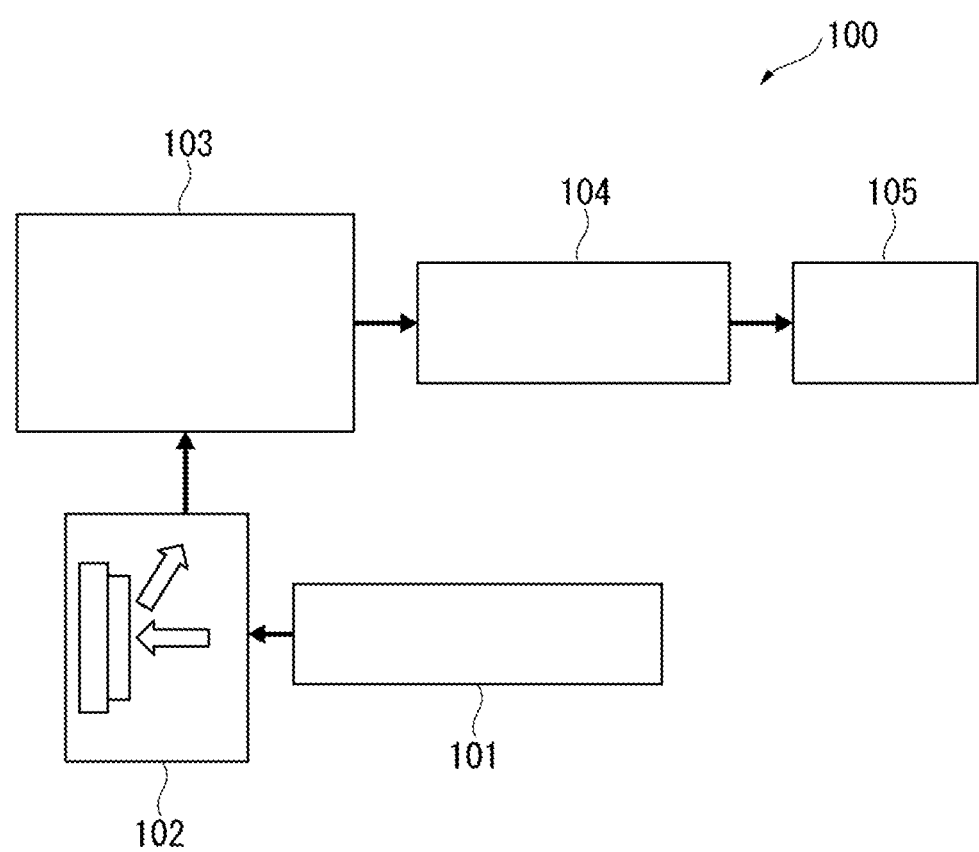
FIG. 2 schematically shows a device for measuring transient PL.

FIG. 2 schematically shows an exemplary device for the transient PL measurement.

A transient PL measuring device 100 according to the first exemplary embodiment includes a pulse laser unit 101 configured to radiate light with a predetermined wavelength, a sample chamber 102 configured to house a measurement sample, a spectrometer 103 configured to disperse light emitted from the measurement sample, a streak camera 104 configured to form a two-dimensional image 2, and a personal computer 105 configured to import and analyze the two-dimensional image. It should be noted that the transient PL measurement may be performed by a device different from the device according to the first exemplary embodiment.

The sample being housed in the sample chamber 102 is obtained by forming a thin film on a quartz substrate, the thin film being made of a matrix material doped with a doping material at a concentration of 12 mass %.

The thus-obtained thin film sample in the sample chamber 102 is irradiated with a pulsed laser from the pulse laser unit 101 to excite the doping material. Luminescence is sampled in a 90-degree direction relative to a radiation direction of the excitation light. The sampled luminescence is dispersed by the spectrometer 103 and turned into a two-dimensional image through the streak camera 104. The above process can provide a two-dimensional image in which an ordinate axis represents time, an abscissa axis represents wavelength, and a bright spot represents luminous intensity. When the thus-obtained two-dimensional image is taken out at a predetermined time axis, a luminescence spectrum in which an ordinate axis represents luminous intensity and an abscissa axis represents wavelength can be obtained. Moreover, when the two-dimensional image is taken out at a wavelength axis, a decay curve (transient PL) in which an ordinate axis represents a logarithm of luminous intensity and an abscissa axis represents time can be obtained.

For instance, the transient PL measurement was performed on a thin film sample A prepared as described above using a reference compound H1 below as the matrix material and a reference compound D1 below as the doping material.

[Chemical Formula 23]

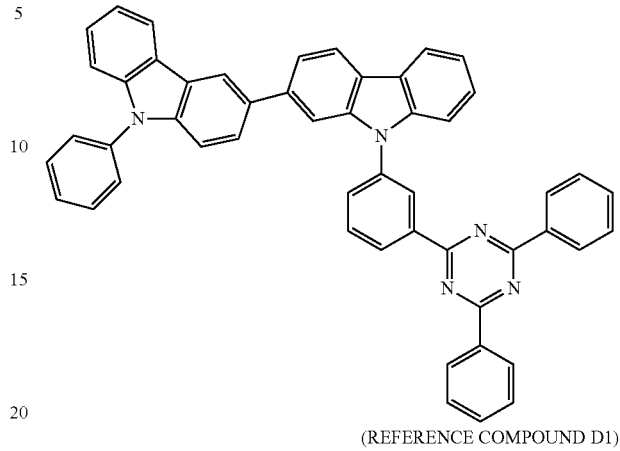

(REFERENCE COMPOUND H1)

(REFERENCE COMPOUND D1)

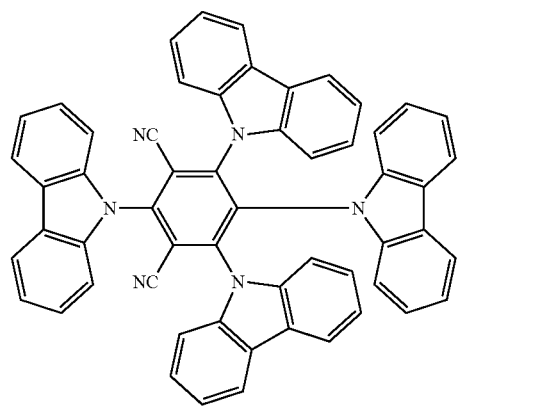

Decay curves obtained using the thin film sample A and a thin film sample B were analyzed. The thin film sample B was prepared in the same manner as described above using a reference compound H2 below as the matrix material and the reference compound D1 as the doping material.

Figure 3:
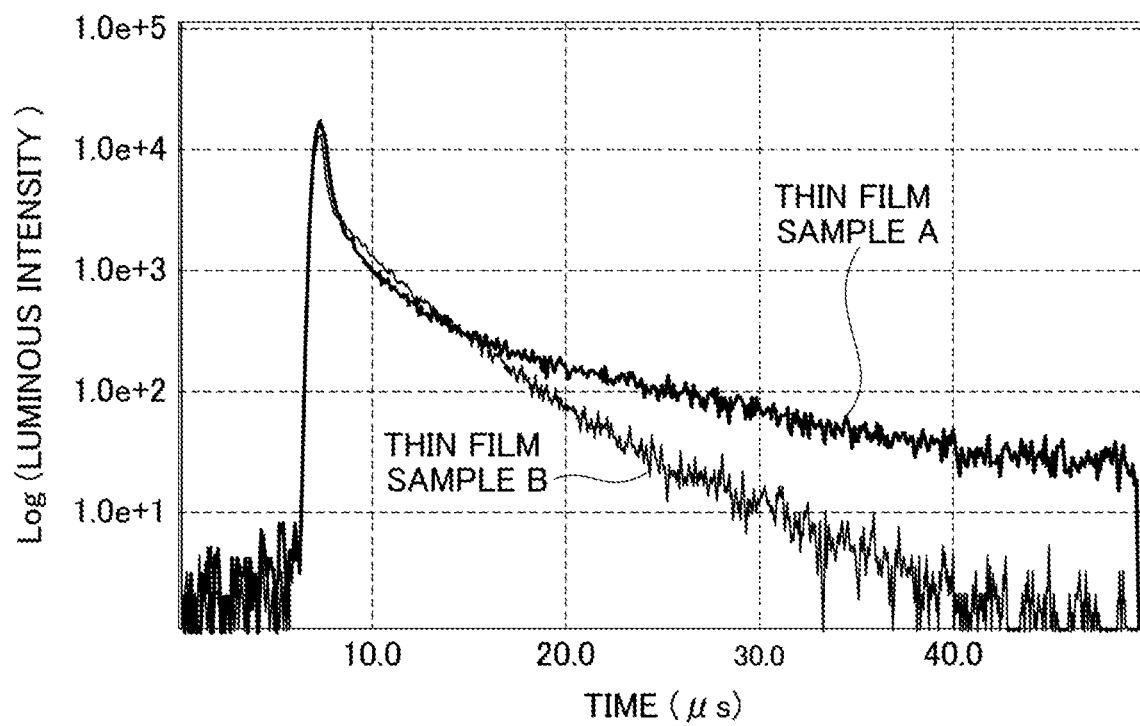
FIG. 3 shows an example of a decay curve of the transient PL.

FIG. 3 shows the decay curve resulting from the transient PL measurement of each of the thin film sample A and the thin film sample B.

[Chemical Formula 24]

(REFERENCE COMPOUND H2)

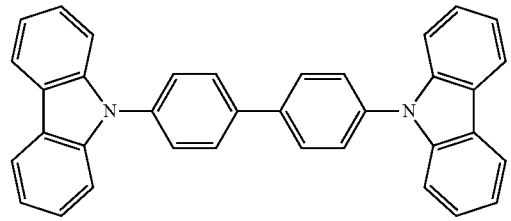

As described above, the transient PL measurement can determine a luminescence decay curve in which an ordinate axis represents luminous intensity and an abscissa axis represents time. With reference to the luminescence decay curve, a fluorescence intensity ratio between fluorescence emitted from a singlet state generated by light excitation and delayed fluorescence emitted from a singlet state generated via a triplet state by reverse energy transfer can be estimated. In a delayed fluorescence material, a ratio of the intensity of the slowly decaying delayed fluorescence to the intensity of the promptly decaying fluorescence is relatively large.

In the first exemplary embodiment, an amount of the delayed fluorescence can be determined by the device shown in FIG. 2. The first compound allows for Prompt emission, which is observed immediately when the excited state is achieved by exciting the first compound with pulsed light (i.e., light emitted from the pulse laser unit) having a wavelength absorbable into the first compound, and Delay emission, which is observed not immediately upon the excitation but after a while. In the first exemplary embodiment, the amount of Delay emission is preferably 5% or more with respect to the amount of Prompt emission. Specifically, when the amount of Prompt emission is denoted by $X_P$ and the amount of Delay emission is denoted by $X_D$, a value of $X_D/X_P$ is preferably 0.05 or more.

The respective amounts of Prompt emission and Delay emission can be determined by the same method as described in "Nature 492, 234-238, 2012." It should be noted that the respective amounts of Prompt emission and Delay emission may be calculated by a device different from the device referred to in the above literature.

A sample for measuring delayed fluorescence may be prepared by co-depositing the first compound and a compound TH-2 below on a quartz substrate at a ratio of the first compound of 12 mass % to form a 100-nm-thick thin film.

[Chemical Formula 25]

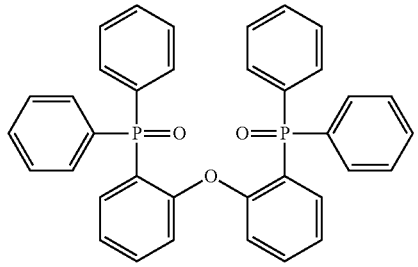

TH-2

A singlet energy $S_1(M1)$ of the first compound is preferably larger than a singlet energy $S_1(M2)$ of the second compound. In other words, the singlet energy $S_1(M1)$ of the first compound and the singlet energy $S_1(M2)$ of the second compound preferably satisfy a relationship of a numerical expression (Numerical Expression 1) below.

$S_1(M1) > S_1(M2)$ (Numerical Expression 1)

An energy gap $T_{77K}(M1)$ at 77 [K] of the first compound is preferably larger than an energy gap $T_{77K}(M2)$ at 77 [K] of the second compound.

Relationship Between Triplet Energy and Energy Gap at 77 [K]

Description will be made on a relationship between triplet energy and energy gap at 77 [K]. In the first exemplary embodiment, the energy gap at 77 [K] is different from a triplet energy as typically defined in some aspects.

The triplet energy is measured as follows. First, a sample is prepared by encapsulating in a quartz glass tube a target compound dissolved in an appropriate solvent. A phosphorescence spectrum (ordinate axis: phosphorescent luminous intensity, abscissa axis: wavelength) of the sample is measured at a low temperature (77[K]). A tangent is drawn to a rise of the phosphorescence spectrum on the short-wavelength side. The triplet energy is calculated from a wavelength value at an intersection between the tangent and the abscissa axis using a predetermined conversion equation.

The delayed fluorescent compound used in the first exemplary embodiment is preferably a compound with a small $\Delta ST$. At a small $\Delta ST$, intersystem crossing and inverse intersystem crossing are likely to occur even at a low temperature (77[K]), allowing a singlet state and a triplet state to coexist. The spectrum being measured in the same manner as described above thus contains luminescence from the singlet state and luminescence from the triplet state, which are unlikely to be distinguished from each other. However, a value of the triplet energy is supposed to be basically dominant.

Accordingly, in the first exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. A measurement sample is prepared by putting in a quartz cell a target compound dissolved in EPA (diethylether:isopentane:ethanol=5:5:2 in volume ratio) such that the concentration reaches 10 μmol/L. A phosphorescence spectrum (ordinate axis: phosphorescent luminous intensity, abscissa axis: wavelength) of the measurement sample is measured at a low temperature (77[K]). A tangent is drawn to a rise of the phosphorescence spectrum on the short-wavelength side. An energy amount calculated from a wavelength value $\lambda_{edge}$ [nm] at an intersection between the tangent and the abscissa axis using a conversion equation (F1) below is referred to as the energy gap $T_{77K}$ at 77 [K].

$T_{77K}$ [eV]=1239.85/$\lambda_{edge}$  Conversion Equation:

The tangent to the rise of the phosphorescence spectrum on the short-wavelength side is drawn as follows. While moving on a curve of the phosphorescence spectrum from the short-wavelength side to the maximum spectral value closest to the short-wavelength side among the maximum spectral values, a tangent is checked at each point on the curve toward the long-wavelength of the phosphorescence spectrum. An inclination of the tangent is increased as the curve rises (i.e., a value of the ordinate axis is increased). A tangent drawn at a point with the maximum inclination (i.e., a tangent at an inflection point) is defined as the tangent to the rise of the phosphorescence spectrum on the short-wavelength side.

A maximum with a peak intensity of 15% or less of the maximum peak intensity of the spectrum is not included in the above-mentioned maximum closest to the short-wavelength side of the spectrum. The tangent drawn at a point with the maximum spectral value being the closest to the short-wavelength side and having the maximum inclination is defined as the tangent to the rise of the phosphorescence spectrum on the short-wavelength side.

For phosphorescence measurement, a spectrophotofluorometer body F-4500 (manufactured by Hitachi High-Technologies Corporation) is usable. It should be noted that the measurement may be performed not by the above measuring device but by a combination of a cooling unit, a low temperature container, an excitation light source and a light-receiving unit.

Singlet Energy $S_1$

A thin film may be prepared to measure a singlet energy $S_1$ (occasionally referred to as a thin-film method).

A sample is prepared by vapor-depositing a target compound on a quartz substrate to form a 100-nm-thick film and a luminescence spectrum (ordinate axis: luminous intensity, abscissa axis: wavelength) of this sample is measured at a normal temperature (300 K). The singlet energy $S_1$ is calculated from a wavelength value $\lambda_{edge}$ [nm] at an intersection between a tangent drawn to a rise of the luminescence spectrum on the short-wavelength side and the abscissa axis using a conversion equation (F2) below.

$$S_1[eV]=1239.85/\lambda_{edge} \qquad \text{Conversion Equation (F2):}$$

An absorption spectrum is measured using a spectrophotometer. For instance, a spectrophotometer (device name: U3310, manufactured by Hitachi, Ltd.) is usable.

The tangent to the rise of the luminescence spectrum on the short-wavelength side is drawn as follows. While moving on a curve of the luminescence spectrum from the short-wavelength side to the maximum spectral value closest to the short-wavelength side among the maximum spectral values, a tangent is checked at each point on the curve toward the long-wavelength of the luminescence spectrum. An inclination of the tangent is increased as the curve rises (i.e., a value of the ordinate axis is increased). A tangent drawn at a point with the maximum inclination (i.e., a tangent at an inflection point) is defined as the tangent to the rise of the luminescence spectrum on the short-wavelength side.

A maximum with a peak intensity of 15% or less of the maximum peak intensity of the spectrum is not included in the above-mentioned maximum closest to the short-wavelength side of the spectrum. The tangent drawn at a point with the maximum spectral value is the closest to the short-wavelength side and has the maximum inclination is defined as the tangent to the rise of the luminescence spectrum on the short-wavelength side.

It should be noted that a significant difference between a measurement result obtained using the sample vapor-deposited on the quartz substrate and a measurement result obtained using a solution is supposed to be attributed to, for instance, a formation of a molecular aggregate and/or a strong interrelationship with a solvent. Accordingly, the above measurement may be performed on a sample prepared by co-depositing the target compound and suitable another material with a large energy gap unlikely to form an exciplex on a quartz substrate.

A measurement method of the singlet energy $S_1$ using a solution (occasionally referred to as a solution method) may be performed as follows.

A 10 μmol/L toluene solution of a target compound is prepared and put in a quartz cell. An absorption spectrum (ordinate axis: luminous intensity, abscissa axis: wavelength) of this sample is measured at a normal temperature (300K). A tangent is drawn to a fall of the absorption spectrum on the long-wavelength side and a wavelength value $\lambda_{edge}$ (nm) at an intersection between the tangent and the abscissa axis is assigned to a conversion equation (F3) below to calculate the singlet energy.

$$S_1[eV]=1239.85/\lambda_{edge} \qquad \text{Conversion Equation (F3):}$$

An example of the absorption spectrum measuring device is, but not limited to, a spectrophotometer manufactured by Hitachi, Ltd. (device name: U3310).

The tangent to the fall of the absorption spectrum on the long-wavelength side is drawn as follows. While moving on a curve of the absorption spectrum in a long-wavelength direction from the maximum spectral value closest to the long-wavelength side among the maximum spectral values, a tangent is checked at each point on the curve. An inclination of the tangent is decreased and increased in a repeated manner as the curve falls (i.e., a value of the ordinate axis is decreased). A tangent drawn at a point with the minimum inclination closest to the long-wavelength side (except when absorbance is 0.1 or less) is defined as the tangent to the fall of the absorption spectrum on the long-wavelength side.

A maximum with an absorbance of 0.2 or less is not included in the above-mentioned maximum closest to the long-wavelength side.

Method of Preparing First Compound

The first compound can be prepared by a method described in Chemical Communications p. 10385-10387 (2013) and NATURE Photonics p. 326-332 (2014). The first compound can also be prepared by any one of methods described in, for instance, International Publication Nos. WO 2013/180241, WO 2014/092083 and WO 2014/104346.

Specific examples of the first compound of the first exemplary embodiment are shown below. It should be noted that the first compound according to the invention is not limited to these specific examples.

[Chemical Formula 26]

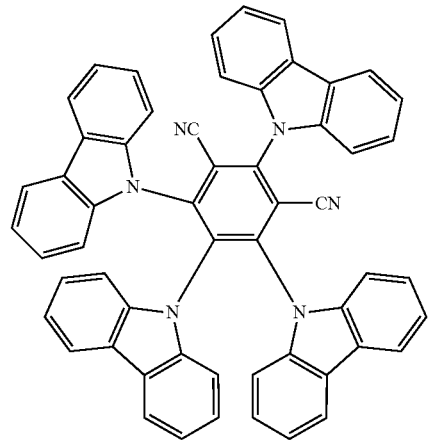

[Chemical Formula 27]

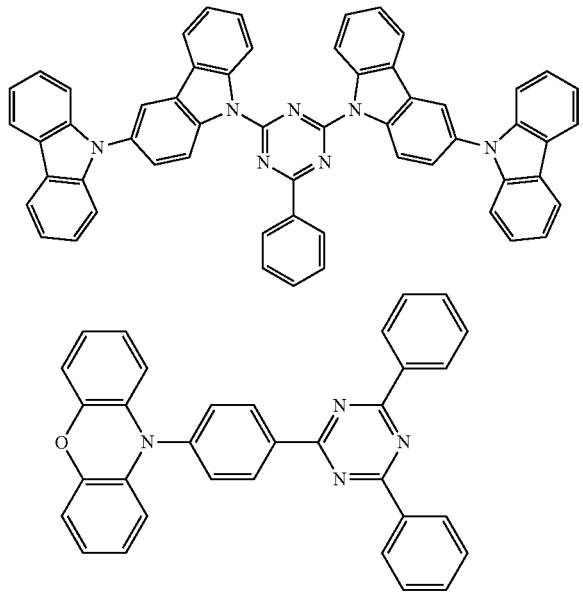

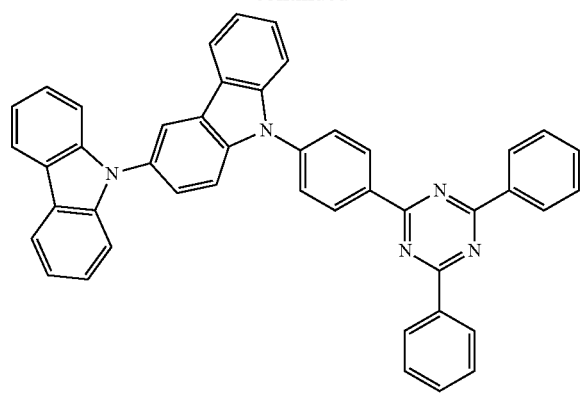
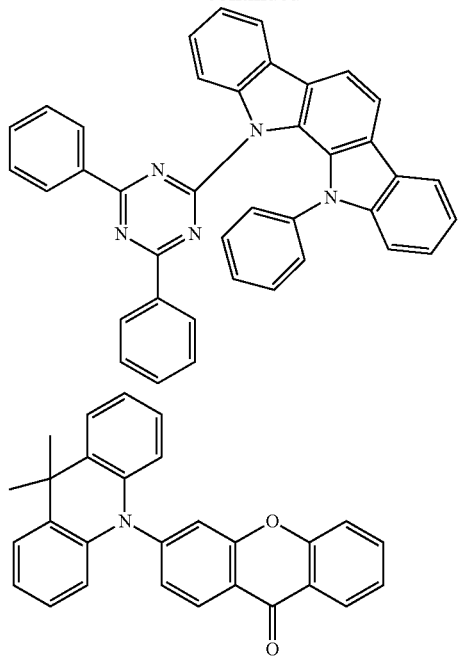
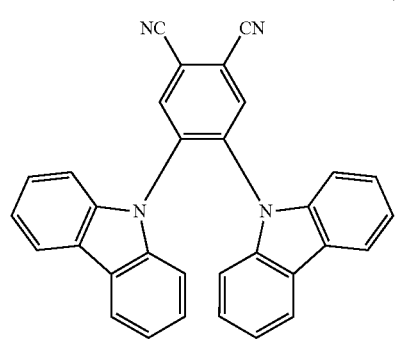
[Chemical Formula 28]
[Chemical Formula 29]
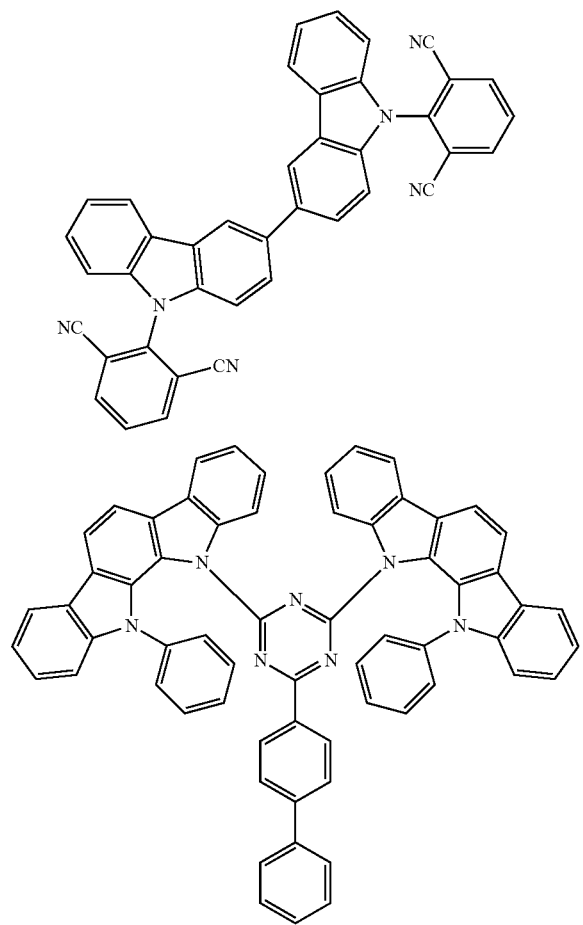
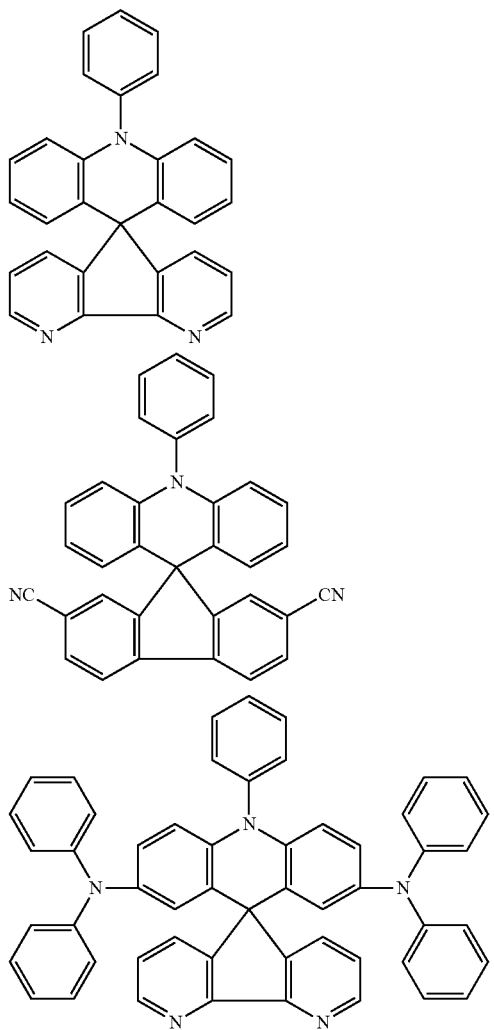

[Chemical Formula 31]
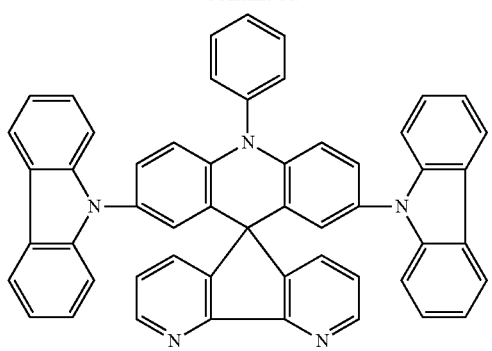
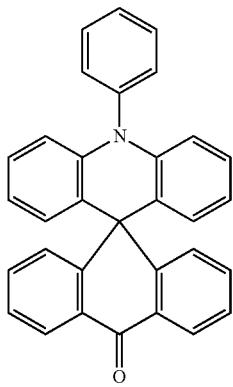
[Chemical Formula 30]
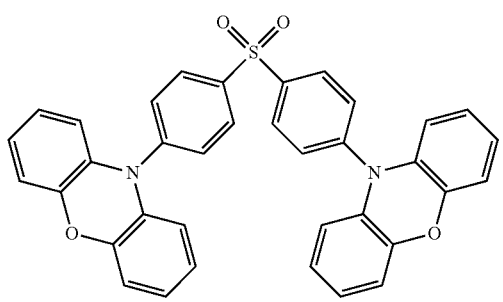
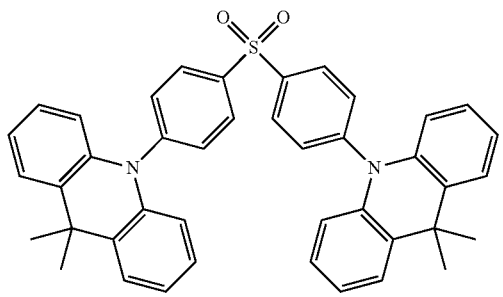
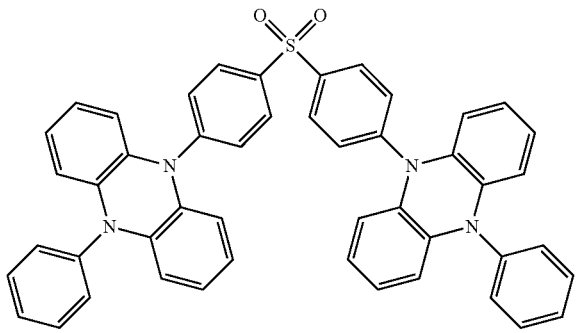
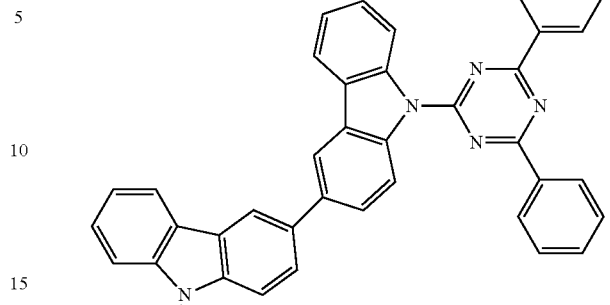
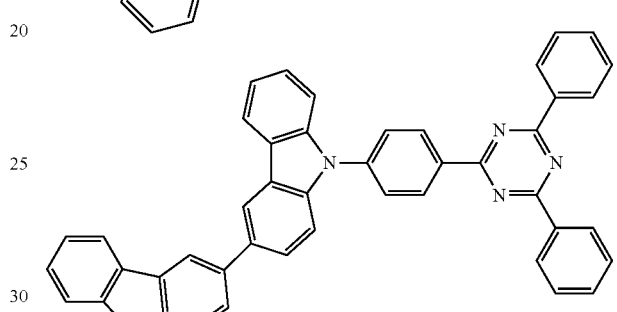
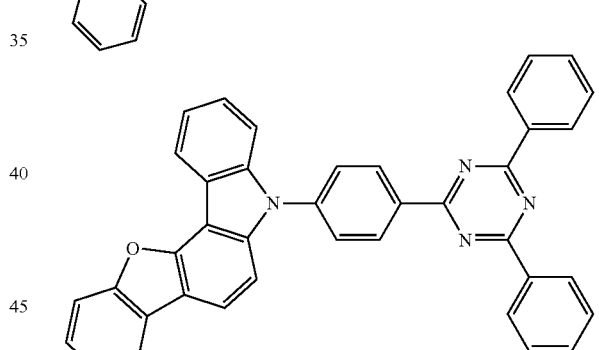
[Chemical Formula 32]
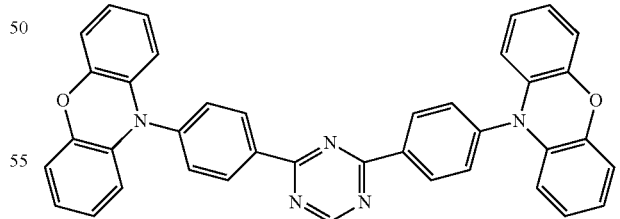

-continued
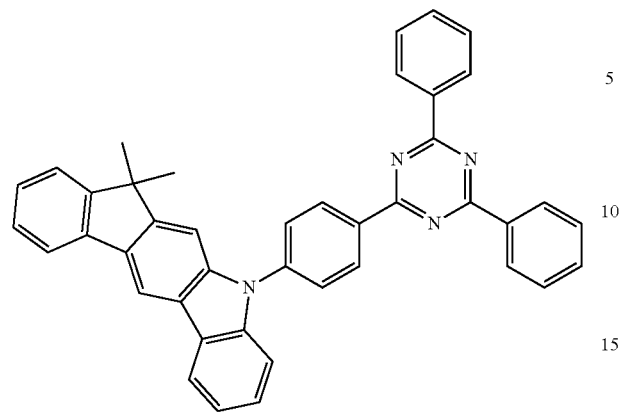
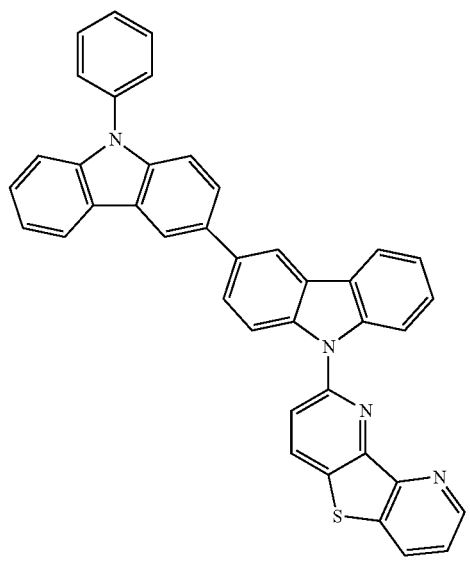
[Chemical Formula 34]
[Chemical Formula 33]
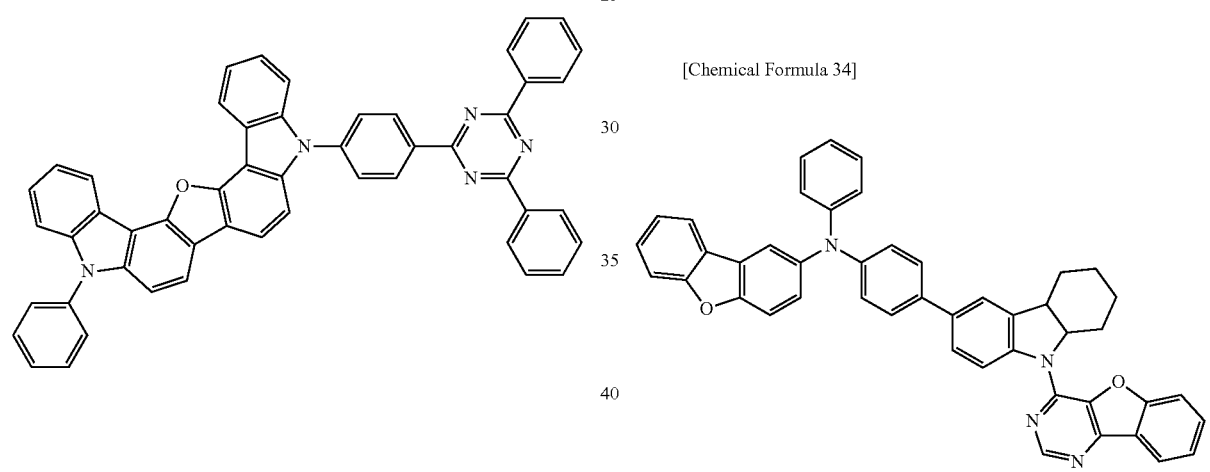
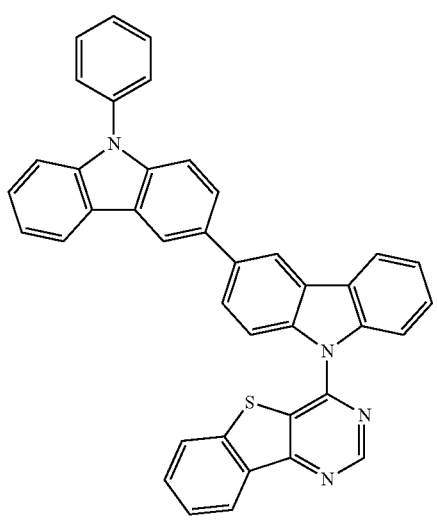
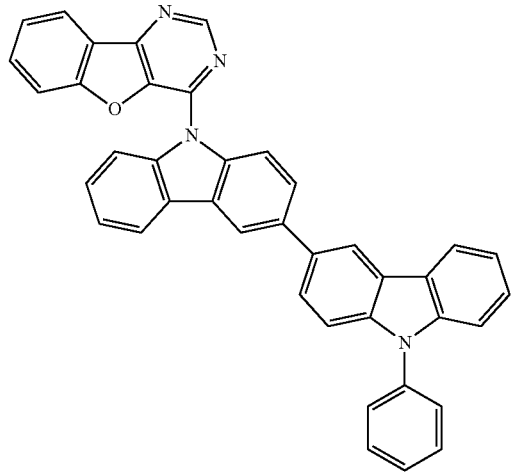

31
-continued
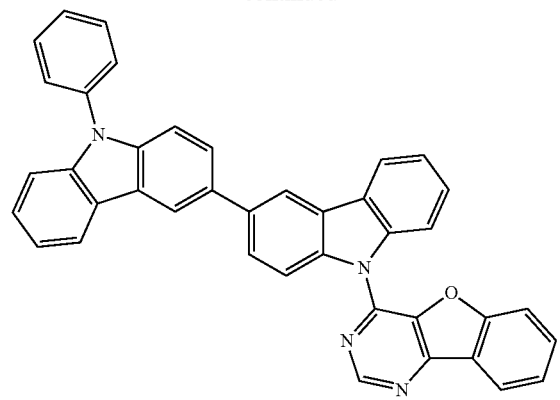
[Chemical Formula 35]
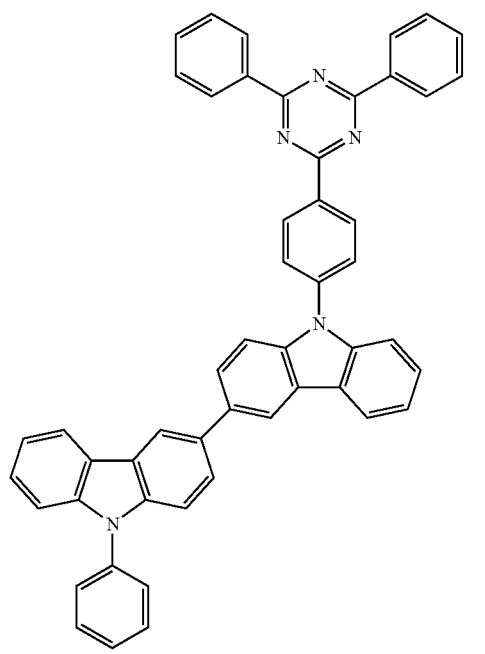
32
-continued
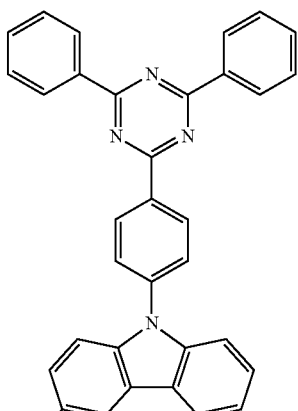
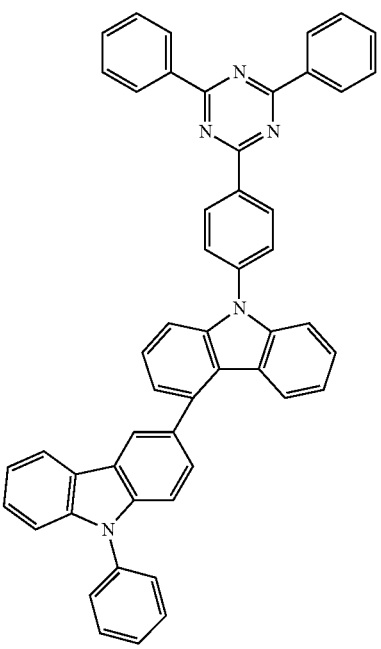

[Chemical Formula 36]
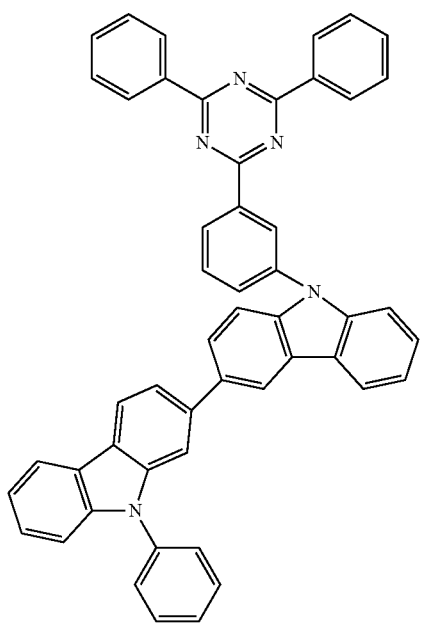
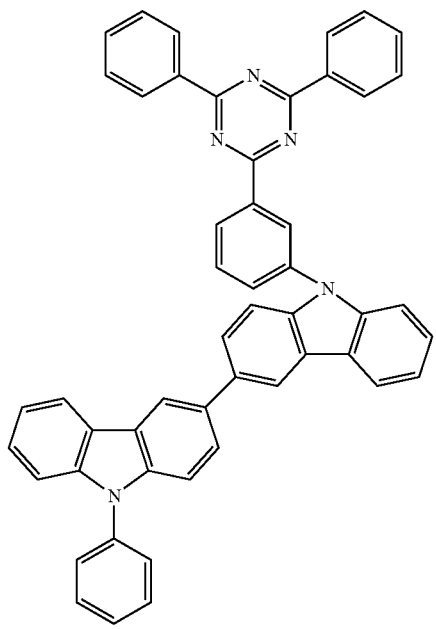
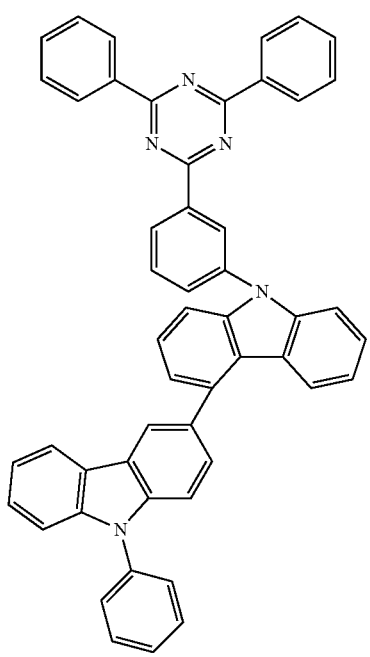
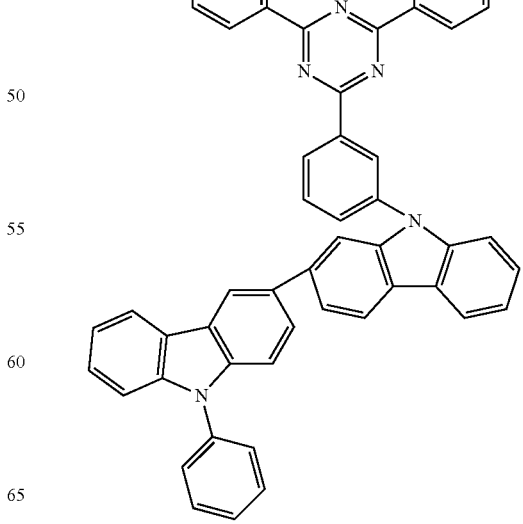

[Chemical Formula 37]
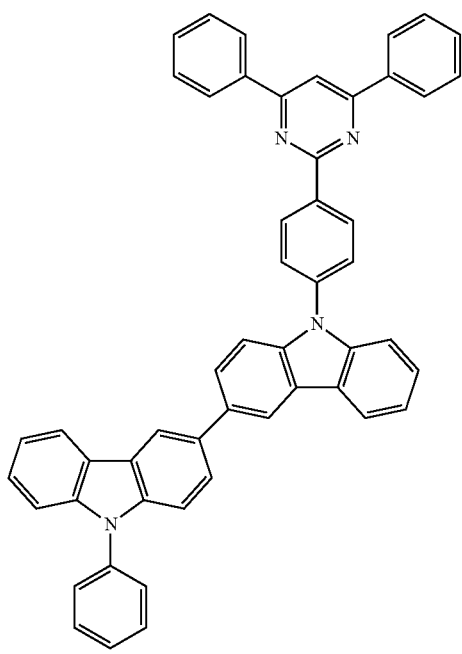
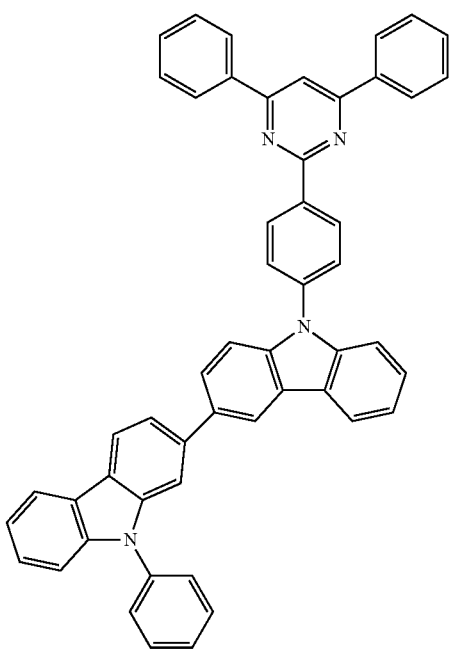
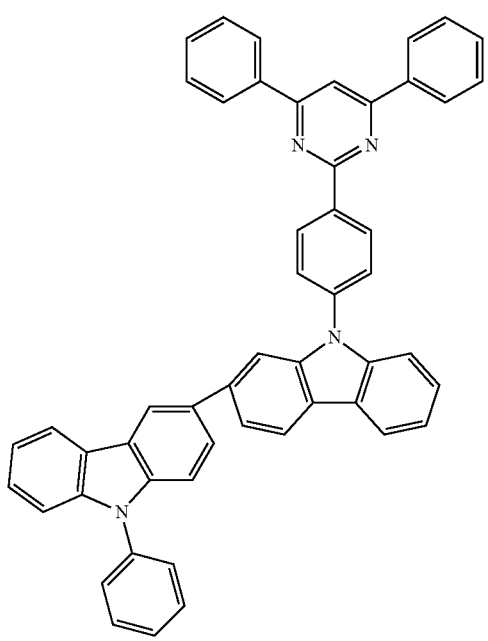
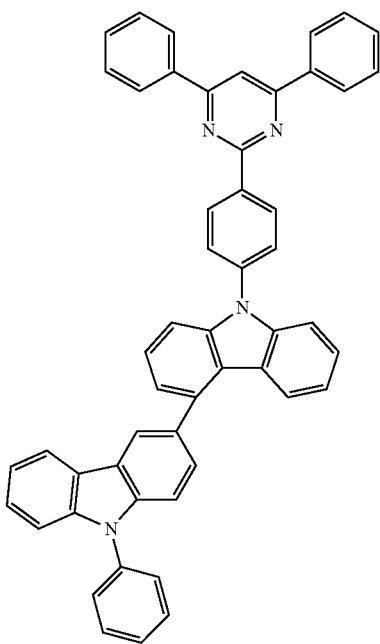

[Chemical Formula 38]
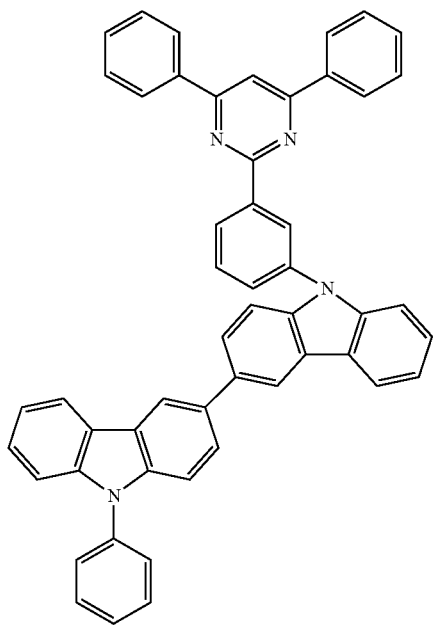
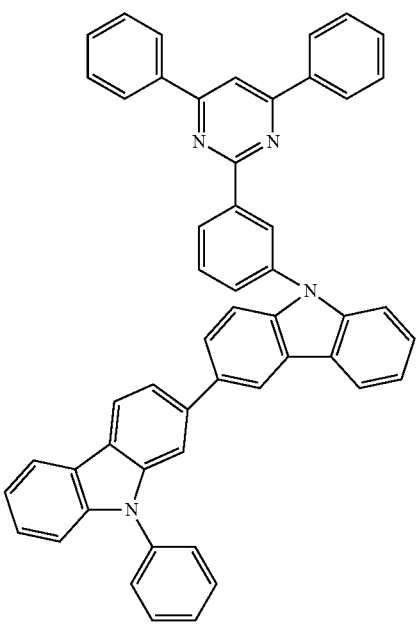
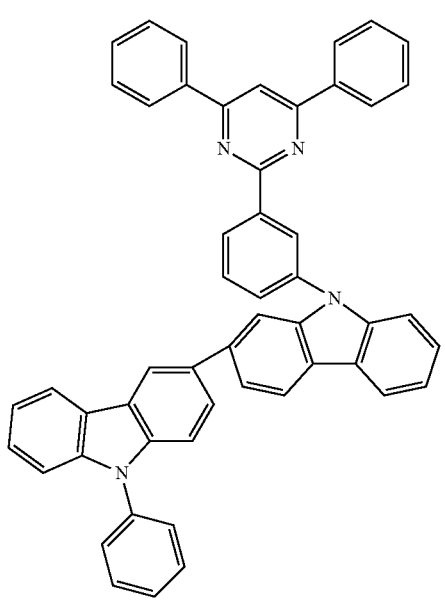
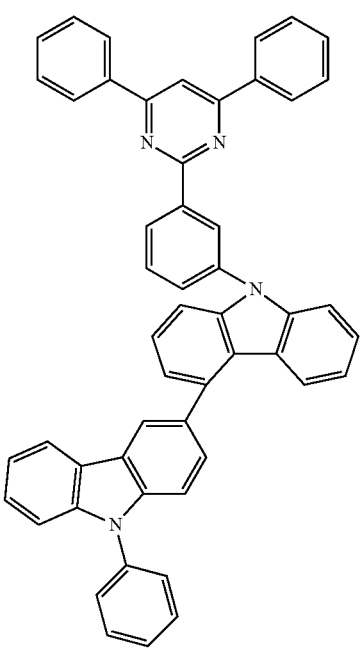

[Chemical Formula 39]
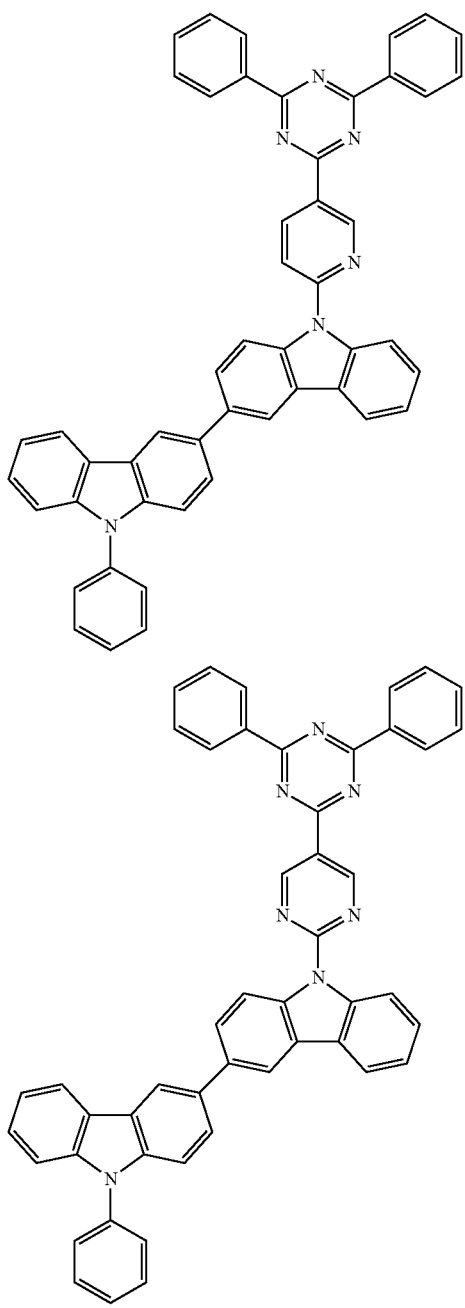
[Chemical Formula 40]
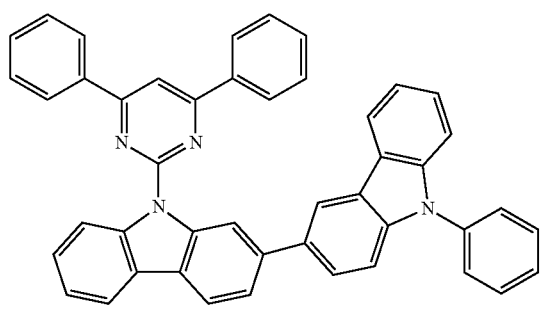
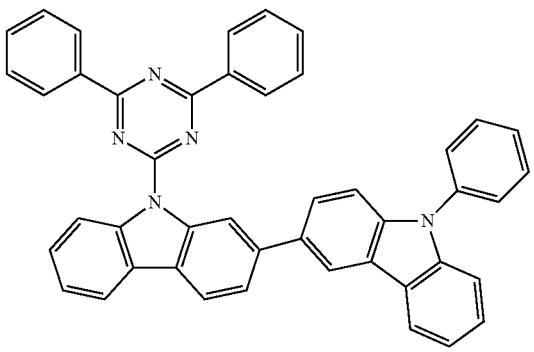
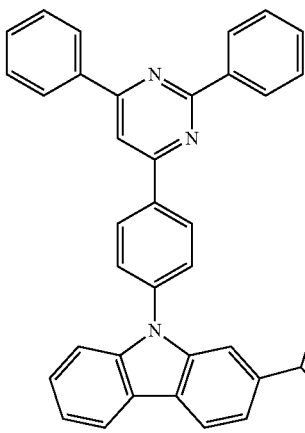
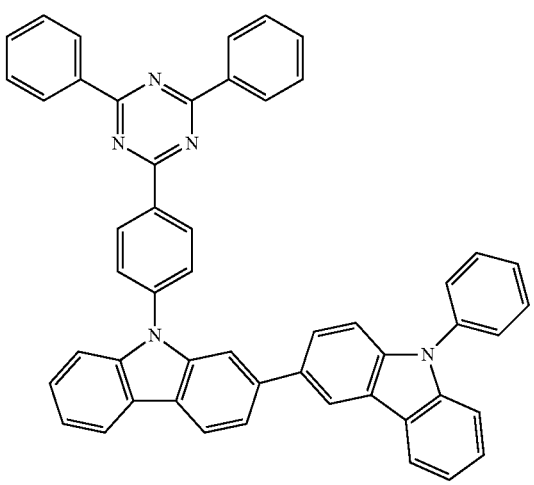

[Chemical Formula 41]
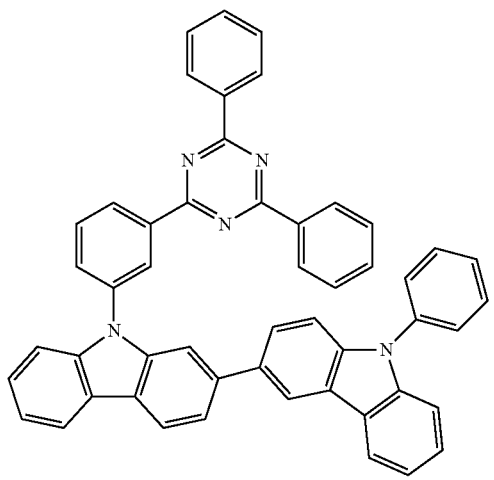
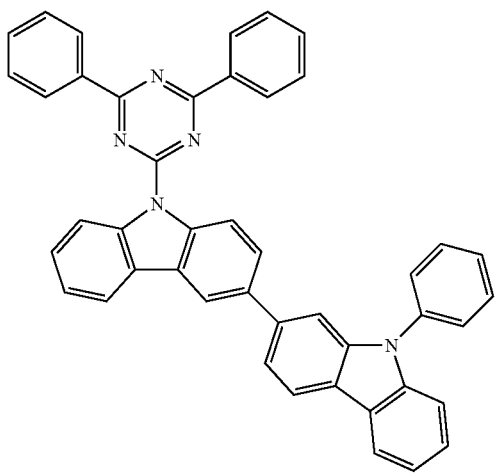
[Chemical Formula 42]
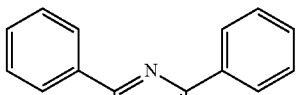
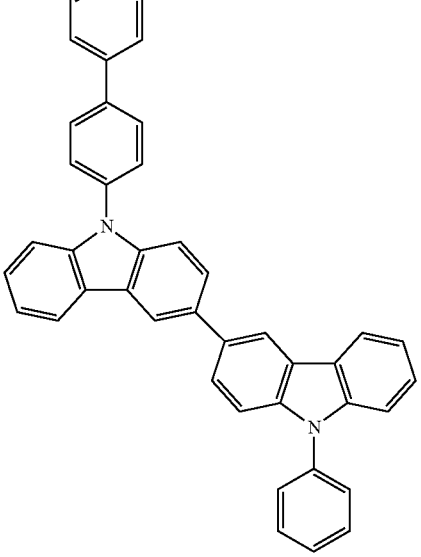
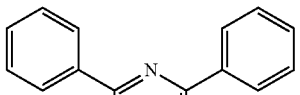
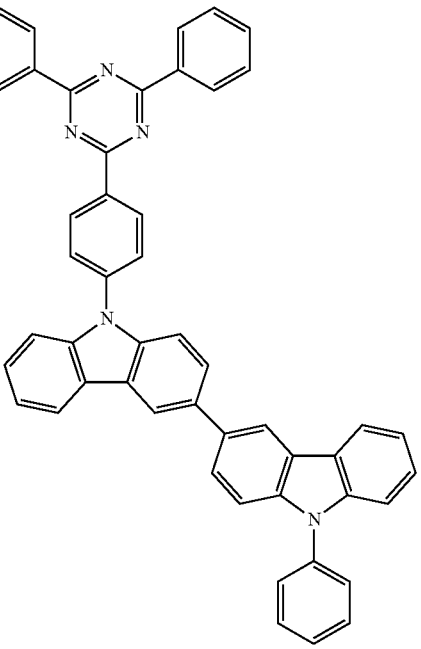

-continued

[Chemical Formula 43]

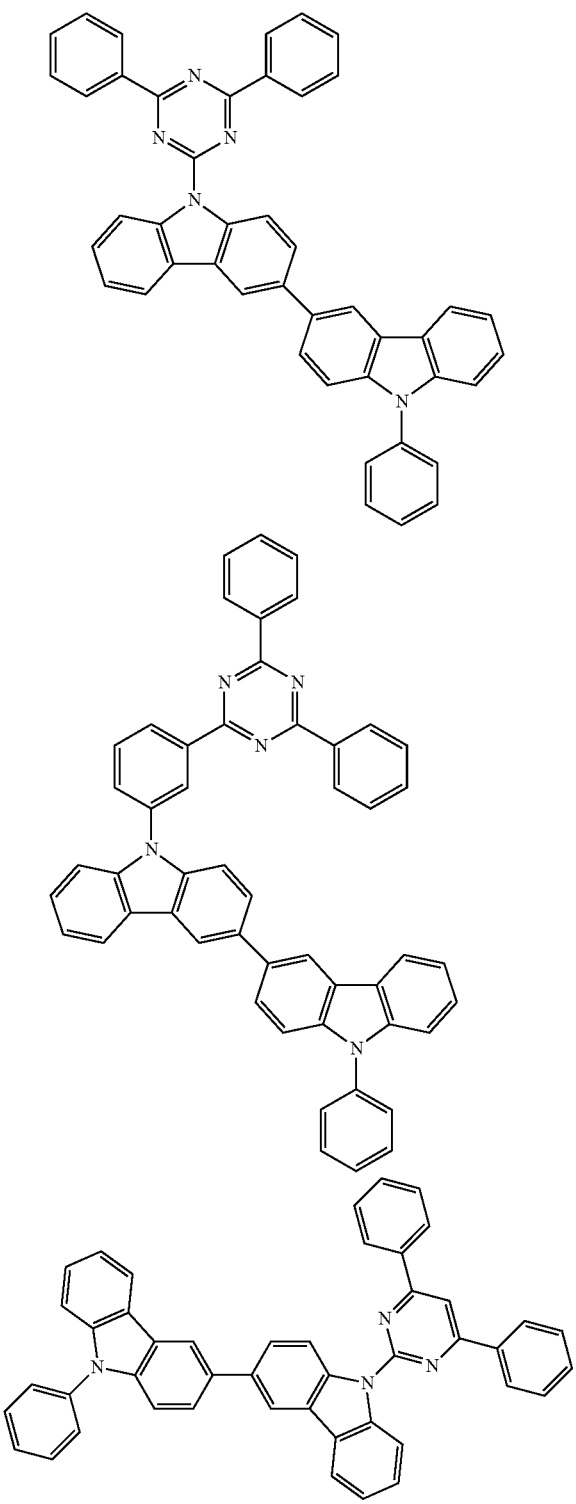

Second Compound

The second compound is a fluorescent compound.

The second compound of the first exemplary embodiment is a compound capable of emitting light with a main peak wavelength ranging from 430 nm to 540 nm. A main peak wavelength of the second compound is preferably 520 nm or less, more preferably 480 nm or less. The main peak wavelength of the second compound is preferably 445 nm or more. The main peak wavelength of the second compound preferably ranges from 430 nm to 480 nm, more preferably from 445 nm to 480 nm. The main peak wavelength herein means a peak wavelength of a luminescence spectrum with a maximum luminous intensity among luminous spectra measured using a toluene solution in which a target compound is dissolved at a concentration ranging from $10^{-6}$ mol/l to $10^{-5}$ mol/l.

The second compound preferably emits blue fluorescence or green fluorescence, more preferably blue fluorescence.

The second compound is preferably a material with a high luminescence quantum yield.

The second compound of the first exemplary embodiment is also preferably a compound represented by a formula (20) below.

[Chemical Formula 44]

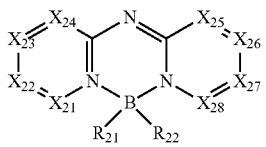

(20)

In the formula (20):

$R_{21}$ and $R_{22}$ are each independently a hydrogen atom or a substituent;

$R_{21}$ and $R_{22}$ as substituents are each independently selected from the group consisting of a halogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted phosphoryl group, a substituted or unsubstituted silyl group, a cyano group, a nitro group, and a substituted or unsubstituted carboxy group;

$R_{21}$ and $R_{22}$ as substituents are directly bonded together to form a ring or form no ring;

$X_{21}$ to $X_{28}$ are each independently $CR_{23}$ or a nitrogen atom;

$R_{23}$ are each independently a hydrogen atom or a substituent;

$R_{23}$ as a substituent are each independently selected from the group consisting of a halogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted phosphoryl group, a substituted or unsubstituted silyl group, a cyano group, a nitro group, and a substituted or unsubstituted carboxy group; and plural $R_{23}$ as substituents are mutually the same or different, plural $R_{23}$ as substituents being directly bonded together to form a ring or forming no ring, or forming a ring via a hetero atom or forming no ring.

The ring formed by bonding $R_{21}$ and $R_{22}$ as substituents together and the ring formed by bonding plural $R_{23}$ as substituents together are each preferably a five-membered ring, a six-membered ring or a seven-membered ring. The ring formed by bonding $R_{21}$ and $R_{22}$ as substituents together and the ring formed by bonding plural $R_{23}$ as substituents together are each an aliphatic ring, an aromatic ring or a hetero ring. The ring formed by bonding $R_{21}$ and $R_{22}$ as substituents together and the ring formed by bonding plural $R_{23}$ as substituents together are each further substituted or not substituted. The ring formed by bonding $R_{21}$ and $R_{22}$ as substituents together and the ring formed by bonding plural $R_{23}$ as substituents together are mutually the same or different.

In the first exemplary embodiment, $X_{21}$ to $X_{28}$ are preferably each independently a carbon atom bonded to $R_{23}$. In this case, the second compound is represented by a formula (20A) below. In the formula (20A), $R_{231}$ to $R_{238}$ each independently mean the same as the above-described $R_{23}$ and $R_{21}$ and $R_{22}$ mean the same as the above-described $R_{21}$ and $R_{22}$ above.

[Chemical Formula 45]

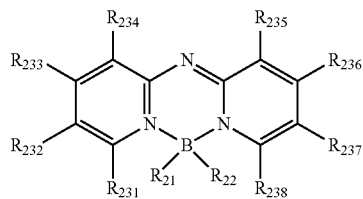

(20A)

In the first exemplary embodiment, it is preferable that any of $R_{231}$ to $R_{234}$ are substituents bonded to each other to form a ring, or any of $R_{235}$ to $R_{238}$ are substituents bonded to each other to form a ring.

In the first exemplary embodiment, it is preferable that any of the substituents of $R_{231}$ to $R_{234}$ are bonded to each other to form a ring and any of the substituents of $R_{235}$ to $R_{238}$ are bonded to each other to form a ring. The ring formed by bonding the substituents is preferably an aromatic six-membered ring. The aromatic six-membered ring is further substituted or not substituted.

The second compound of the first exemplary embodiment is also preferably a compound represented by a formula (22B) below.

[Chemical Formula 46]

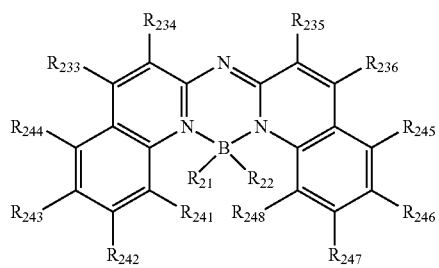

(20B)

In the above formula (20B), $R_{233}$ to $R_{236}$ and $R_{241}$ to $R_{248}$ each independently mean the same as the above-described $R_{23}$ and $R_{21}$ and $R_{22}$ mean the same as the above-described $R_{21}$ and $R_{22}$.

In the formula (20B), it is preferable that $R_{241}$, $R_{242}$, $R_{244}$, $R_{245}$, $R_{247}$ and $R_{248}$ are each a hydrogen atom and $R_{243}$ and $R_{246}$ are each a substituent.

$R_{243}$ and $R_{246}$ as substituents are each independently selected from the group consisting of a halogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted phosphoryl group, a substituted or unsubstituted silyl group, a cyano group, a nitro group, and a substituted or unsubstituted carboxy group.

$R_{243}$ and $R_{246}$ as substituents are preferably each a substituent selected from the group consisting of a halogen atom, a substituted or unsubstituted aromatic hydrocarbon group having 6 to 30 ring carbon atoms and a substituted or unsubstituted alkyl group having 1 to 30 carbon atoms, more preferably a substituted or unsubstituted aromatic hydrocarbon group having 6 to 30 ring carbon atoms.

$R_{21}$ and $R_{22}$ of the first exemplary embodiment are preferably each independently a substituent selected from the group consisting of a halogen atom, a substituted or unsubstituted aromatic hydrocarbon group having 6 to 30 ring carbon atoms and a substituted or unsubstituted alkyl group having 1 to 30 carbon atoms, more preferably a halogen atom, further preferably a fluorine atom.

The second compound is also preferably a compound having a fused ring structure.

It is also preferable that the fused ring structure of the second compound is represented by a formula (2) below and has eight or less rings in total.

[Chemical Formula 47]

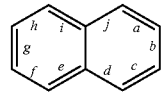

(2)

In the formula (2):
a monocyclic ring or a fused ring may be fused to at least one of positions a, c, d, e, f, h, i and j;
a five-membered ring (monocyclic ring) or a fused ring having a five-membered ring may be fused to at least one of positions b and g;
when a six-membered ring is fused to the positions i and j, a monocyclic ring or a fused ring is also fused to the positions d and e;
when a six-membered ring is fused to the positions d and e, a monocyclic ring or a fused ring is also fused to the positions i and j;
when a fused ring having a five-membered ring is fused to the position b, the five-membered ring of the fused ring is directly fused to the position b; and
when a fused ring having a five-membered ring is fused to the position g, the five-membered ring of the fused ring is directly fused to the position g.
None of a six-membered ring (monocyclic ring) and a six-membered ring of a fused ring is directly bonded to the positions b and g. Further, when a ring is fused to at least one of the positions a, c, f and h, a monocyclic ring is preferably fused. When a fused ring is fused, the fused ring preferably has a five-membered ring.

The total number of the rings of the fused ring structure is preferably six or less, more preferably five or less, further preferably four or less.

Examples of fused ring structure having a structure represented by the formula (2) and having eight or less rings in total are fused ring structures below.

For instance, when a six-membered ring (e.g., a benzene ring) is fused to the position a in the formula (2), the fused ring structure is represented by a formula (2A) below.

[Chemical Formula 48]

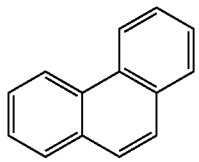

(2A)

For instance, when a six-membered ring is fused to the positions i and j and a six-membered ring is also fused to the positions e and d in the formula (2), the fused ring structure is represented by a formula (2B) below.

[Chemical Formula 49]

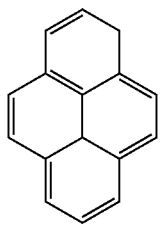

(2B)

For instance, when a five-membered ring is fused to the positions i and j in the formula (2), the fused ring structure is represented by a formula (2C) below. For instance, when a five-membered ring is directly fused to the positions i and j and a ten-member ring (e.g., a naphthalene ring) is further fused to the five-membered ring, the fused ring structure is represented by a formula (2D) below. Alternatively, the fused ring structure is represented by the formula (2D) below when an acenaphthene ring (a fused ring having a five-membered ring) is fused to the position b and the five-membered ring of the acenaphthene ring is directly fused to the position b.

[Chemical Formula 50]

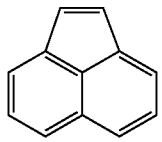

(2C)

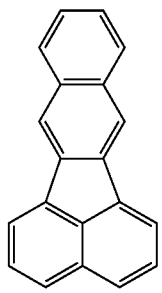

(2D)

For instance, when a five-membered ring is fused to the position c in the formula (2) and a six-membered ring is further fused to the five-membered ring, the fused ring structure is represented by a formula (2E) below.

[Chemical Formula 51]

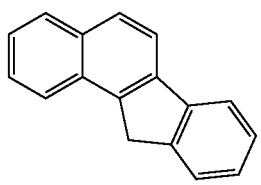

(2E)

For instance, when a ten-membered ring is fused to the position a in the formula (2), the fused ring structure is represented by a formula (2F) below.

[Chemical Formula 52]

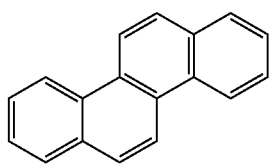

(2F)

For instance, when a six-membered ring is fused to each of the positions a and c in the formula (2), the fused ring structure is represented by a formula (2G) below.

[Chemical Formula 53]

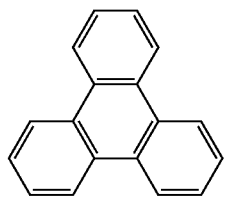

(2G)

In the first exemplary embodiment, "the total number of the rings (or rings in total)" means the total number of the five-membered ring and the six-membered ring forming the fused ring structure that is a main skeleton.

For instance, in the case of the fused ring structure represented by the formula (2A) and the fused ring structure represented by the formula (2C), the total number of the rings is three. In the case of the fused ring structure represented by the formula (2B), the fused ring structure represented by the formula (2E), the fused ring structure represented by the formula (2F) and the fused ring structure represented by the formula (2G), the total number of the rings is four. In the case of the fused ring structure represented by the formula (2D), the total number of the rings is five.

The fused ring structure of the second compound is preferably a structure having energy allowing for emitting light in a blue region and increasing an energy transfer efficiency from the singlet state of the first compound (a delayed fluorescence material) to the singlet state of the second compound. In order to increase the energy transfer efficiency from the singlet state of the delayed fluorescence material (the first compound) to the singlet state of the second compound, it is preferable to inhibit the conflicting energy transfer from the triplet state of the delayed fluorescence material (the first compound) to the triplet state of the second compound. This is because the energy transfer from the triplet state of the delayed fluorescence material (the first compound) to the triplet state of the second compound causes a decrease in the efficiency due to thermal deactivation.

The energy transfer between the triplet states significantly depends on an overlapping size of electron clouds of the first compound (delayed fluorescence material) and the second compound.

For this reason, the energy transfer can be inhibited, for instance, by decreasing a spread of a molecular orbit on a main skeleton of the second compound.

Specifically, the second compound, in which the fused ring forming the main skeleton has the structure represented by the formula (2) and the main skeleton has the eight or less five-membered ring(s) and the six-membered ring(s) in total, is supposed to have a reduced spread of the molecular orbit on the main skeleton, thus inhibiting the energy transfer to the triplet state as compared with a compound in which a six-membered ring is directly fused to the positions b and g of the structure represented by the formula (2) to provide a structure having linearly fused three or more six-membered rings (e.g., an anthracene ring and a naphthacene ring) and a compound with a structure having nine or more five-membered ring(s) and the six-membered ring(s) in total.

Consequently, it is inferred that the energy transfer efficiency from the singlet state of the first compound (delayed fluorescence material) and the singlet state of the second compound is increased to improve the luminous efficiency.

In the first exemplary embodiment, when the second compound has, for instance, a dibenzofuranyl group or a dibenzothienyl group as a side chain of the main skeleton, it is inferred that the overlapping of the electron clouds is further inhibited to further improve the luminous efficiency.

In the first exemplary embodiment, the second compound is also preferably a compound having a moiety that is represented by a formula (20C) below and has an asymmetric structure with respect to an X-Y axis in the formula (20C).

[Chemical Formula 54]

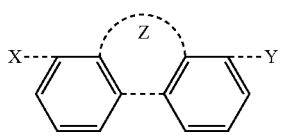

(20C)

In the formula (20C), Z is a substituted or unsubstituted ring structure having 5 or 6 ring carbon atoms.

In the first exemplary embodiment, when the second compound has a fused ring structure as a substituent, the fused ring structure as the substituent is preferably a structure in which none of a six-membered ring (monocyclic ring) and a six-membered ring of the fused ring is directly fused to the positions b and g of the structure represented by the formula (2). Further, the fused ring structure as the substituent is preferably not a structure in which a monocyclic ring and a fused ring are fused to only the position b, only the position g, or only the two positions b and g in the structure represented by the formula (2). Further, the fused ring structure as the substituent is preferably not a structure in which a six-membered ring is fused to only the two positions i and j or only the two positions d and e. In the fused ring structure as the substituent, the total number of the rings is preferably eight or less, more preferably six or less, further preferably five or less, more further preferably four or less.

Examples of the fused ring structure including the structure represented by the formula (2) and having eight or less rings in total include benzofluorene (benzo[a]fluorene, benzo[b]fluorene, benzo[c]fluorene), fluoranthene, benzofluoranthene (benzo[b]fluoranthene, benzo[k]fluoranthene), pyrene, benzo[a]pyrene, chrysene, benzo[a]anthracene, and triphenylene.

In the first exemplary embodiment, the energy gap $T_{77K}$ (M2) at 77 [K] of the second compound is preferably 1.9 eV or more, more preferably 2.0 eV or more.

In the first exemplary embodiment, the second compound is also preferably a compound having a benzofluorene skeleton, fluoranthene skeleton, pyrene skeleton, or chrysene skeleton in order to improve the luminous efficiency.

In the first exemplary embodiment, the second compound is also preferably a compound represented by a formula (21) below.

[Chemical Formula 55]

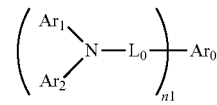

(21)

In the formula (21):
n1 is an integer of 1 or more;
$Ar_0$ is a group having a benzofluorene skeleton, fluoranthene skeleton, pyrene skeleton, or chrysene skeleton;
$Ar_1$ and $Ar_2$ are each independently a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, and a substituted or unsubstituted aralkyl group having 7 to 30 carbon atoms, $Ar_1$ and $Ar_2$ being bonded together to form a saturated or unsaturated ring or forming no ring, when n1 is 2 or more, plural $Ar_1$ being mutually the same or different and plural $Ar_2$ being mutually the same or different;
$L_0$ is a single bond or a linking group, $L_0$ as a linking group being selected from the group consisting of a substituted or unsubstituted aromatic hydrocarbon group having 6 to 30 ring carbon atoms and a substituted or unsubstituted heterocyclic group having 5 to 30 ring atoms; and when n1 is 2 or more, plural $L_0$ are mutually the same or different.

In the first exemplary embodiment, $Ar_0$ in the formula (21) is preferably a group having a pyrene skeleton or a chrysene skeleton.

In the first exemplary embodiment, it is also preferable that n1 is 2 and $L_0$ is a single bond in the formula (21).

When $Ar_0$ is a pyrene skeleton, n1 is 2, and $L_0$ is a single bond, nitrogen atoms of the formula (21) are preferably bonded to a position 1 and a position 6 of the pyrene skeleton. When $Ar_0$ is a chrysene skeleton, n1 is 2, and $L_0$ is a single bond, nitrogen atoms of the formula (21) are preferably bonded to a position 6 and a position 12 of the chrysene skeleton.

In the first exemplary embodiment, $Ar_0$ in the formula (21) is also preferably a group having a benzofluorene skeleton. The group having the benzofluorene skeleton as $Ar_0$ is preferably a group represented by a formula (Ar-1) below.

[Chemical Formula 56]

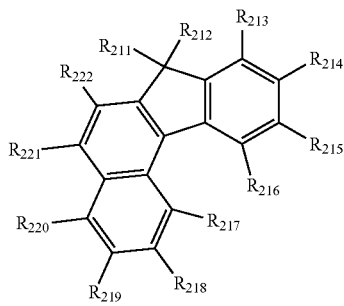

(Ar-1)

In the formula (Ar-1):

$R_{211}$ and $R_{212}$ are each independently a hydrogen atom or a substituent, when $R_{211}$ and $R_{212}$ are substituents, the substituents being each independently selected from the group consisting of a substituted or unsubstituted alkyl group having 1 to 30 carbon atoms and a substituted or unsubstituted aromatic hydrocarbon group having 6 to 30 ring carbon atoms;

$R_{213}$, $R_{214}$, $R_{215}$, $R_{216}$, $R_{217}$, $R_{218}$, $R_{219}$, $R_{220}$, $R_{221}$ and $R_{222}$ are each independently a hydrogen atom, a substituent or a single bond being bonded to $L_0$, at least one of $R_{213}$, $R_{214}$, $R_{215}$, $R_{216}$, $R_{217}$, $R_{218}$, $R_{219}$, $R_{220}$, $R_{221}$ and $R_{222}$ being a single bond being bonded to $L_0$; and $R_{213}$, $R_{214}$, $R_{215}$, $R_{216}$, $R_{217}$, $R_{218}$, $R_{219}$, $R_{220}$, $R_{221}$ and $R_{222}$ as substituents are each independently selected from the group consisting of a halogen atom, a cyano group, a nitro group, a hydroxyl group, a substituted silyl group, a carboxyl group, a substituted or unsubstituted aromatic hydrocarbon group having 6 to 30 ring carbon atoms, a substituted or unsubstituted alkyl group having 1 to 30 carbon atoms, a substituted or unsubstituted alkylamino group having 1 to 30 carbon atoms, a substituted or unsubstituted arylamino group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, and a substituted or unsubstituted alkoxycarbonyl group having 1 to 30 carbon atoms, at least one of a pair of $R_{213}$ and $R_{214}$, a pair of $R_{214}$ and $R_{215}$, a pair of $R_{215}$ and $R_{216}$, a pair of $R_{217}$ and $R_{218}$, a pair of $R_{218}$ and $R_{219}$, a pair of $R_{219}$ and $R_{220}$, a pair of $R_{220}$ and $R_{221}$ and a pair of $R_{221}$ and $R_{222}$ being bonded to each other to form a saturated or unsaturated ring or forming no ring.

In the first exemplary embodiment, the group represented by the formula (Ar-1) is preferably a group represented by a formula (Ar-2) below.

[Chemical Formula 57]

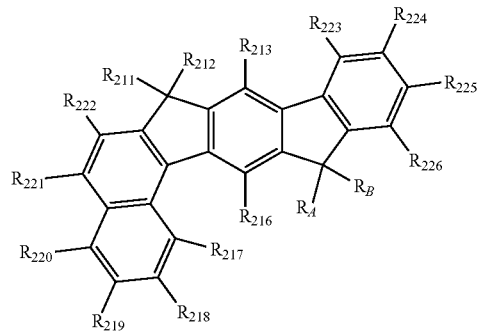

(Ar-2)

In the formula (Ar-2):

$R_{211}$, $R_{212}$, RA and RB are each independently a hydrogen atom or a substituent, $R_{211}$, $R_{212}$, RA and RB as substituents being each independently selected from the group consisting of a substituted or unsubstituted alkyl group having 1 to 30 carbon atoms and a substituted or unsubstituted aromatic hydrocarbon group having 6 to 30 ring carbon atoms;

$R_{213}$, $R_{216}$, $R_{217}$, $R_{218}$, $R_{219}$, $R_{220}$, $R_{221}$, $R_{222}$, $R_{223}$, $R_{224}$, $R_{225}$ and $R_{226}$ are each independently a hydrogen atom, a substituent or a single bond being bonded to $L_0$, at least one of $R_{213}$, $R_{216}$, $R_{217}$, $R_{218}$, $R_{219}$, $R_{220}$, $R_{221}$, $R_{222}$, $R_{223}$, $R_{224}$, $R_{225}$ and $R_{226}$ being a single bond being bonded to $L_0$, $R_{213}$, $R_{216}$, $R_{217}$, $R_{218}$, $R_{219}$, $R_{220}$, $R_{221}$, $R_{222}$, $R_{223}$, $R_{224}$, $R_{225}$ and $R_{226}$ as substituents being each independently selected from the group consisting of a halogen atom, a cyano group, a nitro group, a hydroxyl group, a substituted silyl group, a carboxyl group, a substituted or unsubstituted aromatic hydrocarbon group having 6 to 30 ring carbon atoms, a substituted or unsubstituted alkyl group having 1 to 30 carbon atoms, a substituted or unsubstituted alkylamino group having 1 to 30 carbon atoms, a substituted or unsubstituted arylamino group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, and a substituted or unsubstituted alkoxycarbonyl group having 1 to 30 carbon atoms, at least one of a pair of $R_{217}$ and $R_{218}$, a pair of $R_{218}$ and $R_{219}$, a pair of $R_{219}$ and $R_{220}$, a pair of $R_{220}$ and $R_{221}$, a pair of $R_{221}$ and $R_{222}$, a pair of $R_{223}$ and $R_{224}$, a pair of $R_{224}$ and $R_{225}$ and a pair of $R_{225}$ and $R_{226}$ being bonded to each other to form a saturated or unsaturated ring or forming no ring.

In the first exemplary embodiment, at least one of $R_{221}$ and $R_{225}$ is preferably a single bond being bonded to $L_0$.

In the first exemplary embodiment, $R_{211}$, $R_{212}$, RA and RB are preferably each independently a substituent selected from the group consisting of a substituted or unsubstituted alkyl group having 1 to 30 carbon atoms and a substituted or unsubstituted aromatic hydrocarbon group having 6 to 30 ring carbon atoms.

In the first exemplary embodiment, $Ar_1$ and $Ar_2$ in the formula (21) are preferably each independently a substituent selected from the group consisting of a substituted or unsubstituted aromatic hydrocarbon group having 6 to 30 ring carbon atoms and a substituted or unsubstituted heterocyclic group having 5 to 30 ring atoms, more preferably a substituent selected from the group consisting of a substituted or unsubstituted aromatic hydrocarbon group having 6 to 30 ring carbon atoms.

In the first exemplary embodiment, at least one of $Ar_1$ and $Ar_2$ in the formula (21) is preferably a group represented by a formula (22) below. In this case, $Ar_0$ in the formula (21) is preferably a group having a pyrene skeleton or a chrysene skeleton.

[Chemical Formula 58]

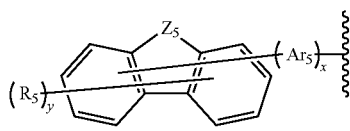
(22)

In the formula (22):
x is an integer of 0 to 3;
y is an integer of 0 to 7;
$Z_5$ represents an oxygen atom, a sulfur atom or a selenium atom;
when x is 0, the group represented by the formula (22) is bonded to a nitrogen atom in the formula (21) by a single bond;
when x is an integer of 1 to 3, $Ar_5$ is a substituted or unsubstituted aromatic hydrocarbon group having 6 to 30 ring carbon atoms;
when x is 2 or more, plural $Ar_5$ are mutually the same or different and are bonded together to form a saturated or unsaturated ring or form no ring;
$R_5$ is selected from the group consisting a halogen atom, a cyano group, a nitro group, a hydroxyl group, a substituted silyl group, a carboxyl group, a substituted or unsubstituted aromatic hydrocarbon group having 6 to 30 ring carbon atoms, a substituted or unsubstituted alkyl group having 1 to 30 carbon atoms, a substituted or unsubstituted alkylamino group having 1 to 30 carbon atoms, a substituted or unsubstituted arylamino group having 6 to 30 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, and a substituted or unsubstituted alkoxycarbonyl group having 1 to 30 carbon atoms, when y is 2 or more, plural $R_5$ being mutually the same or different and being bonded together to form a saturated or unsaturated ring or forming no ring.

In the first exemplary embodiment, $Z_5$ of the formula (22) is preferably an oxygen atom or a sulfur atom, more preferably an oxygen atom.

In the first exemplary embodiment, $Ar_1$ in the formula (21) is preferably a substituent selected from the group consisting of a substituted or unsubstituted aromatic hydrocarbon group having 6 to 30 ring carbon atoms, more preferably a substituent selected from the group consisting of a substituted or unsubstituted aromatic hydrocarbon group having 6 to 20 ring carbon atoms, further preferably a group selected from the group consisting of a phenyl group, biphenyl group, naphthyl group, phenanthryl group, terphenyl group and fluorenyl group.

In the first exemplary embodiment, $Ar_2$ in the formula (21) is preferably a group represented by the formula (22).

In the first exemplary embodiment, at least one of $Ar_1$ and $Ar_2$ in the formula (21) is preferably the group represented by the formula (Ar-1), more preferably the group represented by the formula (Ar-2). In this case, $Ar_0$ in the formula (21) is preferably a group having a benzofluorene skeleton.

In the first exemplary embodiment, n1 in the formula (21) is preferably 1 or 2.

In the first exemplary embodiment, the second compound is also preferably a compound represented by a formula (23) below.

[Chemical Formula 59]

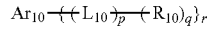
(23)

In the formula (23):
p is an integer of 0 to 5;
q and r are each independently an integer of 1 to 5;
$Ar_{10}$ is a group having a benzofluorene skeleton, fluoranthene skeleton, pyrene skeleton, or chrysene skeleton;
$R_{10}$ is a substituent selected from the group consisting of a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, and a substituted or unsubstituted aralkyl group having 7 to 30 carbon atoms, plural $R_{10}$ being mutually the same or different and being bonded together to form a saturated or unsaturated ring or forming no ring;
when p is 0, $Ar_{10}$ is bonded to $R_{10}$ by a single bond;
when p is an integer of 1 to 5, $L_{10}$ is a linking group selected from the group consisting of a substituted or unsubstituted aromatic hydrocarbon group having 6 to 30 ring carbon atoms and a substituted or unsubstituted heterocyclic group having 5 to 30 ring atoms, plural $L_{10}$ being mutually the same or different and being bonded together to form a saturated or unsaturated ring or forming no ring.

A bonding pattern of the compound represented by the formula (23) is exemplified by bonding patterns shown in Table 2 below.

TABLE 2

| No. | p | q | r | Bonding Pattern |
|---|---|---|---|---|
| (23A) | 0 | 1 | 1 | $Ar_{10}$—$R_{10}$ |
| (23B) | 1 | 1 | 1 | $Ar_{10}$—$L_{10}$—$R_{10}$ |
| (23C) | 0 | 2 | 1 | $Ar_{10}$—$R_{10}$—$R_{10}$, 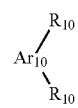 |
| (23D) | 1 | 2 | 1 | $Ar_{10}$—$L_{10}$—$R_{10}$—$R_{10}$, 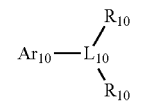 |

TABLE 2-continued

| No. | p | q | r | Bonding Pattern |
|---|---|---|---|---|
| (23E) | 1 | 1 | 2 | $Ar_{10}$ — $L_{10}$ — $R_{10}$, $Ar_{10}$ — $L_{10}$ — $R_{10}$ — $L_{10}$ — $R_{10}$ |
| (23F) | 0 | 2 | 2 | $Ar_{10}$ bonded to $R_{10}$ — $R_{10}$ and $R_{10}$ — $R_{10}$ |
| (23G) | 1 | 2 | 2 | $Ar_{10}$ bonded to $L_{10}$ — $R_{10}$ — $R_{10}$ and $L_{10}$ — $R_{10}$ — $R_{10}$ |
| (23H) | 2 | 2 | 2 | $Ar_{10}$ bonded to $L_{10}$ — $L_{10}$ — $R_{10}$ — $R_{10}$ and $L_{10}$ — $L_{10}$ — $R_{10}$ — $R_{10}$ |

In the first exemplary embodiment, $Ar_{10}$ in the formula (23) is preferably a group having a fluoranthene skeleton, more preferably a group having a fluoranthene skeleton fused with a benzene ring (i.e., a benzofluoranthene skeleton).

In the first exemplary embodiment, the second compound is also preferably a compound having a perylene skeleton or a compound having an anthracene skeleton.

Method of Preparing Second Compound

The second compound can be prepared by a method described in, for instance, International Publication Nos. WO 2008/059713 and WO 2010/122810.

Specific examples of the second compound of the first exemplary embodiment are shown below. It should be noted that the second compound according to the invention is not limited to these specific examples.

[Chemical Formula 60]

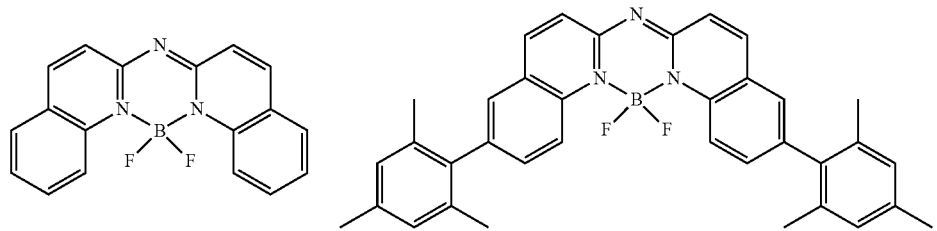

[Chemical Formula 61]

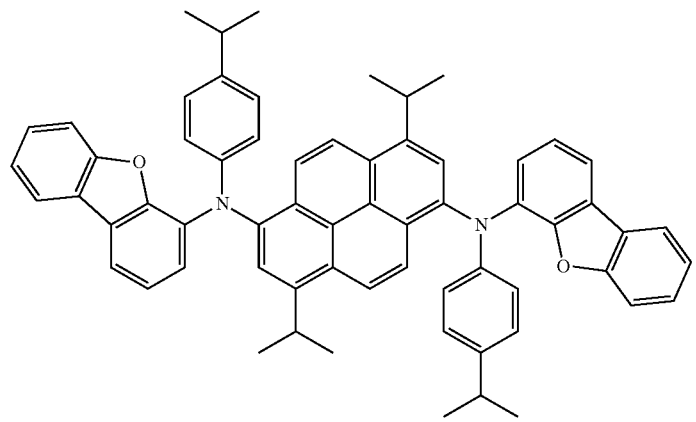

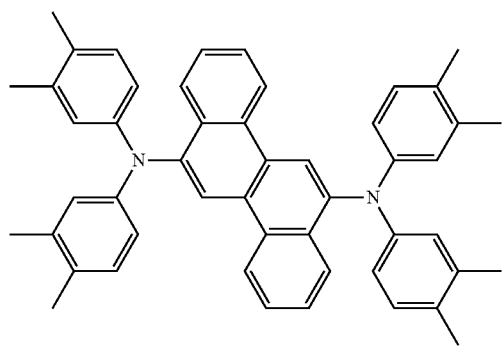
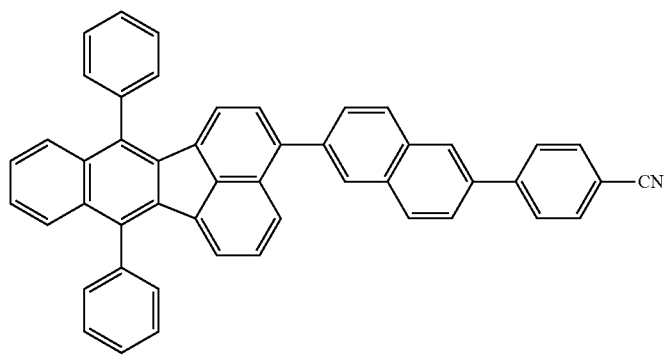
[Chemical Formula 62]
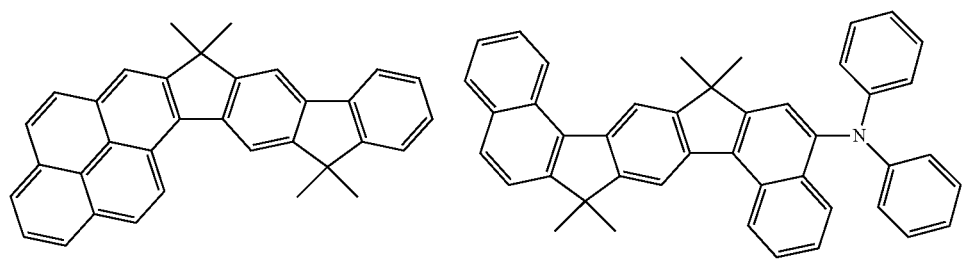
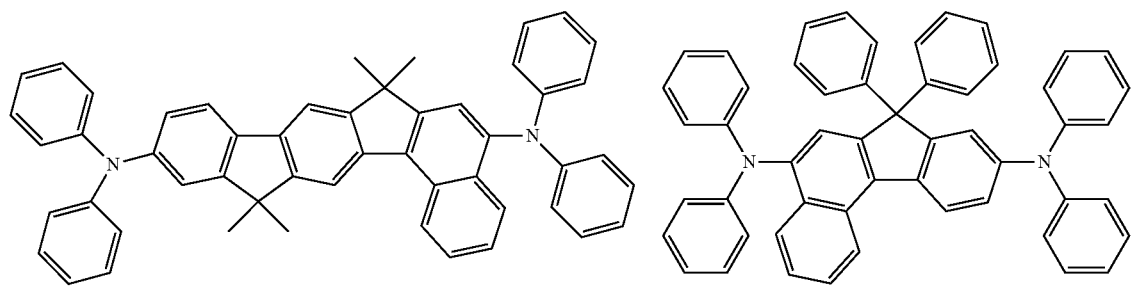

[Chemical Formula 63]
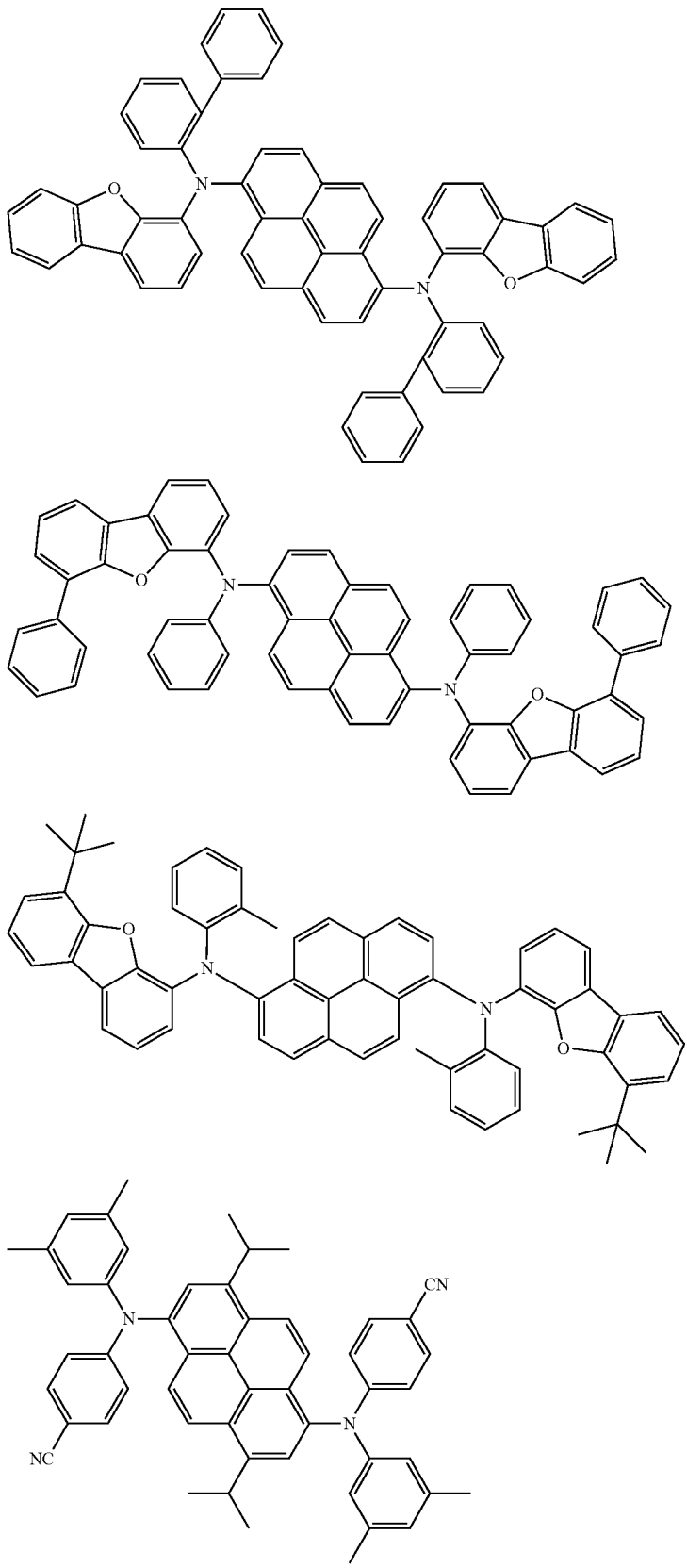

[Chemical Formula 64]
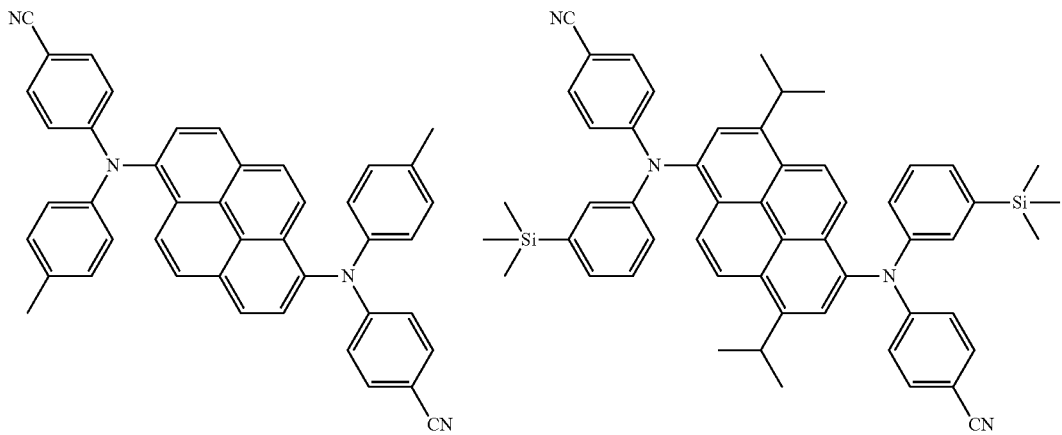
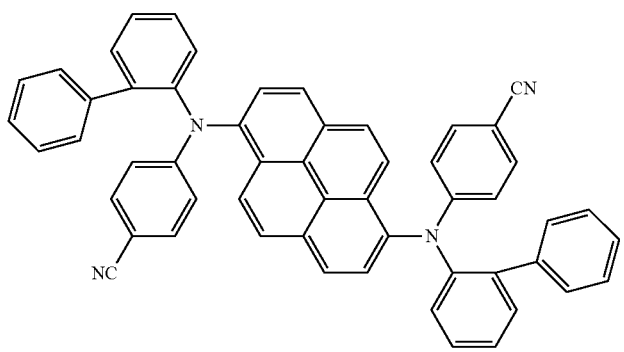
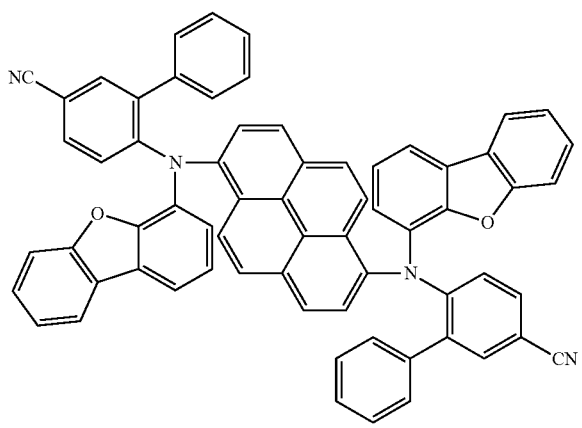
[Chemical Formula 65]
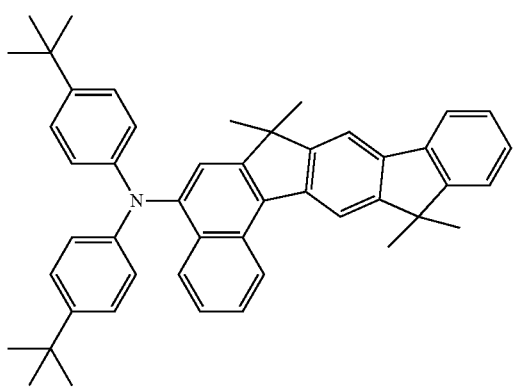

-continued

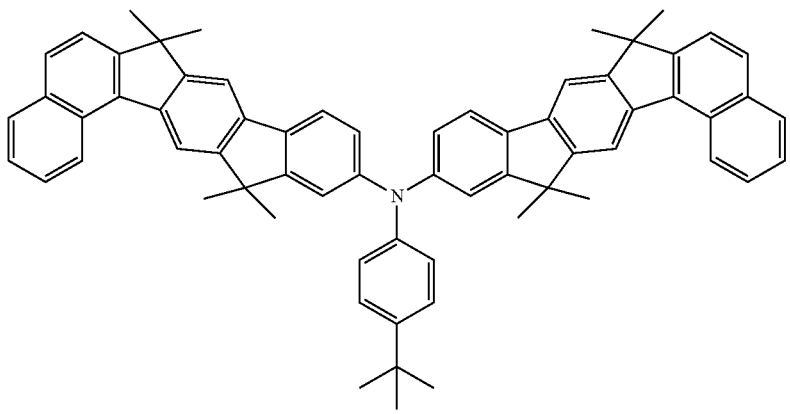

Third Compound

The third compound is a compound represented by a formula (3A) below.

Cz-Az    (3A)

In the formula (3A), Az is a cyclic structure selected from the group consisting of a substituted or unsubstituted pyridine ring, a substituted or unsubstituted pyrimidine ring, a substituted or unsubstituted triazine ring and a substituted or unsubstituted pyrazine ring, and Cz is represented by a formula (3B) below.

[Chemical Formula 66]

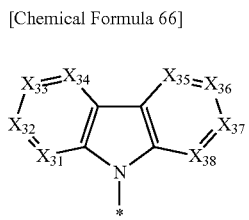

(3B)

In the formula (3B): $X_{31}$ to $X_{38}$ are each independently a nitrogen atom or C-Rx, Rx being each independently a hydrogen atom or a substituent, Rx as a substituent being a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group; plural Rx are mutually the same or different; when two or more of $X_{31}$ to $X_{38}$ are each C-Rx and Rx is a substituent, Rx are bonded together to form a ring or form no ring; and * represents a bonding site to a carbon atom of the ring structure represented by Az.

$X_{31}$ to $X_{38}$ are also preferably each C-Rx.

Cz in the formula (3A) is also preferably represented by a formula (a), a formula (b) or a formula (c) below.

[Chemical Formula 67]

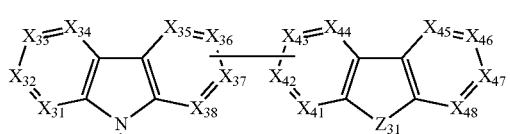

(a)

[Chemical Formula 68]

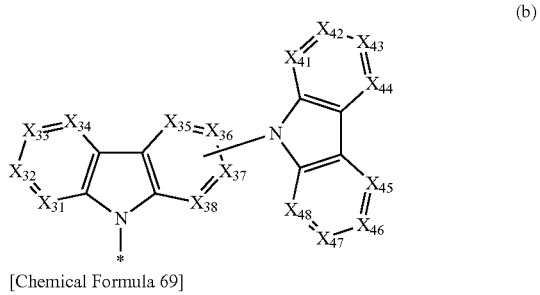

(b)

[Chemical Formula 69]

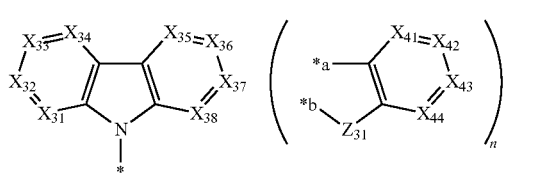

(c)

In the formulae (a), (b) and (c): $X_{31}$ to $X_{38}$ and $X_{41}$ to $X_{48}$ are each independently a nitrogen atom or C-Rx; at least one of $X_{35}$ to $X_{38}$ in the formula (a) is a carbon atom bonded to one of $X_{41}$ to $X_{44}$ and at least one of $X_{41}$ to $X_{44}$ in the formula (a) is a carbon atom bonded to one of $X_{35}$ to $X_{38}$; at least one of $X_{35}$ to $X_{38}$ in the formula (b) is a carbon atom bonded to a nitrogen atom in a five-membered ring of a nitrogen-containing fused ring containing $X_{41}$ to $X_{48}$; *a and *b in the formula (c) each represent a bonding site to one of $X_{31}$ to $X_{38}$, at least one of $X_{35}$ to $X_{38}$ being the bonding site represented by *a, at least another one of $X_{35}$ to $X_{38}$ being the bonding site represented by *b; n is an integer of 1 to 4; Rx are each independently a hydrogen atom or a substituent, Rx as a substituent being a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural Rx being mutually the same or different; when two or more of $X_{31}$ to $X_{38}$ are each C-Rx and Rx is a substituent, plural Rx are bonded together to form a ring or form no ring; when two or more of $X_{41}$ to $X_{48}$ are each C-Rx and Rx is a substituent, Rx are bonded together to form a ring or form no ring; $Z_{31}$ is one selected from the group consisting of an oxygen atom, a sulfur atom, $NR_{30}$ and $C(R_{31})_2$, $R_{30}$ and $R_{31}$ being each independently a hydrogen atom or a substituent, $R_{30}$ and $R_{31}$ as substituents being each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural $R_{30}$ being mutually the same or different, plural $R_{31}$ being mutually the same or different, plural $R_{31}$ as substituents being bonded together to form a ring or forming no ring; and * represents a bonding site to a carbon atom in the cyclic structure represented by Az.

Cz in the formula (3A) is also preferably represented by a formula (a1), a formula (a2) or a formula (b1) below.

[Chemical Formula 70]

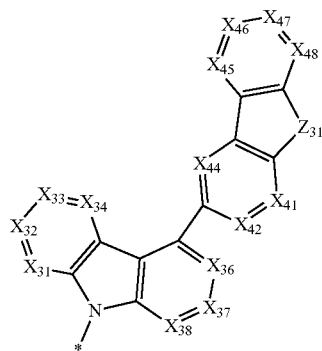

(a1)

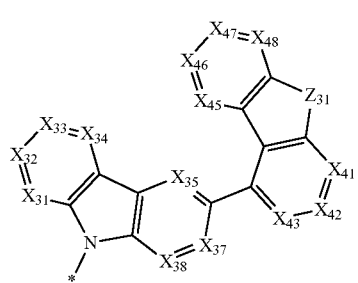

(a2)

[Chemical Formula 71]

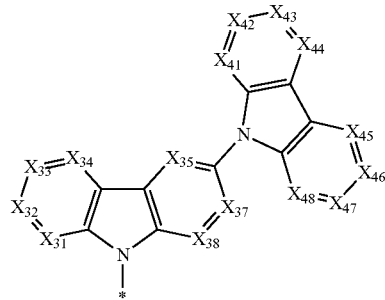

(b1)

In the formulae (a1), (a2) and (b1), $X_{31}$ to $X_{38}$ and $X_{41}$ to $X_{48}$ are each independently a nitrogen atom or C-Rx, Rx being each independently a hydrogen atom or a substituent, Rx as a substituent being a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural Rx being mutually the same or different; when two or more of $X_{31}$ to $X_{38}$ are each C-Rx and Rx is a substituent, Rx are bonded together to form a ring or form no ring; when two or more of $X_{41}$ to $X_{48}$ are each C-Rx and Rx is a substituent, Rx are bonded together to form a ring or form no ring; $Z_{31}$ is one selected from the group consisting of an oxygen atom, a sulfur atom, $NR_{30}$ and $C(R_{31})_2$; $R_{30}$ and $R_{31}$ are each independently a hydrogen atom or a substituent, $R_{30}$ and $R_{31}$ as substituents being each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural $R_{30}$ being mutually the same or different, plural $R_{31}$ being mutually the same or different, plural $R_{31}$ as substituents being bonded together to form a ring or forming no ring; and * represents a bonding site to a carbon atom in the cyclic structure represented by Az.

Cz represented by the formula (a1) is an example where $X_{35}$ is the carbon atom bonded to $X_{43}$ and $X_{43}$ is the carbon atom bonded to $X_{35}$ in the formula (a).

Cz represented by the formula (a2) is an example where $X_{36}$ is the carbon atom bonded to $X_{44}$ and $X_{44}$ is the carbon atom bonded to $X_{36}$ in the formula (a).

Cz represented by the formula (b1) is an example where $X_{36}$ is the carbon atom bonded to the nitrogen atom in the five-membered ring of the nitrogen-containing fused ring containing $X_{41}$ to $X_{48}$ in the formula (b).

$Z_{31}$ is preferably $NR_{30}$.

When $Z_{31}$ is $NR_{30}$, $R_{30}$ is preferably a substituted or unsubstituted aryl group having 6 to 30 ring carbon atoms.

$X_{41}$ to $X_{48}$ exclusive of one being the carbon atom bonded to the cyclic structure represented by the formula (3B) are preferably each C-Rx.

Cz in the formula (3A) is also preferably represented by the formula (c) with n being 1.

Cz in the formula (3A) is also preferably represented by a formula (c1) below. A compound represented by the formula (c1) is an exemplary compound where $X_{36}$ is the bonding site represented by *a and $X_{37}$ is the bonding site represented by *b in the formula (c).

[Chemical Formula 72]

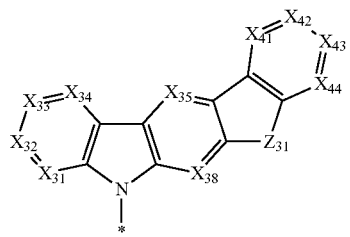

(c1)

In the formula (c1), $X_{31}$ to $X_{35}$, $X_{38}$ and $X_{41}$ to $X_{44}$ are each independently a nitrogen atom or C-Rx, Rx being each independently a hydrogen atom or a substituent, Rx as a substituent being a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural Rx being mutually the same or different; when two or more of $X_{31}$ to $X_{35}$ and $X_{38}$ are each C-Rx and Rx is a substituent, Rx are bonded together to form a ring or form no ring; when two or more of $X_{41}$ to $X_{44}$ are each C-Rx and Rx is a substituent, Rx are bonded together to form a ring or form no ring; $Z_{31}$ is one selected from the group consisting of an oxygen atom, a sulfur atom, $NR_{30}$ and $C(R_{31})_2$; $R_{30}$ and $R_{31}$ are each independently a hydrogen atom or a substituent, $R_{30}$ and $R_{31}$ as substituents being each independently a substituent selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted phosphoryl group, a substituted silyl group, a cyano group, a nitro group, and a carboxy group, plural $R_{30}$ being mutually the same or different, plural $R_{31}$ being mutually the same or different, plural $R_{31}$ as substituents being bonded together to form a ring or forming no ring; and * represents a bonding site to a carbon atom in the cyclic structure represented by Az.

$Z_{31}$ in the formula (c1) is also preferably $C(R_{31})_2$.

When Cz in the formula (3A) is represented by the formula (c) and n is 2, Cz may be represented by a formula (c2) below. When n is 2, the two structures in the parentheses attached with the index of n are fused to the cyclic structure represented by the formula (3B). Cz represented by the formula (c2) below is an example where $X_{32}$ is the bonding site represented by *b, $X_{33}$ is the bonding site represented by *a, $X_{36}$ is the bonding site represented by *a, and $X_{37}$ is the bonding site represented by *b in the formula (c).

[Chemical Formula 73]

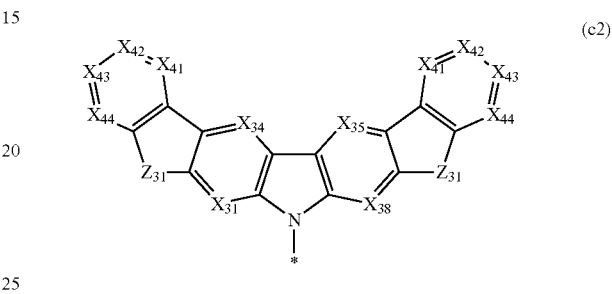

(c2)

In the formula (c2), $X_{31}$, $X_{34}$, $X_{35}$, $X_{38}$, $X_{41}$ to $X_{44}$, $Z_{31}$ and * respectively mean the same as $X_{31}$, $X_{34}$, $X_{35}$, $X_{38}$, $X_{41}$ to $X_{44}$, $Z_{31}$ and * in the formula (c1). Plural $X_{41}$ are mutually the same or different, plural $X_{42}$ are mutually the same or different, plural $X_{43}$ are mutually the same or different, and plural $X_{44}$ are mutually the same or different. Plural $Z_{31}$ are mutually the same or different.

Az in the formula (3A) is preferably a cyclic structure selected from the group consisting of a substituted or unsubstituted pyrimidine ring and a substituted or unsubstituted triazine ring.

Az in the formula (3A) is more preferably a cyclic structure selected from the group consisting of a substituted pyrimidine ring and a substituted triazine ring, a substituent for the pyrimidine ring and the triazine ring being a substituted or unsubstituted aryl group having 6 to 30 ring carbon atoms or a substituted or unsubstituted heteroaryl group having 5 to 30 ring atoms, further preferably the substituent being a substituted or unsubstituted aryl group having 6 to 30 ring carbon atoms.

When the pyrimidine ring or triazine ring as Az has a substituted or unsubstituted aryl group as the substituent, the aryl group preferably has 6 to 20 ring carbon atoms, more preferably 6 to 14 ring carbon atoms, further preferably 6 to 12 ring carbon atoms.

When Az has a substituted or unsubstituted aryl group as the substituent, the substituent is preferably a substituent selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably a substituent selected from the group consisting of a substituted or unsubstituted phenyl group, a substituted or unsubstituted biphenyl group, and a substituted or unsubstituted naphthyl group.

When Az has a substituted or unsubstituted heteroaryl group as the substituent, the substituent is preferably a substituent selected from the group consisting of a substituted or unsubstituted carbazolyl group, a substituted or unsubstituted dibenzofuranyl group, and a substituted or unsubstituted dibenzothienyl group.

Rx are each independently a hydrogen atom or a substituent, Rx as a substituent being preferably a substituent selected from the group consisting of a substituted or unsubstituted aryl group having 6 to 30 ring carbon atoms and a substituted or unsubstituted heteroaryl group having 5 to 30 ring atoms.

When Rx as a substituent is a substituted or unsubstituted aryl group having 6 to 30 ring carbon atoms, Rx as a substituent is preferably a substituent selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group, more preferably a substituent selected from the group consisting of a substituted or unsubstituted phenyl group, a substituted or unsubstituted biphenyl group, and a substituted or unsubstituted naphthyl group.

When Rx as a substituent is a substituted or unsubstituted heteroaryl group having 5 to 30 ring atoms, Rx as a substituent is preferably a substituent selected from the group consisting of a substituted or unsubstituted carbazolyl group, a substituted or unsubstituted dibenzofuranyl group, and a substituted or unsubstituted dibenzothienyl group.

$R_{30}$ and $R_{31}$ as substituents are preferably each independently a substituent selected from the group consisting of a substituted or unsubstituted aryl group having 6 to 30 ring carbon atoms, a substituted or unsubstituted heteroaryl group having 5 to 30 ring atoms, and a substituted or unsubstituted alkyl group having 1 to 30 carbon atoms.

A singlet energy $S_1(M3)$ of the third compound is preferably larger than the singlet energy $S_1(M1)$ of the first compound. In other words, the singlet energy $S_1(M1)$ of the first compound and the singlet energy $S_1(M3)$ of the third compound preferably satisfy a relationship of a numerical expression (Numerical Expression 2) below.

$$S_1(M3) > S_1(M1) \quad \text{(Numerical Expression 2)}$$

The first compound, the second compound and the third compound preferably satisfy the relationships of the numerical expression (Numerical Expression 1) and the numerical expression (Numerical Expression 2).

An energy gap $T_{77K}(M3)$ at 77 [K] of the third compound is preferably larger than the energy gap $T_{77K}(M1)$ at 77 [K] of the first compound.

The third compound may be a delayed fluorescent compound or not.

Method of Preparing Third Compound

The third compound can be prepared by a method described in, for instance, International Publication No. WO 2013/024872.

Specific examples of the third compound of the first exemplary embodiment are shown below. It should be noted that the third compound according to the invention is not limited to these specific examples.

[Chemical Formula 74]

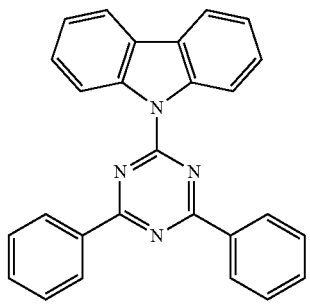

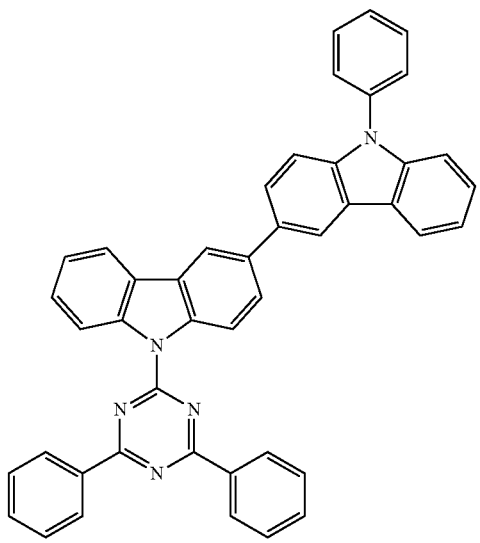

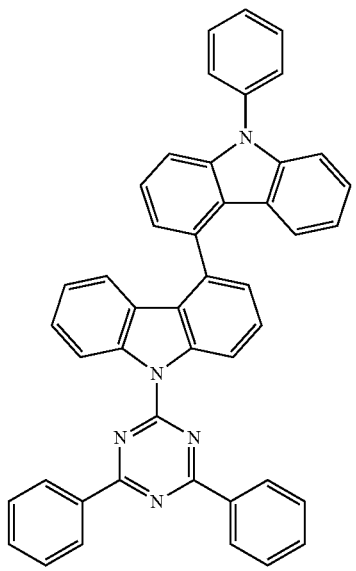

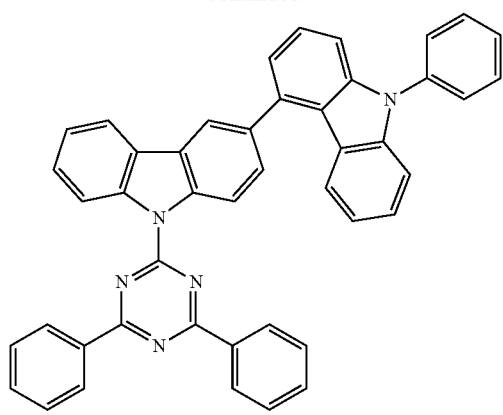
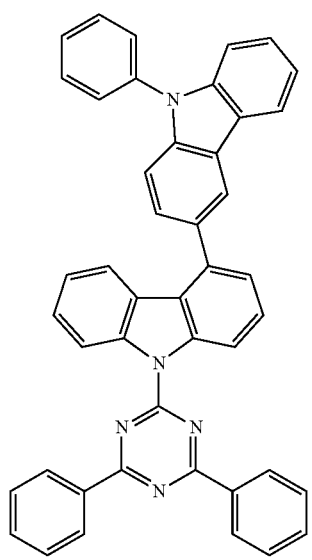
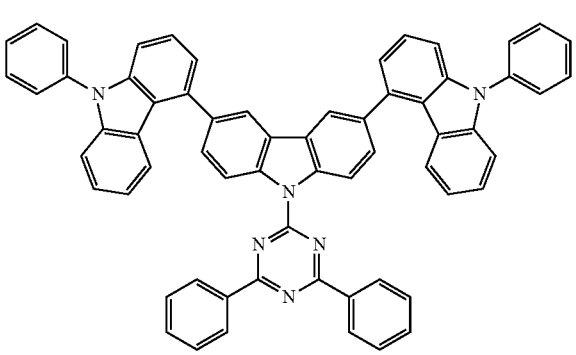
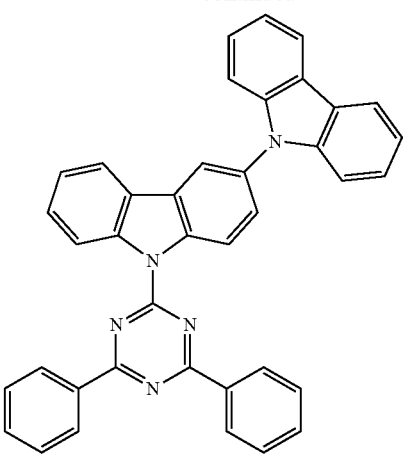
[Chemical Formula 75]
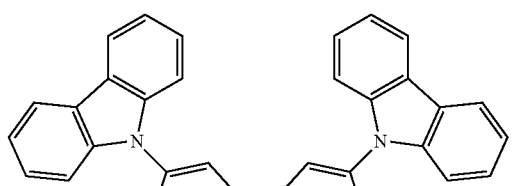
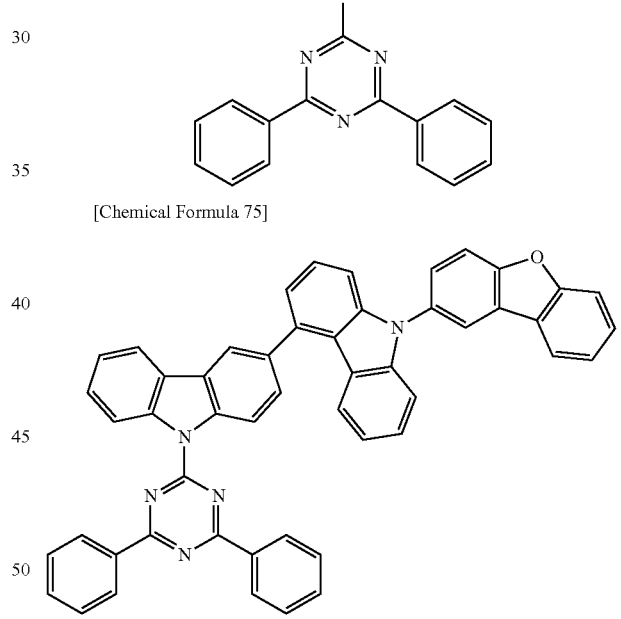
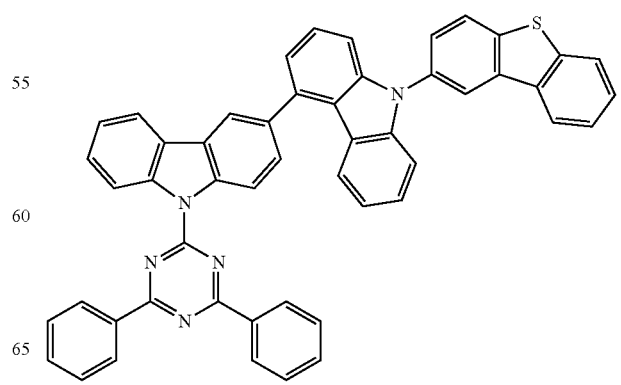

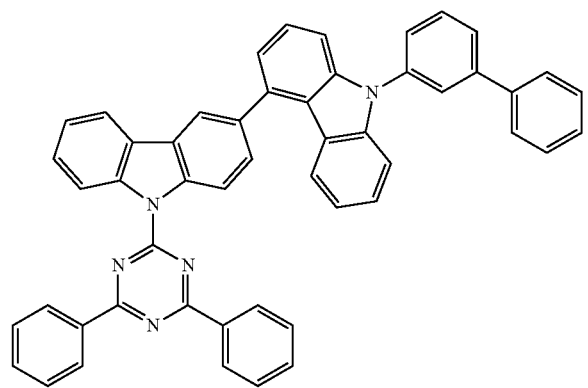
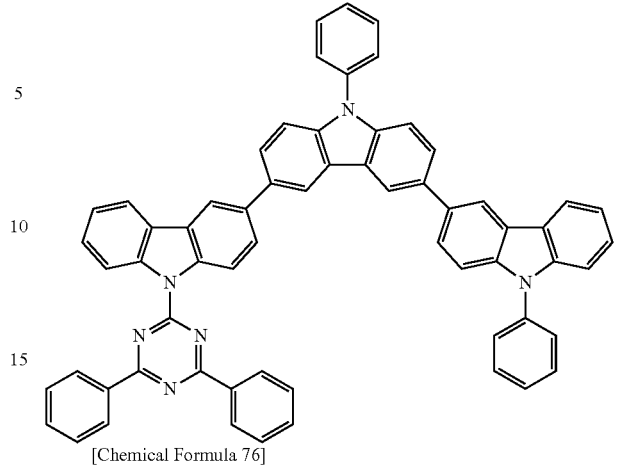
[Chemical Formula 76]
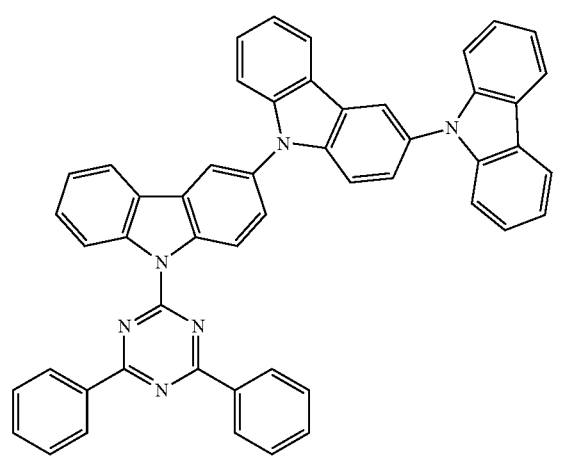
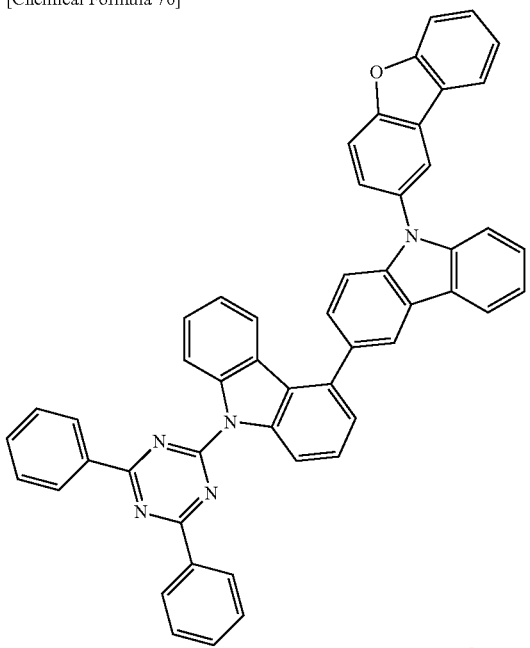
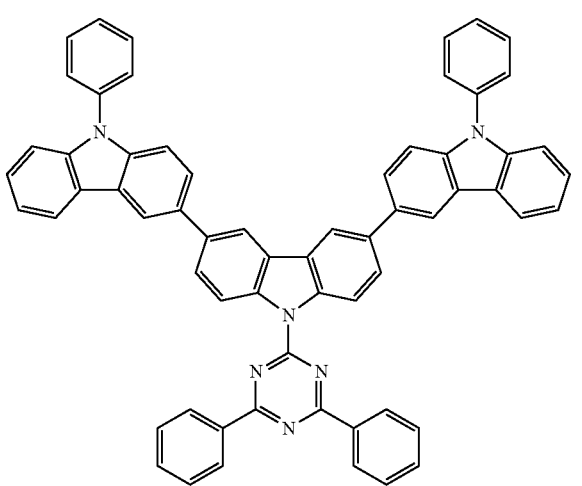
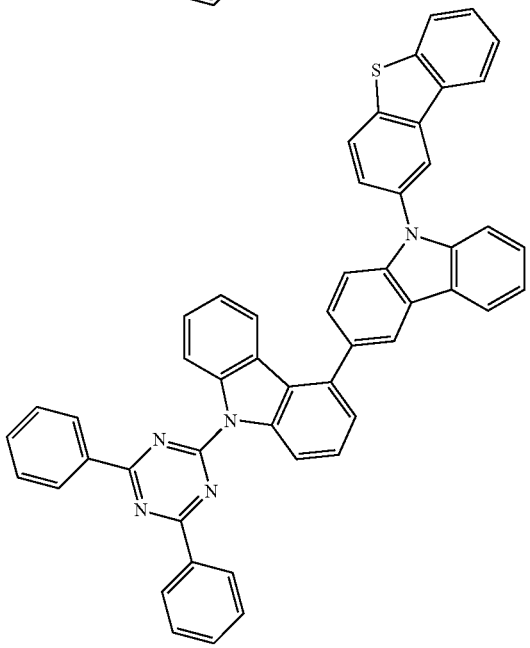

[Chemical Formula 77]
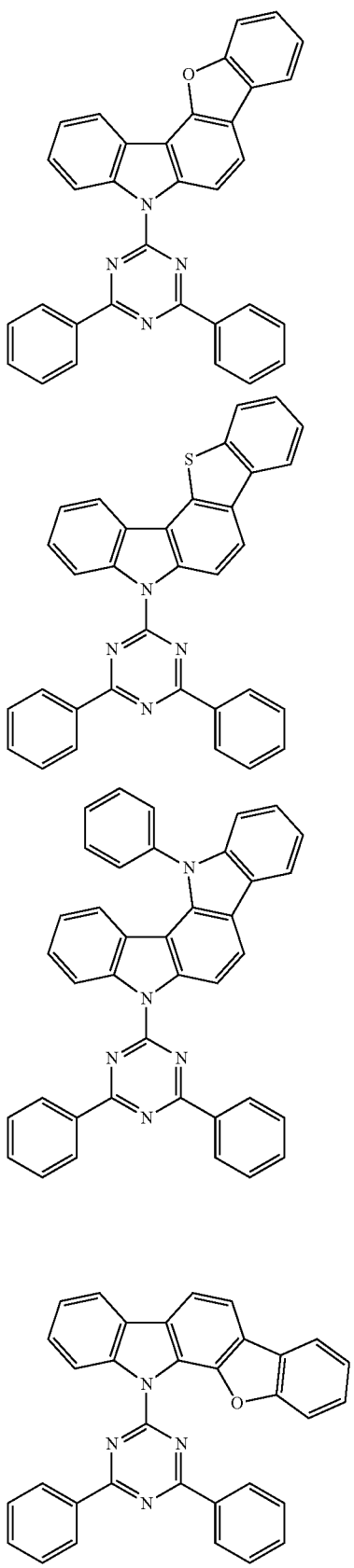
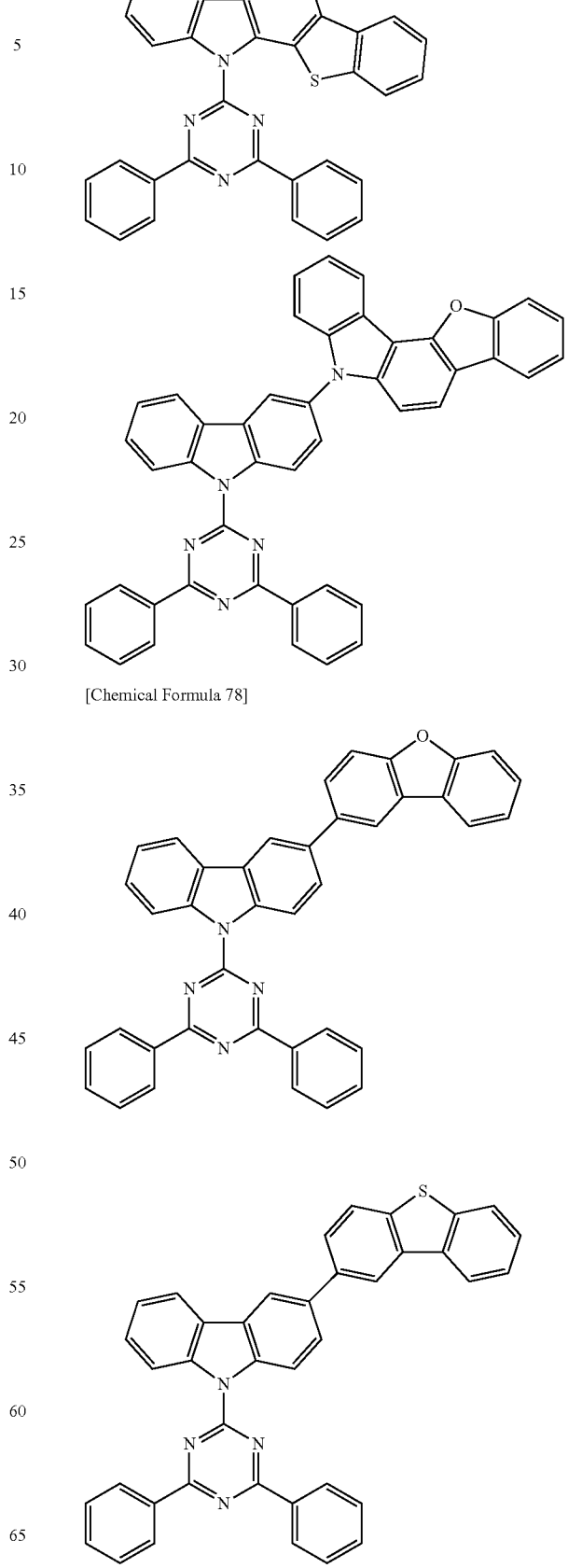
[Chemical Formula 78]

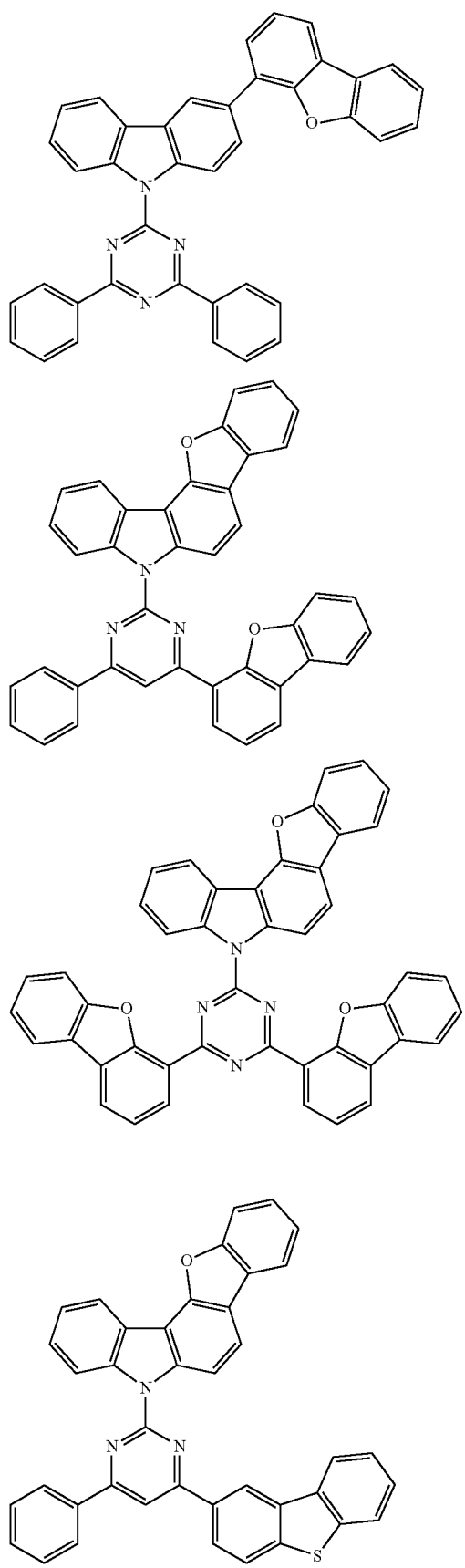
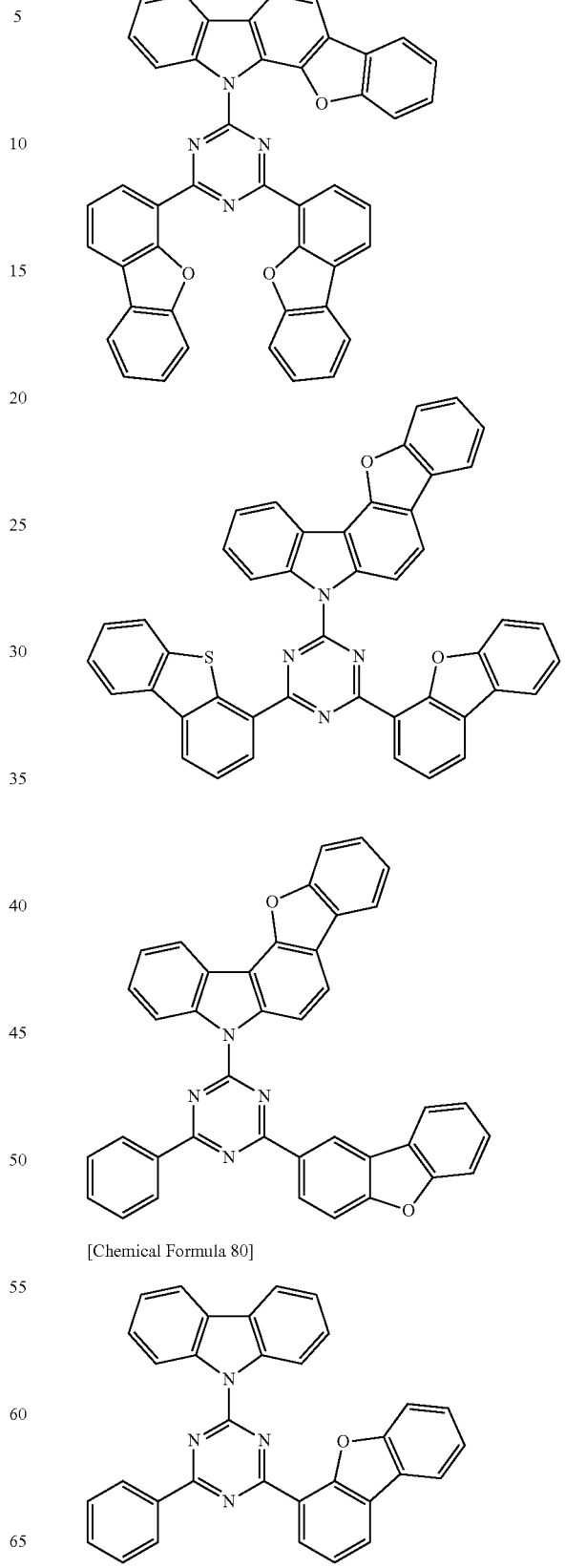
[Chemical Formula 79]
[Chemical Formula 80]

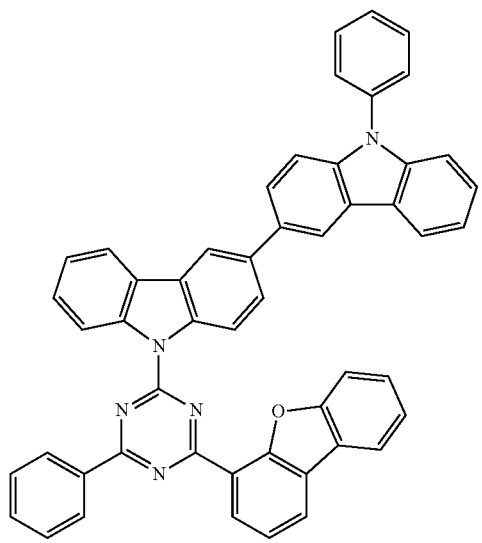
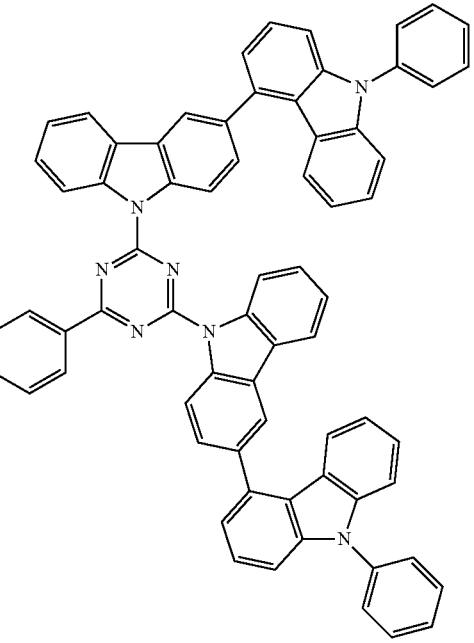
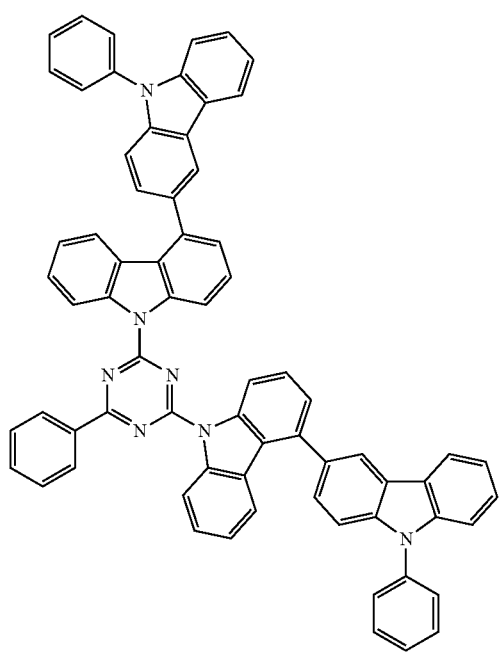
[Chemical Formula 81]
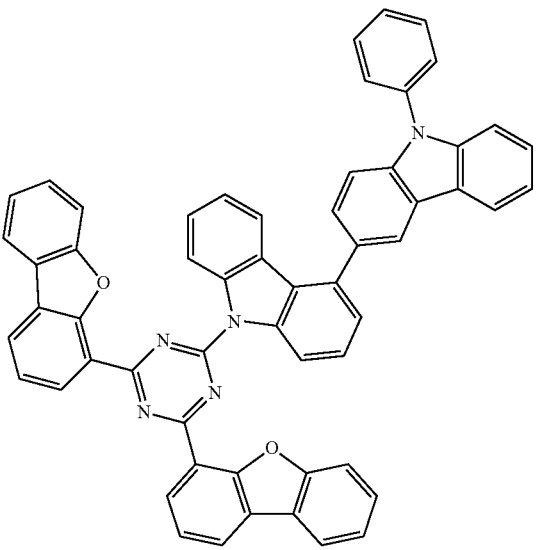

-continued
[Chemical Formula 82]
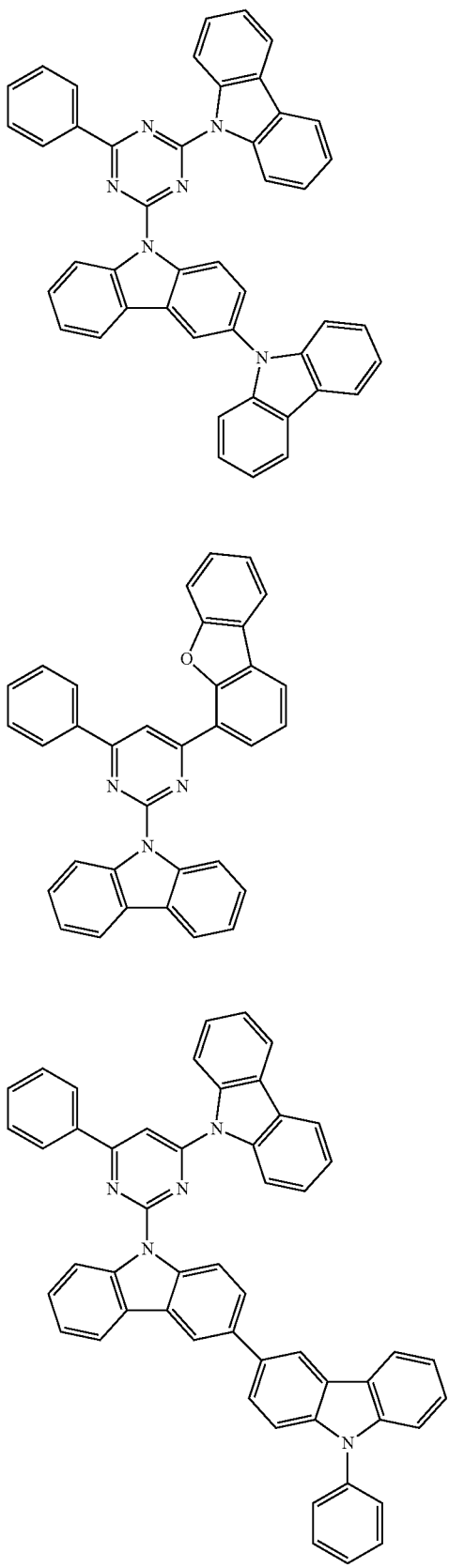
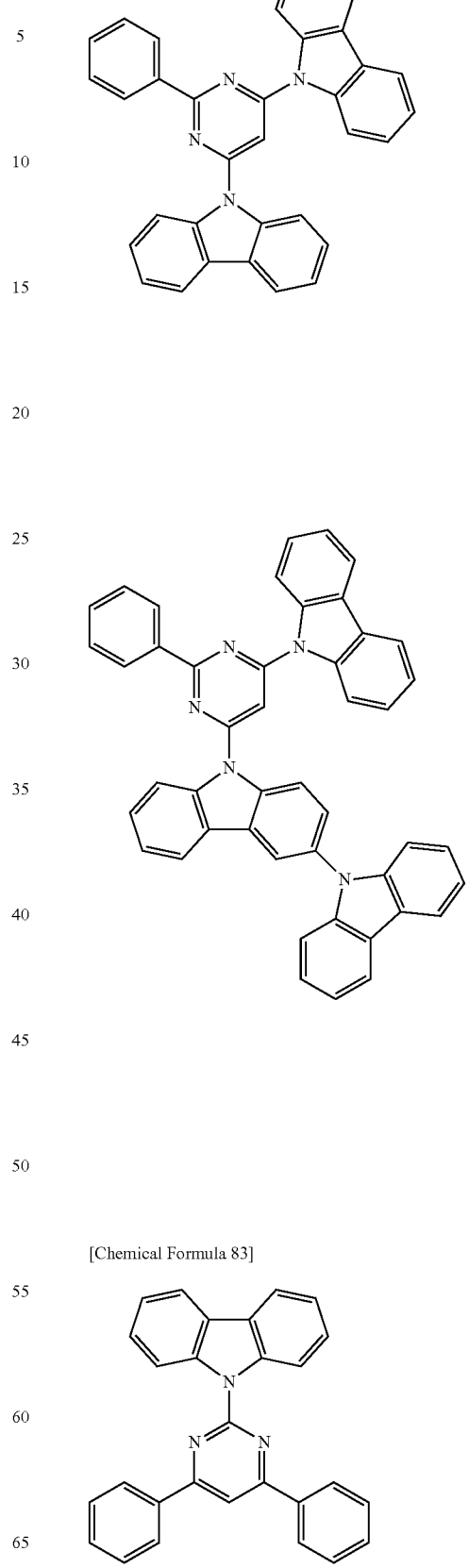
[Chemical Formula 83]
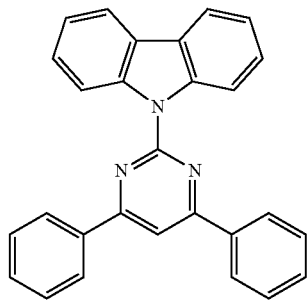

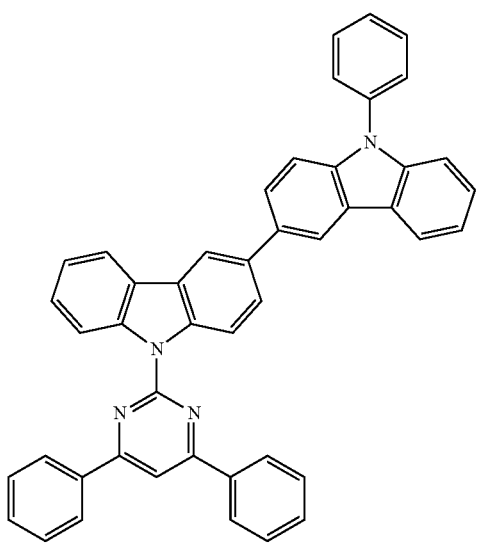
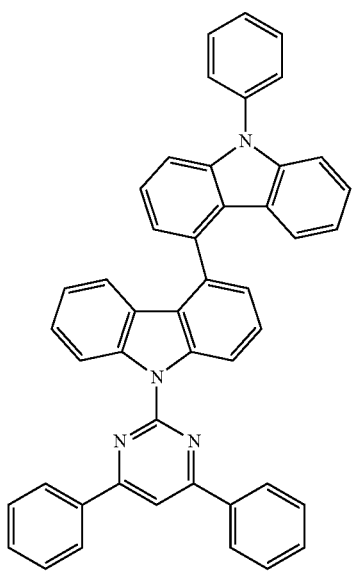
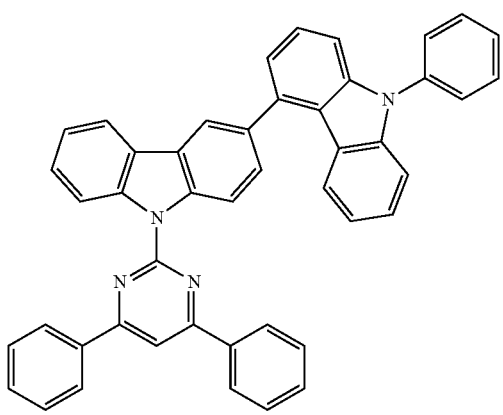
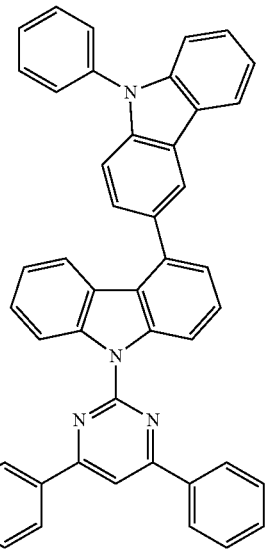
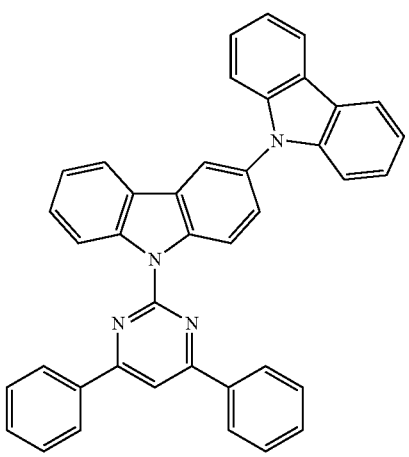

-continued
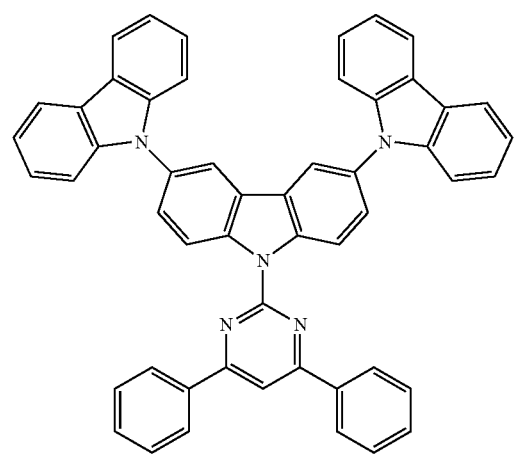
[Chemical Formula 84]
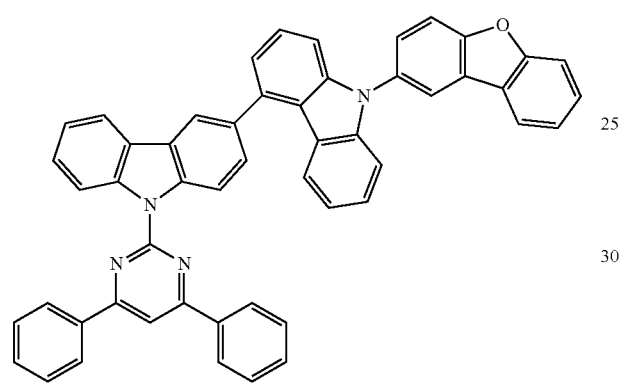
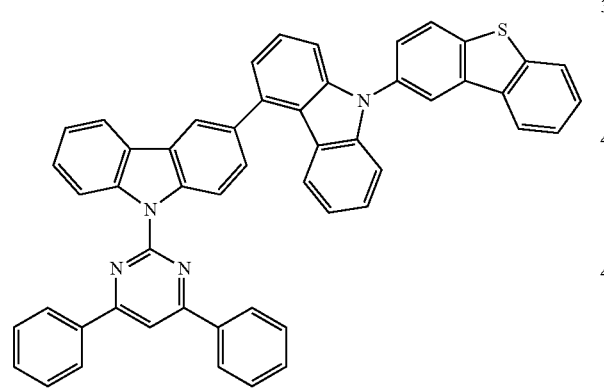
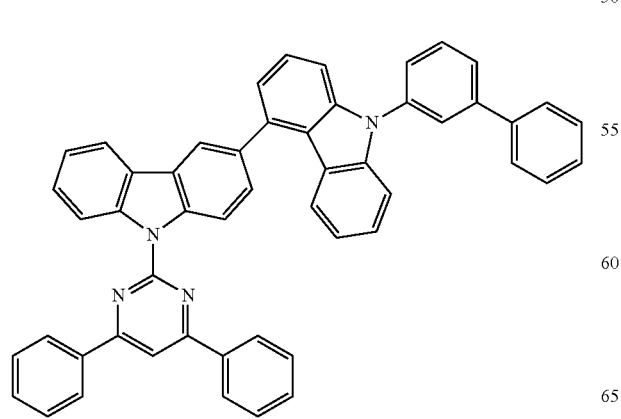
-continued
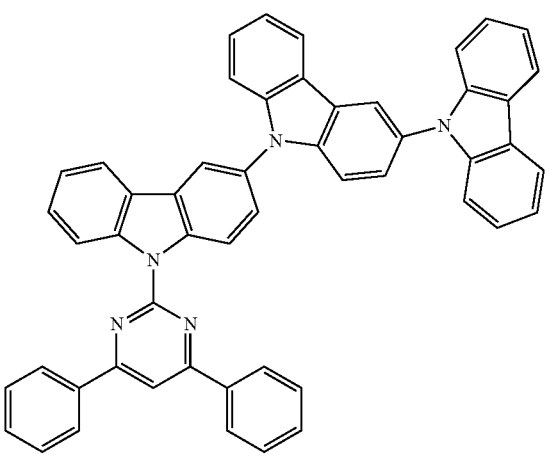
[Chemical Formula 85]
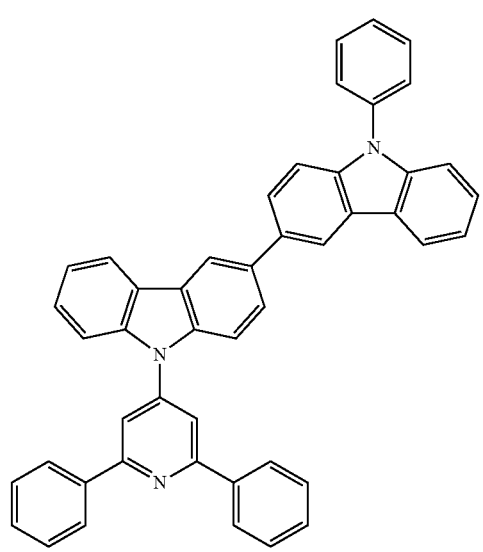
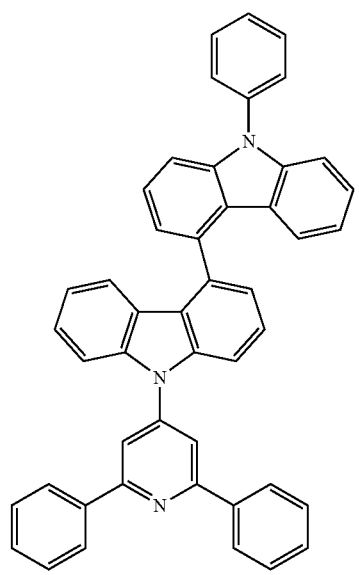

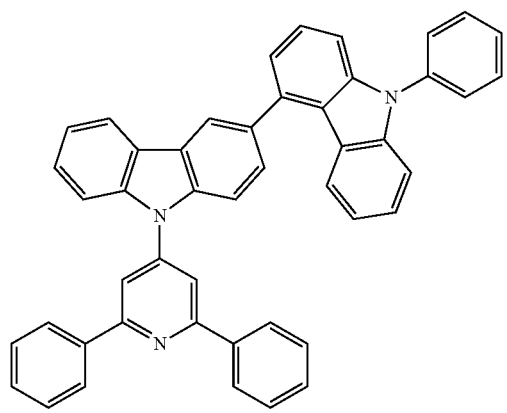
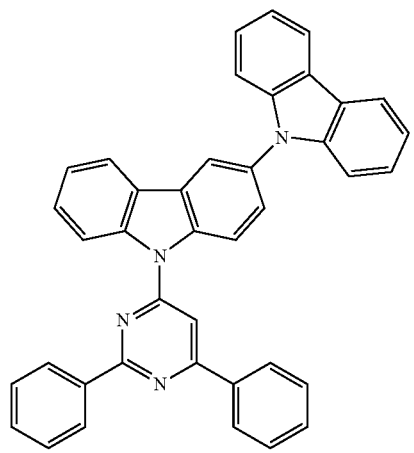
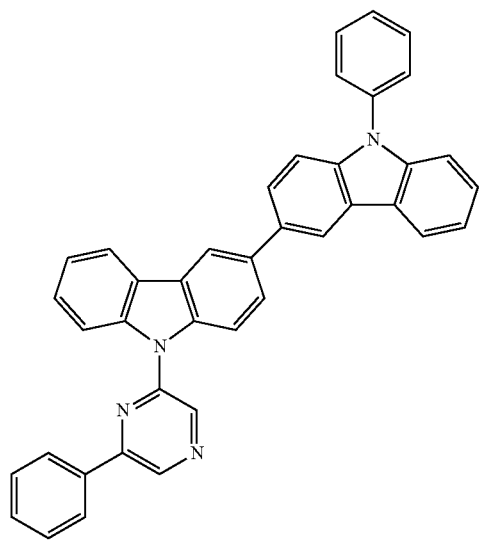
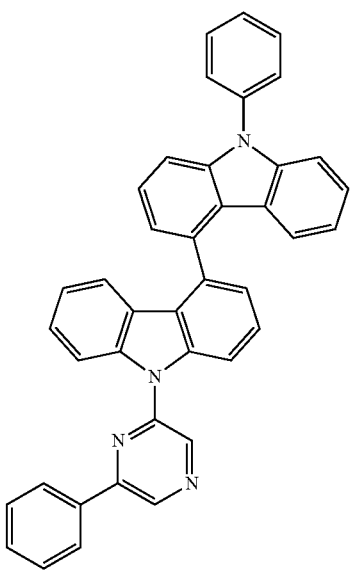
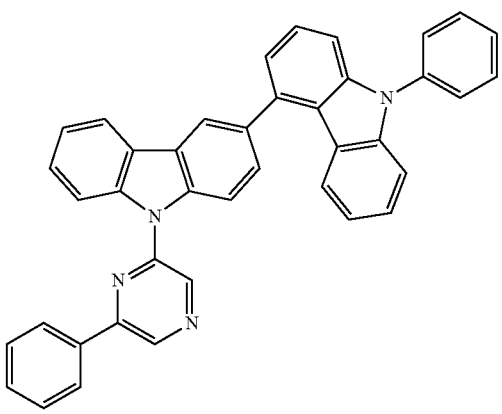
[Chemical Formula 86]
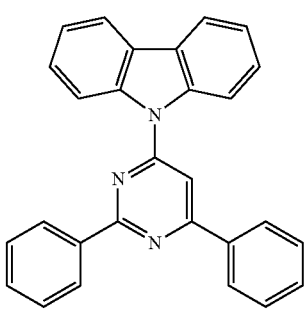

89
-continued
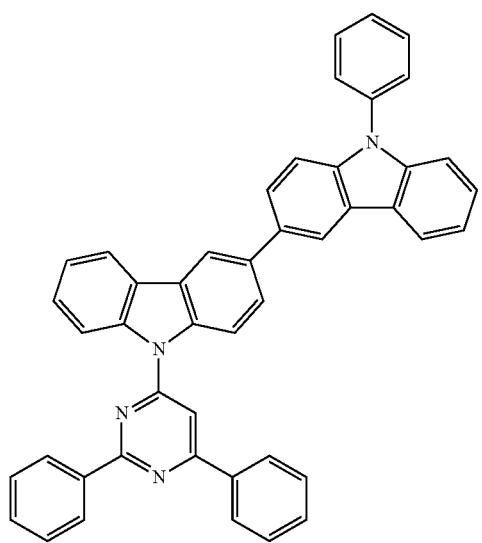
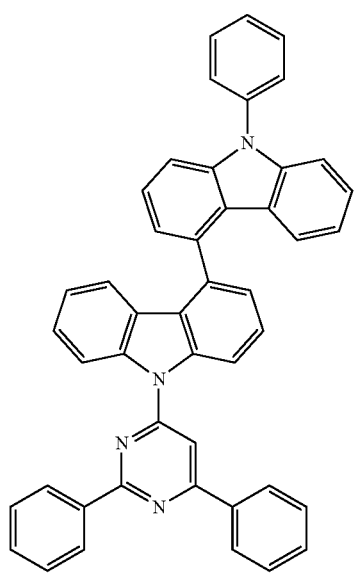
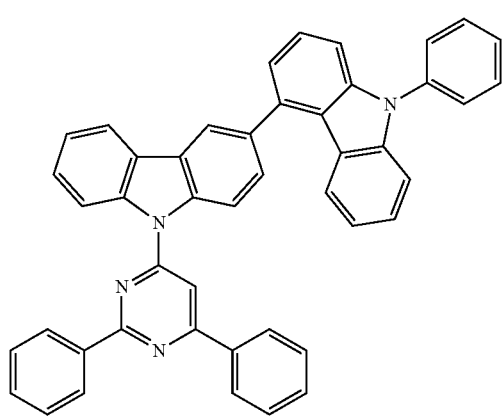
90
-continued
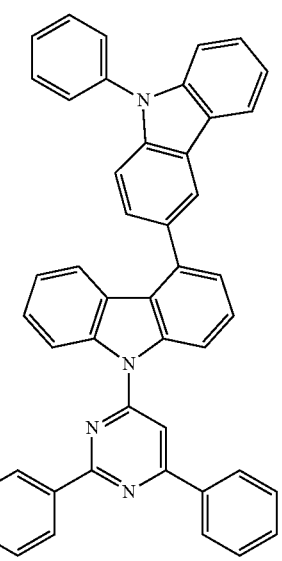
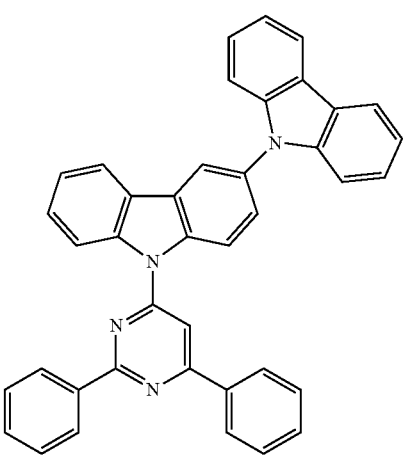

-continued

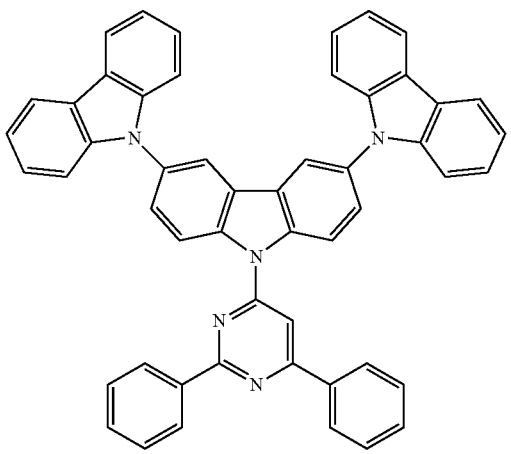

[Chemical Formula 87]

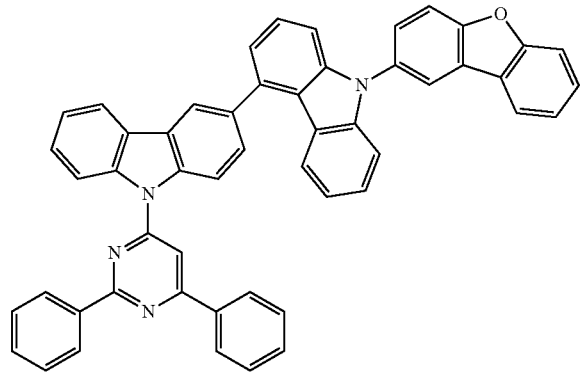

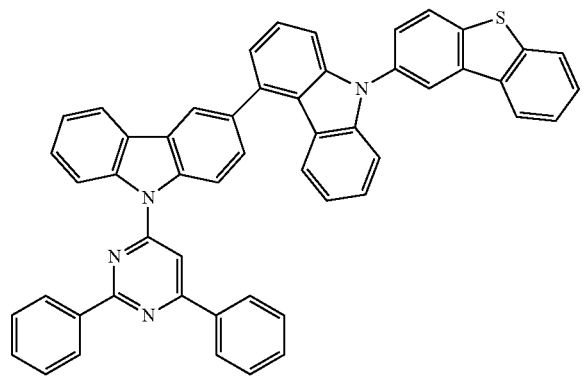

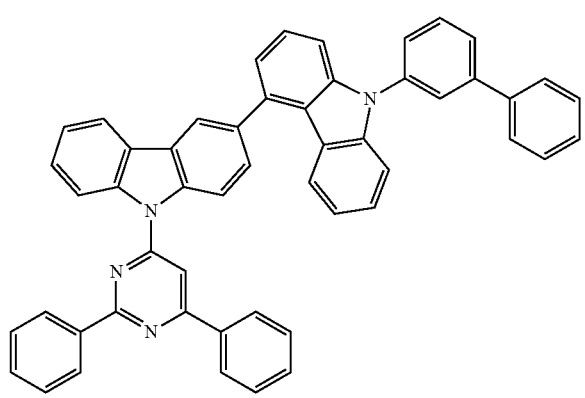

-continued

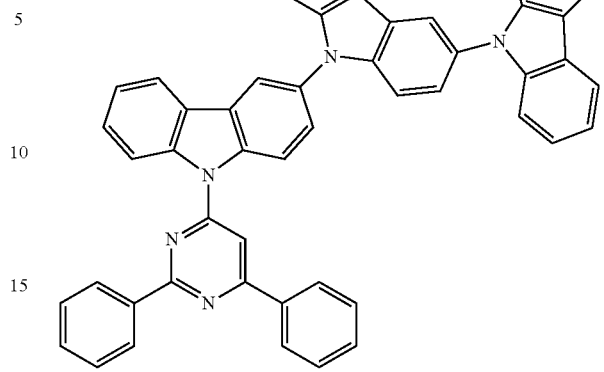

Content Ratio of Compounds in Emitting Layer

In the emitting layer 5 of the organic EL device 1 of the first exemplary embodiment, a content ratio of the first compound preferably ranges from 10 mass % to 80 mass %, more preferably from 20 mass % to 80 mass %, further preferably from 20 mass % to 60 mass %.

A content ratio of the second compound preferably ranges from 0.01 mass % to 10 mass %, more preferably from 0.01 mass % to 5 mass %, further preferably from 0.01 mass % to 1 mass %.

A content ratio of the third compound preferably ranges from 10 mass % to 80 mass %.

An upper limit of the total of the respective content ratios of the first, second and third compounds in the emitting layer 5 is 100 mass %. It should be noted that the emitting layer 5 of the exemplary embodiment may further contain another material in addition to the first, second and third compounds.

Film Thickness of Emitting Layer A film thickness of the emitting layer 5 of the organic EL device 1 of the first exemplary embodiment preferably ranges from 5 nm to 50 nm, more preferably from 7 nm to 50 nm, further preferably from 10 nm to 50 nm. When the film thickness of the emitting layer 5 is 5 nm or more, the emitting layer 5 is easily formed and chromaticity thereof is easily adjusted. When the film thickness of the emitting layer 5 is 50 nm or less, an increase in the drive voltage can be reduced.

Figure 4:
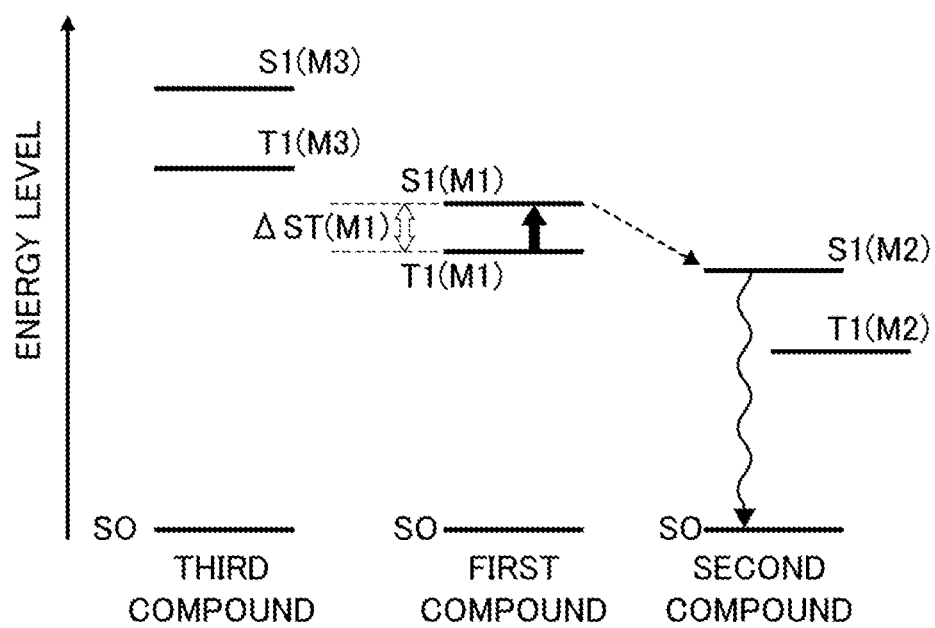
FIG. 4 shows a relationship between energy level and energy transfer in each of a first compound, a second compound and a third compound in an emitting layer.

FIG. 4 shows an example of a relationship between energy levels of the first, second and third compounds in the emitting layer. In FIG. 4, S0 represents a ground state. S1(M1) represents a lowest singlet state of the first compound and T1(M1) represents a lowest triplet state of the first compound. S1(M2) represents a lowest singlet state of the second compound and T1(M2) represents a lowest triplet state of the second compound. S1(M3) represents a lowest singlet state of the third compound and T1(M3) represents a lowest triplet state of the third compound. A dashed arrow directed from S1(M1) to S1(M2) in FIG. 4 represents Förster energy transfer from the lowest singlet state of the first compound to the second compound.

As shown in FIG. 4, when a compound having a small AST(M1) is used as the first compound, inverse intersystem crossing from the lowest triplet state T1(M1) to the lowest singlet state S1(M1) can be caused by a heat energy. Consequently, Förster energy transfer from the lowest singlet state S1(M1) of the first compound to the second compound is caused to generate the lowest singlet state S1(M2). As a result, fluorescence from the lowest singlet state S1(M2) of the second compound can be observed. It is speculated that the internal quantum efficiency can be theoretically raised up to 100% also by using the delayed fluorescence based on the TADF mechanism.

Substrate

A substrate 2 is used as a support for the organic EL device 1. For instance, glass, quartz and plastics are usable for the substrate 2. A flexible substrate is also usable. The flexible substrate is a bendable substrate, which is exemplified by a plastic substrate. Examples of a material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vacuum deposition film is also usable.

Anode

Preferable examples of a material for the anode 3 formed on the substrate 2 include metal, an alloy, an electroconductive compound, and a mixture thereof, which have a large work function (specifically, 4.0 eV or more). Specific examples of the material for the anode include indium tin oxide (ITO), indium tin oxide containing silicon or silicon oxide, indium zinc oxide, tungsten oxide, indium oxide containing zinc oxide and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of these metal materials (e.g., titanium nitride) are usable.

The above materials are typically deposited as a film by sputtering. For instance, indium zinc oxide can be deposited as a film by sputtering using a target that is obtained by adding zinc oxide in a range from 1 mass % to 10 mass % to indium oxide. Moreover, for instance, indium oxide containing tungsten oxide and zinc oxide can be deposited as a film by sputtering using a target that is obtained by adding tungsten oxide in a range from 0.5 mass % to 5 mass % and zinc oxide in a range from 0.1 mass % to 1 mass % to indium oxide. In addition, vacuum deposition, coating, ink jet printing and spin coating may be used for forming a film.

Among the organic layers formed on the anode 3, the hole injecting layer 6 formed in contact with the anode 3 is formed using a composite material that facilitates injection of holes irrespective of the work function of the anode 3. Accordingly, a material usable as an electrode material (e.g., metal, alloy, an electrically conductive compound, a mixture thereof, and elements belonging to Groups 1 and 2 of the periodic table of the elements) is usable as the material for the anode 3.

The elements belonging to Groups 1 and 2 of the periodic table of the elements, which are materials having a small work function, a rare earth metal and alloy thereof are also usable as the material for the anode 3. The elements belonging to Group 1 of the periodic table of the elements are alkali metal. The elements belonging to Group 2 of the periodic table of the elements are alkaline earth metal. Examples of alkali metal are lithium (Li) and cesium (Cs). Examples of alkaline earth metal are magnesium (Mg), calcium (Ca), and strontium (Sr). Examples of the rare earth metal are europium (Eu) and ytterbium (Yb). Examples of the alloys including these metals are MgAg and AlLi.

It should be noted that vacuum deposition and sputtering are usable for forming the anode 3 using the alkali metal, alkaline earth metal and the alloy thereof. Further, when the anode is formed of silver paste and the like, coating, ink jet printing and the like are usable.

Hole Injecting Layer

The hole injecting layer 6 is a layer containing a substance exhibiting a high hole-injecting capability. Examples of the substance exhibiting a high hole-injecting capability include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Moreover, examples of the substance exhibiting a high hole-injecting capability further include: an aromatic amine compound, which is a low molecular organic compound, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN). Moreover, a polymer compound is also usable as the substance exhibiting a high hole-injecting capability. Examples of the polymer compound are an oligomer, dendrimer and polymer. Specific examples of the polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD). Furthermore, the examples of the polymer compound include a polymer compound added with an acid such as poly(3,4-ethylene dioxythiophene)/poly(styrene sulfonic acid) (PEDOT/PSS), and polyaniline/poly(styrene sulfonic acid) (PAni/PSS).

Hole Transporting Layer

The hole transporting layer 7 is a layer containing a substance exhibiting a high hole-transporting capability. For instance, an aromatic amine compound, carbazole derivative and anthracene derivative are usable for the hole transporting layer 7. Specific examples of the substance usable for the hole transporting layer 6 include an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ cm$^2$/(V·s) or more.

For the hole transporting layer 7, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A polymer compound such as poly(N-vinylcarbazole) (abbreviation: PVK) and poly(4-vinyltriphenylamine) (abbreviation: PVTPA) is also usable.

However, any substance exhibiting a hole-transporting capability higher than an electron transporting capability may be used in place of the above substances. A layer containing the substance exhibiting a high hole-transporting capability may be provided in the form of a single layer or a laminate of two or more layers of the above substance(s).

When two or more hole transporting layers are provided, one of the hole transporting layers containing a material having a larger energy gap is preferably provided closer to the emitting layer 5.

Electron Transporting Layer

The electron transporting layer 8 is a layer containing a substance exhibiting a high electron-transporting capability. As the electron transporting layer, 1) a metal complex such as an aluminum complex, beryllium complex and zinc complex, 2) a heteroaromatic compound such as an imidazole derivative, benzimidazole derivative, azine derivative, carbazole derivative, and phenanthroline derivative, and 3) a polymer compound are usable. Specifically, as a low molecular organic compound, the metal complex such as Alq, tris(4-methyl-8-quinolinolato)aluminum (abbreviation: Almq$_3$), bis(10-hydroxybenzo[h]quinolinato)beryllium (abbreviation: BeBq2), BAlq, Znq, ZnPBO, and ZnBTZ are usable. In addition to the metal complex, a hetero aromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methyl-benzooxazole-2-yl)stilbene (abbreviation: BzOs) is usable. In the first exemplary embodiments, a benzimidazole compound is suitably usable. The above-described substances mostly have an electron mobility of $10^{-6}$ cm$^2$/(V·s) or more. However, any substance exhibiting an electron-transporting capability higher than a hole-transporting capability may be used for the electron transporting layer 8 in place of the above substances. The electron transporting layer 8 may be provided in the form of a single layer or a laminate of two or more layers of the above substance(s).

Moreover, a polymer compound is also usable for the electron transporting layer 8. Examples of the polymer compound include poly[(9,9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy).

Electron Injecting Layer

The electron injecting layer 9 is a layer containing a substance exhibiting a high electron-injecting capability. For the electron injecting layer 9, an alkali metal, alkaline earth metal and a compound thereof such as lithium (Li), cesium (Cs), calcium (Ca), lithium fluoride (LiF), cesium fluoride (CsF), calcium fluoride (CaF2), and lithium oxide (LiOx) are usable. In addition, the alkali metal, alkaline earth metal or the compound thereof may be added to the substance exhibiting an electron transporting capability in use. Specifically, for instance, magnesium (Mg) added to Alq may be used. In this case, the electrons can be more efficiently injected from the cathode 4.

Alternatively, a composite material provided by mixing an organic compound with an electron donor may be used for the electron injecting layer 9. The composite material exhibits excellent electron injecting capability and electron transporting capability, since the electron donor generates electron in the organic compound. In this case, the organic compound is preferably a material exhibiting an excellent transforming performance for the generated electrons. Specifically, for instance, the above-described substance for the electron transporting layer 8 (e.g., the metal complex and heteroaromatic compound) is usable. The electron donor may be any substance exhibiting an electron donating performance to the organic compound. Specifically, an alkali metal, alkaline earth metal and a rare earth metal are preferable, examples of which include lithium, cesium, magnesium, calcium, erbium and ytterbium. Moreover, an alkali metal oxide or alkaline earth metal oxide is preferably used as the electron donor, examples of which include lithium oxide, calcium oxide, and barium oxide. Further, Lewis base such as magnesium oxide is also usable. Furthermore, tetrathiafulvalene (abbreviation: TTF) is also usable.

Cathode

For instance, a metal, an alloy, an electrically conductive compound and a mixture, which have a small work function, specifically, of 3.8 eV or less, are preferably usable as a material for the cathode 4. Specific examples of the material for the cathode include the elements belonging to Groups 1 and 2 of the periodic table of the elements, a rare earth metal and alloys thereof. The elements belonging to Group 1 of the periodic table of the elements are alkali metal. The elements belonging to Group 2 of the periodic table of the elements are alkaline earth metal. Examples of alkali metal include lithium (Li) and cesium (Cs). Examples of alkaline earth metal include magnesium (Mg), calcium (Ca), and strontium (Sr). Examples of the rare earth metal include europium (Eu) and ytterbium (Yb). Examples of the alloys containing these metals include MgAg and AlLi.

When the cathode 4 is formed of the alkali metal, alkaline earth metal and alloy thereof, vacuum deposition and sputtering are usable. Further, when the anode is formed of silver paste and the like, coating, ink jet printing and the like are usable.

When the electron injecting layer 9 is provided, various conductive materials such as Al, Ag, ITO, graphene, and indium tin oxide containing silicon or silicon oxide are usable for forming the cathode 4 irrespective of the magnitude of the work function. The conductive materials can be deposited as a film by sputtering, ink jet printing, spin coating and the like.

Layer Formation Method(s)

The method of forming each layer of the organic EL device 1 of the first exemplary embodiment is not subject to any limitations except for those specifically mentioned above and thus known methods such as dry film-formation method and wet film-formation method are applicable. Examples of the dry film-formation method include vacuum deposition, sputtering, plasma and ion plating. Examples of the wet film-formation method include spin coating, dipping, flow coating and ink-jet.

Film Thickness

The film thickness of each organic layer of the organic EL device 1 of the first exemplary embodiment is not subject to any limitations except for those specifically mentioned above. The thickness usually preferably ranges from several nanometers to 1 μm in order to cause less defects (e.g., a pin hole) and prevent efficiency degradation resulting from requiring a high voltage to be applied.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not counted in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming a ring and atom(s) in a substituent substituting the ring are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Respective hydrogen atoms bonded to carbon atoms of the pyridine ring or the quinazoline ring and atoms forming the substituents are not counted in the number of the ring atoms. When a fluorene ring is substituted by, for instance, a fluorene ring (e.g., a spirofluorene ring), the number of atoms of the fluorene ring as a substituent is not counted in the number of the ring atoms for the fluorene ring.

Next, each of the substituents represented by the above formulae will be described below.

Examples of the aryl group (occasionally referred to as aromatic hydrocarbon group) having 6 to 30 ring carbon atoms herein include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group herein preferably has 6 to 20 ring carbon atoms, more preferably 6 to 14 ring carbon atoms, further preferably 6 to 12 ring carbon atoms. Among the above examples of the aryl group, a phenyl group, biphenyl group, naphthyl group, phenanthryl group, terphenyl group and fluorenyl group are particularly preferable. For 1-fluorenyl group, 2-fluorenyl group, 3-fluorenyl group and 4-fluorenyl group, a carbon atom at a position 9 is preferably substituted by the substituted or unsubstituted alkyl group having 1 to 30 carbon atoms or an unsubstituted aryl group having 6 to 18 ring carbon atoms described herein.

The heteroaryl group (occasionally referred to as heterocyclic group, heteroaromatic ring group or aromatic heterocyclic group) having 5 to 30 ring atoms herein preferably contains an atom selected from the group consisting of nitrogen, sulfur, oxygen, silicon, selenium atom and germanium atom, more preferably an atom selected from the group consisting of nitrogen, sulfur, and oxygen.

Examples of the heterocyclic group having 5 to 30 ring atoms herein include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

The heterocyclic group herein preferably has 5 to 20 ring atoms, more preferably 5 to 14 ring atoms. Among the above examples of the heterocyclic group, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are particularly preferable. For 1-carbazolyl group, 2-carbazolyl group, 3-carbazolyl group and 4-carbazolyl group, a nitrogen atom at a position 9 is preferably substituted by a substituted or unsubstituted aryl group having 6 to 30 ring carbon atoms or a substituted or unsubstituted heterocyclic group having 5 to 30 ring atoms as defined herein.

The heterocyclic group herein may be a group derived from any one of moieties represented by formulae (XY-1) to (XY-18) below.

[Chemical Formula 88]

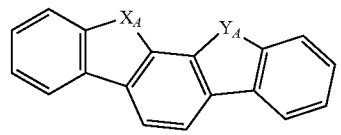

(XY-1)

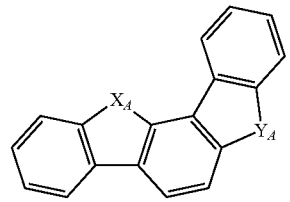

(XY-2)

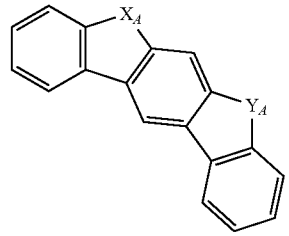

(XY-3)

(XY-4) 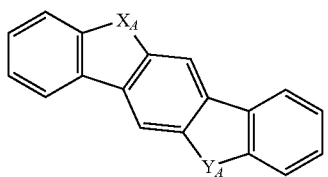

(XY-5) 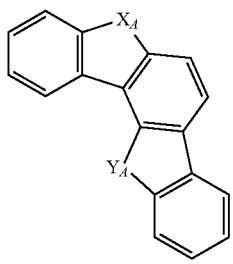

(XY-6) 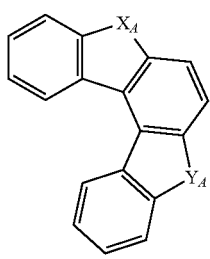

[Chemical Formula 89]

(XY-7) 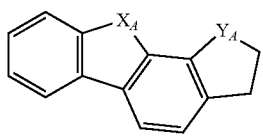

(XY-8) 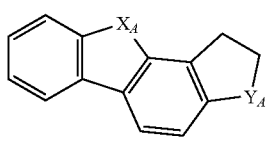

(XY-9) 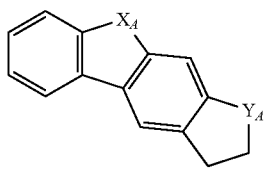

(XY-10) 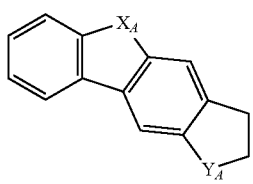

(XY-11) 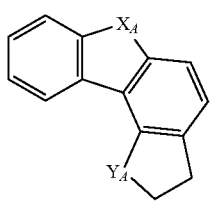

(XY-12) 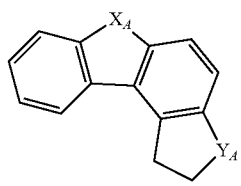

[Chemical Formula 90]

(XY-13) 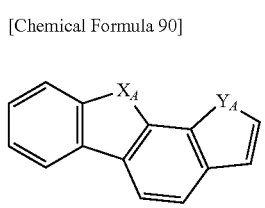

(XY-14) 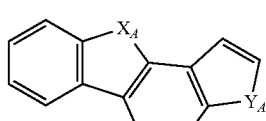

(XY-15) 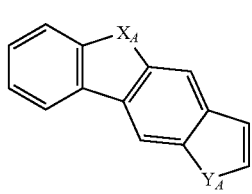

(XY-16) 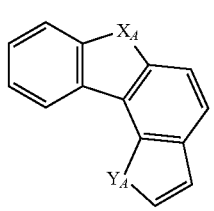

(XY-17) 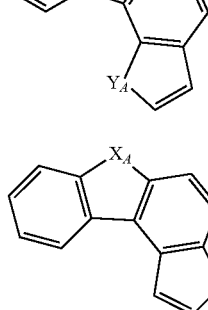

(XY-18) 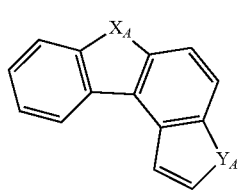

In the formulae (XY-1) to (XY-18), $X_A$ and $Y_A$ are each independently a hetero atom, preferably an oxygen atom, sulfur atom, selenium atom, silicon atom or germanium atom. The moieties represented by the formulae (XY-1) to (XY-18) may each be bonded in any position to be a heterocyclic group, which may be substituted.

The substituted or unsubstituted carbazolyl group herein may include a group in which a ring is further fused to a carbazole ring as represented by a formula below. Such a group may be substituted. The position of the bond may be changed as needed.

[Chemical Formula 91]

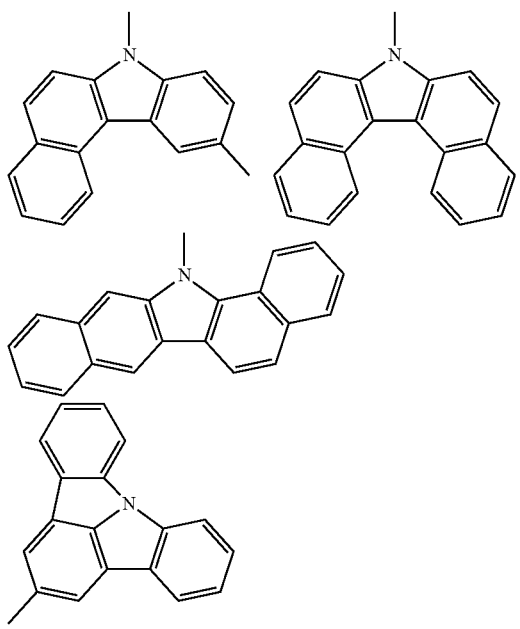

The alkyl group having 1 to 30 carbon atoms herein may be linear, branched or cyclic. Examples of the linear or branched alkyl group include a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neo-pentyl group, amyl group, isoamyl group, 1-methylpentyl group, 2-methylpentyl group, 1-pentylhexyl group, 1-butylpentyl group, 1-heptyloctyl group and 3-methylpentyl group.

The linear or branched alkyl group herein preferably has 1 to 10 carbon atoms, more preferably 1 to 6 carbon atoms. Among the examples of the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are further preferable.

Examples of the cycloalkyl group having 3 to 30 ring carbon atoms herein include a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the examples of the cycloalkyl group, a cyclopentyl group and a cyclohexyl group are further preferable.

A halogenated alkyl group provided by substituting an alkyl group with a halogen atom herein is exemplified by a group provided by substituting the above-described alkyl group having 1 to 30 carbon atoms with one or more halogen atoms. Specific examples of the halogenated alkyl group include a fluoromethyl group, difluoromethyl group, trifluoromethyl group, fluoroethyl group, trifluoromethylmethyl group, trifluoroethyl group and pentafluoroethyl group.

Examples of the substituted silyl group herein include an alkylsilyl group having 3 to 30 carbon atoms and an arylsilyl group having 6 to 30 ring carbon atoms.

The alkylsilyl group having 3 to 30 carbon atoms herein is exemplified by a trialkylsilyl group having the examples of the above-described alkyl group having 1 to 30 carbon atoms. Specific examples of the alkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group are mutually the same or different.

Examples of the arylsilyl group having 6 to 30 ring carbon atoms herein include a dialkylarylsilyl group, alkyldiarylsilyl group and triarylsilyl group.

The dialkylarylsilyl group is exemplified by a dialkylarylsilyl group having two of the examples of the above-described alkyl group having 1 to 30 carbon atoms and one of the examples of the above-described aryl group having 6 to 30 ring carbon atoms. The dialkylarylsilyl group preferably has 8 to 30 carbon atoms.

The alkyldiarylsilyl group is exemplified by an alkyldiarylsilyl group having one of the examples of the above-described alkyl group having 1 to 30 carbon atoms and two of the examples of the above-described aryl group having 6 to 30 ring carbon atoms. The dialkylarylsilyl group preferably has 13 to 30 carbon atoms.

The triarylsilyl group is exemplified by a triarylsilyl group having three of the examples of the above-described aryl group having 6 to 30 ring carbon atoms. The triarylsilyl group preferably has 18 to 30 carbon atoms.

An aryl group in the aralkyl group (occasionally referred to as arylalkyl group) herein may be an aromatic hydrocarbon group or a heterocyclic group.

The aralkyl group having 5 to 30 carbon atoms herein is preferably an aralkyl group having 6 to 30 ring carbon atoms and is represented by $-Z_3-Z_4$. $Z_3$ is exemplified by an alkylene group derived from the above-described alkyl group having 1 to 30 carbon atoms. $Z_4$ is exemplified by the above-described aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, 1-β-naphthylmethyl group, 1-β-naphthylethyl group, 2-β-naphthylethyl group, 1-β-naphthylisopropyl group, and 2-β-naphthylisopropyl group.

The substituted phosphoryl group herein is represented by a formula (P) below.

[Chemical Formula 92]

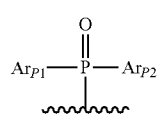

(P)

In the above formula (P), $Ar_{P1}$ and $Ar_{P2}$ are each independently a substituent, preferably a substituent selected from the group consisting of an alkyl group having 1 to 30 carbon atoms and an aryl group having 6 to 30 ring carbon atoms, more preferably a substituent selected from the group consisting of an alkyl group having 1 to 10 carbon atoms and an aryl group having 6 to 20 ring carbon atoms, further preferably a substituent selected from the group consisting of an alkyl group having 1 to 6 carbon atoms and an aryl group having 6 to 14 ring carbon atoms.

The alkoxy group having 1 to 30 carbon atoms herein is represented by —$OZ_1$. $Z_1$ is exemplified by the above-described alkyl group having 1 to 30 carbon atoms. Examples of the alkoxy group include a methoxy group, ethoxy group, propoxy group, butoxy group, pentyloxy group and hexyloxy group. The alkoxy group preferably has 1 to 20 carbon atoms.

A halogenated alkoxy group provided by substituting the alkoxy group with a halogen atom is exemplified by a group provided by substituting the above-described alkoxy group having 1 to 30 carbon atoms with one or more fluorine atoms.

An aryl group in the arylalkoxy group (occasionally referred to as aryloxy group) herein may be an aromatic hydrocarbon group or a heterocyclic group.

The arylalkoxy group having 5 to 30 carbon atoms herein is represented by —$OZ_2$. $Z_2$ is exemplified by the above-described aryl group having 6 to 30 ring carbon atoms. The arylalkoxy group preferably has 6 to 20 ring carbon atoms. This arylalkoxy group is exemplified by a phenoxy group.

The substituted amino group herein is represented by —$NHR_V$ or —$N(R_V)_2$. Examples of $R_V$ include the above-described alkyl group having 1 to 30 carbon atoms and the above-described aryl group having 6 to 30 ring carbon atoms. Examples of the substituted amino group include an alkylamino group and an arylamino group.

The alkenyl group having 2 to 30 carbon atoms herein may be linear or branched and examples thereof include a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

Examples of the cycloalkenyl group having 3 to 30 carbon atoms herein include a cyclopentadienyl group, cyclopentenyl group, cyclohexenyl group, and cyclohexadienyl group.

The alkynyl group having 2 to 30 carbon atoms herein may be linear or branched and examples thereof include ethynyl, propynyl, and 2-phenylethynyl.

Examples of the cycloalkynyl group having 3 to 30 carbon atoms include a cyclopentynyl group and cyclohexynyl group.

Examples of the substituted sulfanyl group herein include a methylsulfanyl group, phenylsulfanyl group, diphenylsulfanyl group, naphthylsulfanyl group, and triphenylsulfanyl group.

Examples of the substituted sulfinyl group herein include a methylsulfinyl group, phenylsulfinyl group, diphenylsulfinyl group, naphthylsulfinyl group, and triphenylsulfinyl group.

Examples of the substituted sulfonyl group herein include a methylsulfonyl group, phenylsulfonyl group, diphenylsulfonyl group, naphthylsulfonyl group, and triphenylsulfonyl group.

Examples of the substituted phosphanyl group herein include a phenylphosphanyl group.

Examples of the substituted carbonyl group herein include a methylcarbonyl group, phenylcarbonyl group, diphenylcarbonyl group, naphthylcarbonyl group, and triphenylcarbonyl group.

The alkoxycarbonyl group having 2 to 30 carbon atoms herein is represented by —COOY'. Y' is exemplified by the above-described alkyl group.

Examples of the substituted carboxy group herein include a benzoyloxy group.

The alkylthio group having 1 to 30 carbon atoms and the arylthio group having 6 to 30 ring carbon atoms herein are represented by —$SR_V$. Examples of $R_V$ include the above-described alkyl group having 1 to 30 carbon atoms and the above-described aryl group having 6 to 30 ring carbon atoms. The alkylthio group preferably has 1 to 20 carbon atoms and the arylthio group preferably has 6 to 20 ring carbon atoms.

Examples of the halogen atom herein include a fluorine atom, a chlorine atom, a bromine atom and an iodine atom, among which a fluorine atom is preferable.

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a hetero ring including a saturated ring, unsaturated ring, or aromatic ring.

The hydrogen atom herein includes isotopes having different numbers of neutrons, i.e., protium, deuterium and tritium.

The substituent meant by "substituted or unsubstituted" is at least one selected from the group consisting of an aryl group having 6 to 30 ring carbon atoms, a heteroaryl group having 5 to 30 ring atoms5, an alkyl group (a linear or branched alkyl group) having 1 to 30 carbon atoms, a cycloalkyl group having 3 to 30 ring carbon atoms, an alkyl halide group having 1 to 30 carbon atoms, an alkylsilyl group having 3 to 30 carbon atoms, an arylsilyl group having 6 to 30 ring carbon atoms, an alkoxy group having 1 to 30 carbon atoms, an aryloxy group having 5 to 30 carbon atoms, a substituted amino group, an alkylthio group having 1 to 30 carbon atoms, an arylthio group having 6 to 30 ring carbon atoms, an aralkyl group having 5 to 30 carbon atoms, an alkenyl group having 2 to 30 carbon atoms, an alkynyl group having 2 to 30 carbon atoms, a halogen atom, a cyano group, a hydroxyl group, a nitro group, and a carboxy group.

The substituent meant by "substituted or unsubstituted" herein is preferably at least one selected from the group consisting of an aryl group having 6 to 30 ring carbon atoms, a heteroaryl group having 5 to 30 ring atoms, an alkyl group (a linear or branched alkyl group) having 1 to 30 carbon atoms, a cycloalkyl group having 3 to 30 ring carbon atoms, an alkyl halide group having 1 to 30 carbon atoms, a halogen atom, an alkylsilyl group having 3 to 30 carbon atoms, an arylsilyl group having 6 to 30 ring carbon atoms, and a cyano group, more preferably the specific substituents referred to as being preferable in the explanation of the above-described substituents.

The substituent meant by "substituted or unsubstituted" herein may be further substituted by at least one group selected from the group consisting of an aryl group having 6 to 30 ring carbon atoms, a heteroaryl group having 5 to 30 ring atoms5, an alkyl group (a linear or branched alkyl group) having 1 to 30 carbon atoms, a cycloalkyl group having 3 to 30 ring carbon atoms, an alkyl halide group having 1 to 30 carbon atoms, an alkylsilyl group having 3 to 30 carbon atoms, an arylsilyl group having 6 to 30 ring carbon atoms, an alkoxy group having 1 to 30 carbon atoms, an aryloxy group having 5 to 30 carbon atoms, a substituted amino group, an alkylthio group having 1 to 30 carbon atoms, an arylthio group having 6 to 30 ring carbon atoms, an aralkyl group having 5 to 30 carbon atoms, an alkenyl group having 2 to 30 carbon atoms, an alkynyl group having 2 to 30 carbon atoms, a halogen atom, a cyano group, a hydroxyl group, a nitro group, and a carboxy group. In addition, plural ones of these substituents may be mutually bonded to form a ring.

When the substituent meant by "substituted or unsubstituted" is further substituted by a substituent, the substituent is preferably at least one selected from the group consisting of an aryl group having 6 to 30 ring carbon atoms, a heteroaryl group having 5 to 30 ring atoms, an alkyl group (a linear or branched alkyl group) having 1 to 30 carbon atoms, a halogen atom, and a cyano group, more preferably at least one selected from the specific substituents referred to as being preferable in the explanation of the above-described substituents.

The term "unsubstituted" used in "substituted or unsubstituted" means that a group is not substituted by the above-described substituents but bonded with a hydrogen atom.

"XX to YY carbon atoms" in the expression of "substituted or unsubstituted ZZ group having XX to YY carbon atoms" herein mean carbon atoms of an unsubstituted ZZ group and do not include carbon atoms of a substituent(s) of the substituted ZZ group.

"XX to YY atoms" in the expression of "substituted or unsubstituted ZZ group having XX to YY atoms" herein mean atoms of an unsubstituted ZZ group and does not include atoms of a substituent(s) of the substituted ZZ group.

The above also applies to the expression "substituted or unsubstituted" used for compounds or moieties thereof described below.

When substituents are mutually bonded to form a cyclic structure, the cyclic structure herein is a saturated ring, unsaturated ring, aromatic hydrocarbon ring, or a heterocyclic ring.

Examples of the aryl group and the like for the linking group herein include a divalent or multivalent group obtained by removing at least one atom from the above-described monovalent groups.

When the organic EL device 1 of the first exemplary embodiment emits light, it is preferable that the second compound in the emitting layer 5 mainly emits light.

The first exemplary embodiment can provide a high-performance organic electroluminescence device capable of emitting light in a wavelength range from blue to green.

Electronic Device

The organic EL device 1 of the first exemplary embodiments is usable in an electronic device such as a display and a light-emitting unit. Examples of the display include display components such as an organic EL panel module, TV, mobile phone, tablet, and personal computer. Examples of the light-emitting unit include an illuminator and a vehicle light.

MODIFICATION OF EMBODIMENT(S)

It should be noted that the invention is not limited to the above exemplary embodiment(s) but may include any modification and improvement as long as an object of the invention can be achieved.

For instance, the emitting layer is not limited to a single layer, but may be provided by laminating a plurality of emitting layers. When the organic EL device has the plurality of emitting layers, it is only required that at least one of the emitting layers satisfies the conditions described in the above exemplary embodiment. For instance, the rest of the emitting layers may be a fluorescent emitting layer or a phosphorescent emitting layer with use of emission caused by electron transfer from the triplet excited state directly to the ground state.

When the organic EL device includes the plurality of emitting layers, the plurality of emitting layers may be adjacent to each other, or be layered via an intermediate layer to provide a so-called tandem-type organic EL device.

For instance, a blocking layer may be in contact with at least one of an anode-side and a cathode-side of the emitting layer. The blocking layer preferably abuts on the emitting layer and blocks at least one of holes, electrons and excitons.

For instance, when the blocking layer is in contact with the cathode-side of the emitting layer, the blocking layer permits transport of electrons, but prevents holes from reaching a layer provided near the cathode (e.g., the electron transporting layer) beyond the blocking layer. When the organic EL device includes the electron transporting layer, the organic EL device preferably includes the blocking layer between the emitting layer and the electron transporting layer.

When the blocking layer is in contact with the emitting layer near the anode, the blocking layer permits transport of holes, but prevents electrons from reaching a layer provided near the anode (e.g., the hole transporting layer) beyond the blocking layer. When the organic EL device includes the hole transporting layer, the organic EL device preferably includes the blocking layer between the emitting layer and the hole transporting layer.

Moreover, the blocking layer may abut on the emitting layer so that excited energy does not leak out from the emitting layer toward neighboring layer(s). Accordingly, the blocking layer blocks excitons generated in the emitting layer from transferring to a layer(s) (e.g., the electron transporting layer and the hole transporting layer) closer to the electrode(s) beyond the blocking layer.

The emitting layer and the blocking layer preferably abut on each other.

Specific structures and shapes of the components according to the invention may be altered in any manner as long as an object of the invention can be achieved.

EXAMPLE(S)

Examples of the invention will be described below. However, the invention is by no means limited to Examples.

Compounds used for manufacturing the organic EL device will be shown below.

[Chemical Formula 93]

HI

-continued
HT1
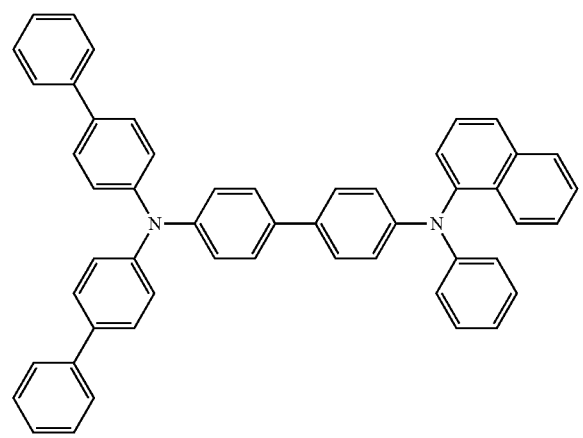
[Chemical Formula 94]
HT2
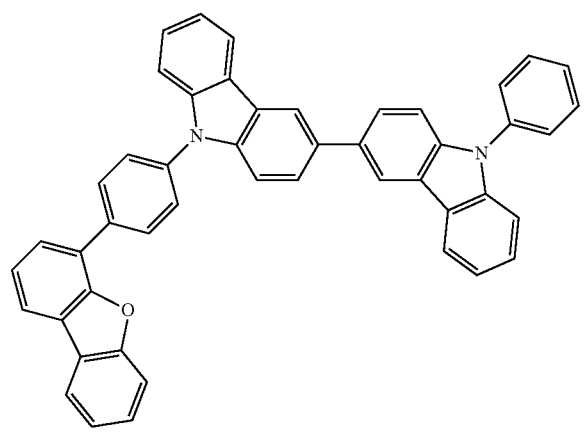
mCP
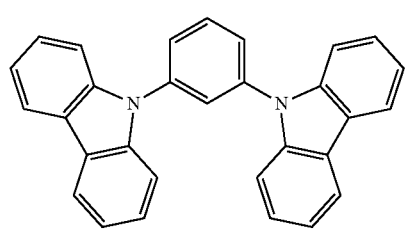
HB
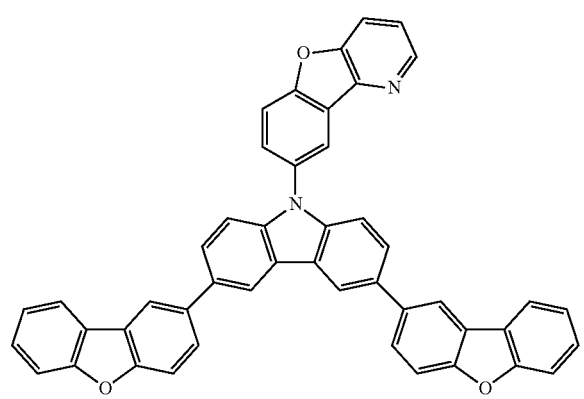
-continued
ET
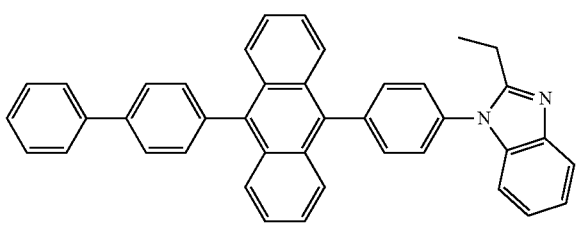
[Chemical Formula 95]
BD
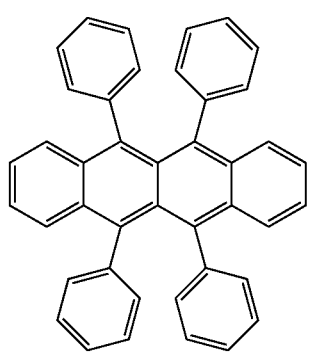
YD
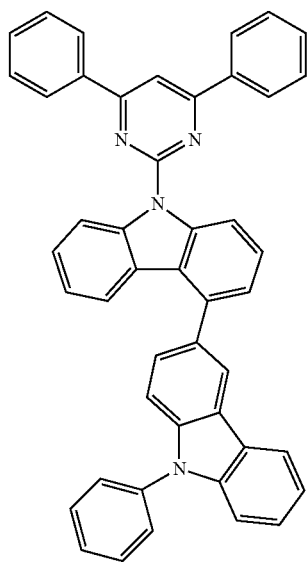
[Chemical Formula 96]
CH1

CH2

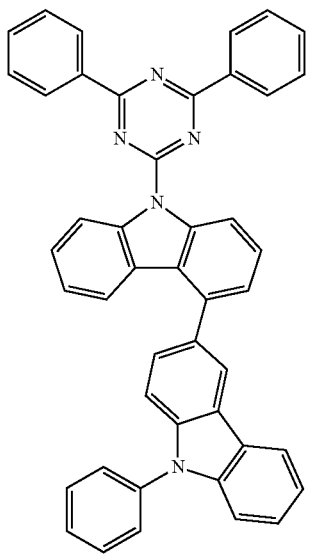

[Chemical Formula 97]

CH3

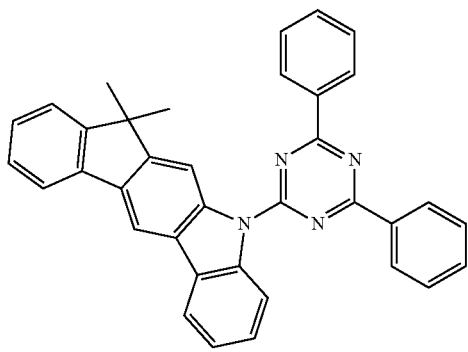

CH4

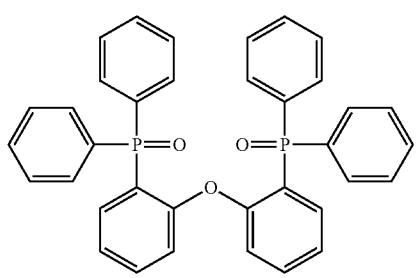

DPEPO

[Chemical Formula 98]

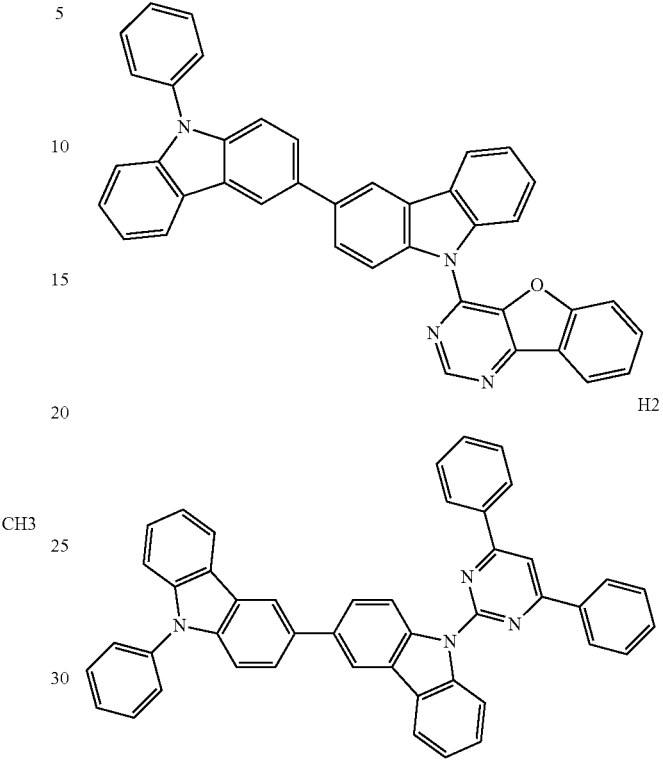

Evaluation of Compounds

The properties of compounds were measured by the following methods.

Delayed Fluorescence

Delayed fluorescence was checked by measuring transitional PL using the device shown in FIG. 2. A sample was prepared by co-depositing the compounds H1 and TH-2 on a quartz substrate at a ratio of the compound H1 of 12 mass % to form a 100-nm-thick thin film. The compound H1 allows for Prompt emission, which is observed immediately when the excited state is achieved by exciting the compound H1 with pulsed light (i.e., light emitted from the pulse laser unit) having a wavelength absorbable into the compound H1, and Delay emission, which is observed not immediately upon the excitation but after a while. The delayed fluorescence in Examples means that an amount of Delay emission is 5% or more with respect to an amount of Prompt emission. Specifically, when the amount of Prompt emission is denoted by $X_P$ and the amount of Delay emission is denoted by $X_D$, a value of $X_D/X_P$ is 0.05 or more.

The compound H1 has proven to achieve the amount of Delay emission of 5% or more with respect to the amount of Prompt emission. Specifically, the compound H1 has proven to achieve a value of $X_D/X_P$ of 0.05 or more.

The compound H2 was also measured in terms of transient PL in the same manner as the compound H1 and has proven to be a delayed fluorescent compound.

The respective amounts of Prompt emission and Delay emission can be determined by the same method as described in "Nature 492, 234-238, 2012." It should be noted that a device used for calculating the respective amounts of Prompt emission and Delay emission is not limited to the device of FIG. 2 and a device described in the above literature.

Singlet Energy $S_1$

A singlet energy $S_1$ of each of the compound CH1, compound CH2, compound CH3, compound CH4, compound H1, and compound H2 was measured by the above-described thin-film method.

A singlet energy $S_1$ of the compound BD was measured by the above-described solution method.

Table 3 shows measurement results.

TABLE 3

| Compound | Singlet Energy [eV] |
| --- | --- |
| CH1 | 3.15 |
| CH2 | 3.13 |
| CH3 | 3.10 |
| CH4 | 3.04 |
| H1 | 2.94 |
| H2 | 3.00 |
| BD | 2.75 |

Main Peak Wavelength of Compound

A toluene solution in which the compound BD was dissolved at a concentration ranging from $10^{-6}$ mol/l or more to $10^{-5}$ mol/l or less was prepared and a luminescence spectrum of the toluene solution was measured. In the luminescence spectrum, a peak wavelength at which the luminous intensity was maximized was defined as a main peak wavelength. The main peak wavelength of the compound BD was 449 nm.

Preparation and Evaluation of Organic EL Device

Organic EL devices were prepared and evaluated as follows.

Example 1

A glass substrate (size: 25 mm×75 mm×1.1 mm-thickness, manufactured by Geomatec Co., Ltd.) having an ITO transparent electrode (anode) was ultrasonic-cleaned in isopropyl alcohol for five minutes. After being ultrasonic-cleaned, the glass substrate was UV/ozone-cleaned for 30 minutes. A film of ITO was set to be 130-nm thick.

The thus-cleaned glass substrate was mounted on a substrate holder of a vacuum evaporation apparatus. Initially, the compound HI was vapor-deposited on a surface of the glass substrate where the transparent electrode line was provided in a manner to cover the transparent electrode, thereby forming a 5-nm-thick hole injecting layer.

The compound HT1 was then vapor-deposited on the hole injecting layer to form an 80-nm-thick first hole transporting layer.

The compound HT2 was then vapor-deposited on the first hole transporting layer to form a 10-nm-thick second hole transporting layer.

The compound mCP was then vapor-deposited on the second hole transporting layer to form a 5-nm-thick electron blocking layer.

The compound H1 (first compound) and the compound BD (second compound), and the compound CH1 (third compound) were then co-deposited on the electron blocking layer to form a 25-nm-thick emitting layer. The concentration of the compound BD was set at 1 mass %, the concentration of the compound H1 was set at 24 mass %, and the concentration of the compound CH1 was set at 75 mass % in the emitting layer.

The compound HB was then vapor-deposited on the emitting layer to form a 5-nm-thick hole blocking layer.

The compound ET was then vapor-deposited on the hole blocking layer to form a 20-nm-thick electron transporting layer.

Lithium fluoride (LiF) was then vapor-deposited on the electron transporting layer to form a 1-nm-thick electron injecting electrode (cathode).

A metal aluminum (Al) was then vapor-deposited on the electron injecting electrode to form an 80-nm-thick metal $A_1$ cathode.

A device arrangement of the organic EL device of Example 1 is roughly shown as follows.

ITO(130)/HI(5)/HT1(80)/HT2(10)/mCP(5)/CH1: H1: BD (25, 24%, 1%)/HB(5)/ET(20)/LiF(1)/Al(80)

Numerals in parentheses mean film thicknesses (unit: nm). A first percentage in parentheses is a ratio (mass %) of the first compound in the emitting layer and a second percentage in the parentheses is a ratio (mass %) of the second compound.

Example 2

An organic EL device of Example 2 was prepared in the same manner as the organic EL device of Example 1 except that the compound CH1 in the emitting layer of Example 1 was replaced with the compound CH2.

A device arrangement of the organic EL device of Example 2 is roughly shown as follows.

ITO(130)/HI(5)/HT1(80)/HT2(10)/mCP(5)/CH2: H1: BD (25, 24%, 1%)/HB(5)/ET(20)/LiF(1)/Al(80)

Example 3

An organic EL device of Example 3 was prepared in the same manner as the organic EL device of Example 1 except that the compound CH1 in the emitting layer of Example 1 was replaced with the compound CH3.

A device arrangement of the organic EL device of Example 3 is roughly shown as follows.

ITO(130)/HI(5)/HT1(80)/HT2(10)/mCP(5)/CH3: H1: BD (25, 24%, 1%)/HB(5)/ET(20)/LiF(1)/Al(80)

Comparative Example 1

An organic EL device of Comparative Example 1 was prepared in the same manner as the organic EL device of Example 1 except that the compound CH1 in the emitting layer of Example 1 was replaced with the compound DPEPO.

A device arrangement of the organic EL device of Comparative Example 1 is roughly shown as follows.

ITO(130)/HI(5)/HT1 (80)/HT2(10)/mCP(5)/DPEPO: H1:BD(25, 24%, 1%)/HB(5)/ET(20)/LiF(1)/Al(80)

Evaluation of Organic EL Device(s)

The prepared organic EL devices were evaluated as follows. Table 4 shows the evaluation results.

Drive Voltage

A voltage (unit: V) allowing current to run between the ITO transparent electrode and the metal $A_1$ cathode at a current density of 0.1 mA/cm² was measured.

CIE1931 Chromaticity, Main Peak Wavelength λp

Voltage was applied on each of the organic EL devices such that a current density was 0.1 mA/cm² and coordinates (x, y) of CIE1931 chromaticity were measured by a spectroradiometer (CS-1000 manufactured by Konica Minolta, Inc.). The main peak wavelength λp was determined from the obtained spectral radiance spectra.

External Quantum Efficiency, EQE

Voltage was applied on each of the organic EL devices such that a current density was 0.1 mA/cm² and spectral radiance spectra were measured by a spectroradiometer (CS-1000 manufactured by Konica Minolta, Inc.). The external quantum efficiency EQE (unit: %) was calculated from the obtained spectral-radiance spectra, assuming that the spectra were provided under Lambertian radiation.

Lifetime LT50

A continuous current test under direct current was performed with an initial current density of 10 mA/cm² and time expired before the luminance dropped to 50% of the initial level at the start of the test was determined as a lifetime (LT50).

TABLE 4

|  | First Compound | Second Compound | Third Compound | Voltage [V] | CIEx | CIEy | EQE [%] | λp [nm] | LT50 [hrs] |
| --- | --- | --- | --- | --- | --- | --- | --- | --- | --- |
| EX. 1 | H1 | BD | CH1 | 3.1 | 0.154 | 0.155 | 9.4 | 453 | 7 |
| EX. 2 | H1 | BD | CH2 | 3.1 | 0.151 | 0.141 | 10.5 | 453 | 6 |
| EX. 3 | H1 | BD | CH3 | 3.1 | 0.151 | 0.141 | 10.5 | 453 | 9 |
| Comp. 1 | H1 | BD | DPEPO | 3.2 | 0.153 | 0.147 | 10.1 | 451 | 0.5 |

Each of the organic EL devices of Examples 1 to 3 emitted blue light, had a long life as compared with the organic EL device of Comparative Example 1, and achieved a high luminous efficiency comparable to that of the organic EL device of Comparative Example 1.

Example 4

An organic EL device of Example 4 was prepared in the same manner as the organic EL device of Example 1 except that the compound H1 in the emitting layer of Example 1 was replaced with the compound H2.

A device arrangement of the organic EL device of Example 4 is roughly shown as follows.

ITO(130)/HI(5)/HT1(80)/HT2(10)/mCP(5)/CH1: H2: BD (25, 24%, 1%)/HB(5)/ET(20)/LiF(1)/Al(80)

Example 5

An organic EL device of Example 5 was prepared in the same manner as the organic EL device of Example 2 except that the compound H1 in the emitting layer of Example 2 was replaced with the compound H2.

A device arrangement of the organic EL device of Example 5 is roughly shown as follows.

ITO(130)/HI(5)/HT1(80)/HT2(10)/mCP(5)/CH2: H2: BD (25, 24%, 1%)/HB(5)/ET(20)/LiF(1)/Al(80)

Comparative Example 2

An organic EL device of Comparative Example 2 was prepared in the same manner as the organic EL device of Comparative Example 1 except that the compound H1 in the emitting layer of Comparative Example 1 was replaced with the compound H2.

A device arrangement of the organic EL device of Comparative Example 2 is roughly shown as follows.

ITO(130)/HI(5)/HT1(80)/HT2(10)/mCP(5)/DPEPO: H2: BD (25, 24%, 1%)/HB(5)/ET(20)/LiF(1)/Al(80)

Evaluation of Organic EL Device(s)

The prepared organic EL devices were evaluated in the same manner as described above. Table 5 shows the evaluation results.

TABLE 5

|  | First Compound | Second Compound | Third Compound | Voltage [V] | CIEx | CIEy | EQE [%] | λp [nm] | LT50 [hrs] |
| --- | --- | --- | --- | --- | --- | --- | --- | --- | --- |
| Ex. 4 | H2 | BD | CH1 | 3.5 | 0.165 | 0.165 | 10.3 | 454 | 18 |
| Ex. 5 | H2 | BD | CH2 | 3.4 | 0.165 | 0.169 | 9.1 | 453 | 13 |
| Comp. 2 | H2 | BD | DPEPO | 3.4 | 0.166 | 0.152 | 10.1 | 451 | 0.5 |

Each of the organic EL devices of Examples 4 to 5 emitted blue light, had a long life as compared with the organic EL device of Comparative Example 2, and achieved a high luminous efficiency comparable to that of the organic EL device of Comparative Example 2.

Example 6

An organic EL device of Example 6 was prepared in the same manner as the organic EL device of Example 1 except that the concentration of the compound BD was set at 1 mass %, the concentration of the compound H1 was set at 49 mass % and the concentration of the compound CH1 was set at 50 mass % in the emitting layer of Example 1.

A device arrangement of the organic EL device of Example 6 is roughly shown as follows.

ITO(130)/HI(5)/HT1(80)/HT2(10)/mCP(5)/CH1: H1: BD (25, 49%, 1%)/HB(5)/ET(20)/LiF(1)/Al(80)

Example 7

An organic EL device of Example 7 was prepared in the same manner as the organic EL device of Example 6 except that the compound CH1 in the emitting layer of Example 6 was replaced with the compound CH2.

A device arrangement of the organic EL device of Example 7 is roughly shown as follows.

ITO(130)/HI(5)/HT1(80)/HT2(10)/mCP(5)/CH2: H1: BD (25, 49%, 1%)/HB(5)/ET(20)/LiF(1)/Al(80)

Example 8

An organic EL device of Example 8 was prepared in the same manner as the organic EL device of Example 6 except that the compound CH1 in the emitting layer of Example 6 was replaced with the compound CH3.

A device arrangement of the organic EL device of Example 8 is roughly shown as follows.

ITO(130)/HI(5)/HT1(80)/HT2(10)/mCP(5)/CH3: H1: BD (25, 49%, 1%)/HB(5)/ET(20)/LiF(1)/Al(80)

Comparative Example 3

An organic EL device of Comparative Example 3 was prepared in the same manner as the organic EL device of Example 6 except that the compound CH1 in the emitting layer of Example 6 was replaced with the compound DPEPO.

A device arrangement of the organic EL device of Comparative Example 3 is roughly shown as follows.

ITO(130)/HI(5)/HT1(80)/HT2(10)/mCP(5)/DPEPO: H1: BD (25, 49%, 1%)/HB(5)/ET(20)/LiF(1)/Al(80)

Evaluation of Organic EL Device(s)

The prepared organic EL devices were evaluated in the same manner as described above. Table 6 shows the evaluation results.

Each of the organic EL devices of Examples 6 to 8 emitted blue light, had a long life as compared with the organic EL device of Comparative Example 3, and achieved a high luminous efficiency comparable to that of the organic EL device of Comparative Example 3.

Example 9

An organic EL device of Example 9 was prepared in the same manner as the organic EL device of Example 6 except that the compound H1 in the emitting layer of Example 6 was replaced with the compound H2.

A device arrangement of the organic EL device of Example 9 is roughly shown as follows.

ITO(130)/HI(5)/HT1(80)/HT2(10)/mCP(5)/CH1: H2: BD (25, 49%, 1%)/HB(5)/ET(20)/LiF(1)/Al(80)

Example 10

An organic EL device of Example 10 was prepared in the same manner as the organic EL device of Example 7 except that the compound H1 in the emitting layer of Example 7 was replaced with the compound H2.

A device arrangement of the organic EL device of Example 10 is roughly shown as follows.

ITO(130)/HI(5)/HT1(80)/HT2(10)/mCP(5)/CH2: H2: BD (25, 49%, 1%)/HB(5)/ET(20)/LiF(1)/Al(80)

Comparative Example 4

An organic EL device of Comparative Example 4 was prepared in the same manner as the organic EL device of Comparative Example 3 except that the compound H1 in the emitting layer of Comparative Example 3 was replaced with the compound H2.

A device arrangement of the organic EL device of Comparative Example 4 is roughly shown as follows.

ITO(130)/HI(5)/HT1(80)/HT2(10)/mCP(5)/DPEPO: H2: BD (25, 49%, 1%)/HB(5)/ET(20)/LiF(1)/Al(80)

Evaluation of Organic EL Device(s)

The prepared organic EL devices were evaluated in the same manner as described above. Table 7 shows the evaluation results.

TABLE 6

| | First Compound | Second Compound | Third Compound | Voltage [V] | CIEx | CIEy | EQE [%] | $\lambda_p$ [nm] | LT50 [hrs] |
|---|---|---|---|---|---|---|---|---|---|
| Ex. 6 | H1 | BD | CH1 | 2.9 | 0.160 | 0.174 | 9.1 | 454 | 7 |
| Ex. 7 | H1 | BD | CH2 | 2.9 | 0.161 | 0.174 | 9.3 | 453 | 9.5 |
| Ex. 8 | H1 | BD | CH3 | 2.9 | 0.161 | 0.174 | 9.3 | 453 | 9 |
| Comp. 3 | H1 | BD | DPEPO | 2.9 | 0.162 | 0.182 | 10.3 | 452 | 0.5 |

TABLE 7

| | First Compound | Second Compound | Third Compound | Voltage [V] | CIEx | CIEy | EQE [%] | $\lambda_p$ [nm] | LT50 [hrs] |
|---|---|---|---|---|---|---|---|---|---|
| Ex. 9 | H2 | BD | CH1 | 3.4 | 0.178 | 0.193 | 10.6 | 454 | 24 |
| Ex. 10 | H2 | BD | CH2 | 3.3 | 0.182 | 0.208 | 10.1 | 453 | 21 |
| Comp. 4 | H2 | BD | DPEPO | 3.1 | 0.179 | 0.184 | 9.3 | 452 | 0.5 |

Each of the organic EL devices of Examples 9 to 10 emitted blue light, had a long life as compared with the organic EL device of Comparative Example 4, and achieved a high luminous efficiency comparable to that of the organic EL device of Comparative Example 4.

Example 11

An organic EL device of Example 11 was prepared in the same manner as the organic EL device of Example 1 except that the compound CH1 in the emitting layer of Example 1 was replaced with the compound CH4.

A device arrangement of the organic EL device of Example 11 is roughly shown as follows.

ITO(130)/HI(5)/HT1(80)/HT2(10)/mCP(5)/CH4: H1: BD (25, 24%, 1%)/HB(5)/ET(20)/LiF(1)/Al(80)

Evaluation of Organic EL Device(s)

The prepared organic EL device was evaluated in the same manner as described above. Table 8 shows the evaluation results.

TABLE 8

| | First Compound | Second Compound | Third Compound | Voltage [V] | CIEx | CIEy | $\lambda_p$ [nm] | LT50 [hrs] |
|---|---|---|---|---|---|---|---|---|
| Ex. 11 | H1 | BD | CH4 | 3.0 | 0.170 | 0.206 | 453 | 7.5 |

The organic EL device of Example 11 emitted blue light and had a long life as compared with the organic EL devices of Comparative Examples 1 to 4.

Comparative Example 5

An organic EL device of Comparative Example 5 was prepared in the same manner as the organic EL device of Example 11 except that the compound BD in the emitting layer of Example 11 was replaced with the compound YD.

A device arrangement of the organic EL device of Comparative Example 5 is roughly shown as follows.

ITO(130)/HI(5)/HT1(80)/HT2(10)/mCP(5)/CH4: H1: YD (25, 24%, 1%)/HB(5)/ET(20)/LiF(1)/Al(80)

Comparative Example 6

An organic EL device of Comparative Example 6 was prepared in the same manner as the organic EL device of Comparative Example 5 except that the compound CH4 in the emitting layer of Comparative Example 5 was replaced with the compound CH1.

A device arrangement of the organic EL device of Comparative Example 6 is roughly shown as follows.

ITO(130)/HI(5)/HT1(80)/HT2(10)/mCP(5)/CH1: H1: YD (25, 24%, 1%)/HB(5)/ET(20)/LiF(1)/Al(80)

Comparative Example 7

An organic EL device of Comparative Example 7 was prepared in the same manner as the organic EL device of Comparative Example 5 except that the compound CH4 in the emitting layer of Comparative Example 5 was replaced with the compound CH2.

A device arrangement of the organic EL device of Comparative Example 7 is roughly shown as follows.

ITO(130)/HI(5)/HT1(80)/HT2(10)/mCP(5)/CH2: H1: YD (25, 24%, 1%)/HB(5)/ET(20)/LiF(1)/Al(80)

Evaluation of Organic EL Device(s)

A main peak wavelength $\lambda_p$ of each of the prepared organic EL devices was evaluated in the same manner as described above. Table 9 shows the evaluation results.

TABLE 9

| | First Compound | Second Compound | Third Compound | $\lambda_p$ [nm] |
|---|---|---|---|---|
| Comp. 5 | H1 | YD | CH4 | 555 |
| Comp. 6 | H1 | YD | CH1 | 555 |
| Comp. 7 | H1 | YD | CH2 | 553 |

None of the organic EL devices of Comparative Examples 5 to 7 emitted blue light.

Example 12

An organic EL device of Example 12 was prepared in the same manner as the organic EL device of Example 11 except that the compound H1 in the emitting layer of Example 11 was replaced with the compound H2.

A device arrangement of the organic EL device of Example 12 is roughly shown as follows.

ITO(130)/HI(5)/HT1(80)/HT2(10)/mCP(5)/CH4: H2: BD (25, 24%, 1%)/HB(5)/ET(20)/LiF(1)/Al(80)

Evaluation of Organic EL Device(s)

The prepared organic EL device was evaluated in the same manner as described above. Table 10 shows the evaluation results.

TABLE 10

|  | First Compound | Second Compound | Third Compound | Voltage [V] | CIEx | CIEy | $\lambda_p$ [nm] | LT50 [hrs] |
|---|---|---|---|---|---|---|---|---|
| Ex. 12 | H2 | BD | CH4 | 3.2 | 0.194 | 0.229 | 453 | 16 |

The organic EL device of Example 12 emitted blue light and had a long life as compared with the organic EL devices of Comparative Examples 1 to 4.

Comparative Example 8

An organic EL device of Comparative Example 8 was prepared in the same manner as the organic EL device of Example 12 except that the compound BD in the emitting layer of Example 12 was replaced with the compound YD.

A device arrangement of the organic EL device of Comparative Example 8 is roughly shown as follows.

ITO(130)/HI(5)/HT1(80)/HT2(10)/mCP(5)/CH4: H2: YD (25, 24%, 1%)/HB(5)/ET(20)/LiF(1)/Al(80)

Comparative Example 9

An organic EL device of Comparative Example 9 was prepared in the same manner as the organic EL device of Comparative Example 8 except that the compound CH4 in the emitting layer of Comparative Example 8 was replaced with the compound CH1.

A device arrangement of the organic EL device of Comparative Example 9 is roughly shown as follows.

ITO(130)/HI(5)/HT1(80)/HT2(10)/mCP(5)/CH1: H2: YD (25, 24%, 1%)/HB(5)/ET(20)/LiF(1)/Al(80)

Comparative Example 10

An organic EL device of Comparative Example 10 was prepared in the same manner as the organic EL device of Comparative Example 8 except that the compound CH4 in the emitting layer of Comparative Example 8 was replaced with the compound CH2.

A device arrangement of the organic EL device of Comparative Example 10 is roughly shown as follows.

ITO(130)/HI(5)/HT1(80)/HT2(10)/mCP(5)/CH2: H2: YD (25, 24%, 1%)/HB(5)/ET(20)/LiF(1)/Al(80)

Evaluation of Organic EL Device(s)

A main peak wavelength $\lambda_p$ of each of the prepared organic EL devices was evaluated in the same manner as described above. Table 11 shows the evaluation results.

TABLE 11

|  | First Compound | Second Compound | Third Compound | $\lambda_p$ [nm] |
|---|---|---|---|---|
| Comp. 8 | H2 | YD | CH4 | 555 |
| Comp. 9 | H2 | YD | CH1 | 553 |
| Comp. 10 | H2 | YD | CH2 | 554 |

None of the organic EL devices of Comparative Examples 8 to 10 emitted blue light.

Example 13

An organic EL device of Example 13 was prepared in the same manner as the organic EL device of Example 11 except that the concentration of the compound BD was set at 1 mass %, the concentration of the compound H1 was set at 49 mass % and the concentration of the compound CH4 was set at 50 mass % in the emitting layer of Example 11.

A device arrangement of the organic EL device of Example 13 is roughly shown as follows.

ITO(130)/HI(5)/HT1(80)/HT2(10)/mCP(5)/CH4: H1: BD (25, 49%, 1%)/HB(5)/ET(20)/LiF(1)/Al(80)

Evaluation of Organic EL Device(s)

The prepared organic EL device was evaluated in the same manner as described above. Table 12 shows the evaluation results.

TABLE 12

|  | First Compound | Second Compound | Third Compound | Voltage [V] | CIEx | CIEy | $\lambda_p$ [nm] | LT50 [hrs] |
|---|---|---|---|---|---|---|---|---|
| Ex. 13 | H1 | BD | CH4 | 2.9 | 0.172 | 0.208 | 453 | 8 |

The organic EL device of Example 13 emitted blue light and had a long life as compared with the organic EL devices of Comparative Examples 1 to 4.

Comparative Example 11

An organic EL device of Comparative Example 11 was prepared in the same manner as the organic EL device of Example 13 except that the compound BD in the emitting layer of Example 13 was replaced with the compound YD.

A device arrangement of the organic EL device of Comparative Example 11 is roughly shown as follows.

ITO(130)/HI(5)/HT1(80)/HT2(10)/mCP(5)/CH4: H1: YD (25, 49%, 1%)/HB(5)/ET(20)/LiF(1)/Al(80)

Comparative Example 12

An organic EL device of Comparative Example 12 was prepared in the same manner as the organic EL device of Comparative Example 11 except that the compound CH4 in the emitting layer of Comparative Example 11 was replaced with the compound CH1.

A device arrangement of the organic EL device of Comparative Example 12 is roughly shown as follows.

ITO(130)/HI(5)/HT1(80)/HT2(10)/mCP(5)/CH1: H1: YD (25, 49%, 1%)/HB(5)/ET(20)/LiF(1)/Al(80)

Comparative Example 13

An organic EL device of Comparative Example 13 was prepared in the same manner as the organic EL device of Comparative Example 11 except that the compound CH4 in the emitting layer of Comparative Example 11 was replaced with the compound CH2.

A device arrangement of the organic EL device of Comparative Example 13 is roughly shown as follows.

ITO(130)/HI(5)/HT1(80)/HT2(10)/mCP(5)/CH2: H1: YD (25, 49%, 1%)/HB(5)/ET(20)/LiF(1)/Al(80)
Evaluation of Organic EL Device(s)

A main peak wavelength $\lambda_p$ of each of the prepared organic EL devices was evaluated in the same manner as described above. Table 13 shows the evaluation results.

TABLE 13

|  | First Compound | Second Compound | Third Compound | $\lambda_p$ [nm] |
|---|---|---|---|---|
| Comp. 11 | H1 | YD | CH4 | 553 |
| Comp. 12 | H1 | YD | CH1 | 556 |
| Comp. 13 | H1 | YD | CH2 | 555 |

None of the organic EL devices of Comparative Examples 11 to 13 emitted blue light.

Example 14

An organic EL device of Example 14 was prepared in the same manner as the organic EL device of Example 13 except that the compound H1 in the emitting layer of Example 13 was replaced with the compound H2.

A device arrangement of the organic EL device of Example 14 is roughly shown as follows.

ITO(130)/HI(5)/HT1(80)/HT2(10)/mCP(5)/CH4: H2: BD (25, 49%, 1%)/HB(5)/ET(20)/LiF(1)/Al(80)
Evaluation of Organic EL Device(s)

The prepared organic EL device was evaluated in the same manner as described above. Table 14 shows the evaluation results.

The organic EL device of Example 14 emitted blue light and had a long life as compared with the organic EL devices of Comparative Examples 1 to 4.

Comparative Example 14

An organic EL device of Comparative Example 14 was prepared in the same manner as the organic EL device of Example 14 except that the compound BD in the emitting layer of Example 14 was replaced with the compound YD.

A device arrangement of the organic EL device of Comparative Example 14 is roughly shown as follows.

ITO(130)/HI(5)/HT1(80)/HT2(10)/mCP(5)/CH4: H2: YD (25, 49%, 1%)/HB(5)/ET(20)/LiF(1)/Al(80)

Comparative Example 15

An organic EL device of Comparative Example 15 was prepared in the same manner as the organic EL device of Comparative Example 14 except that the compound CH4 in the emitting layer of Comparative Example 14 was replaced with the compound CH1.

A device arrangement of the organic EL device of Comparative Example 15 is roughly shown as follows.

ITO(130)/HI(5)/HT1(80)/HT2(10)/mCP(5)/CH1: H2: YD (25, 49%, 1%)/HB(5)/ET(20)/LiF(1)/Al(80)

Comparative Example 16

An organic EL device of Comparative Example 16 was prepared in the same manner as the organic EL device of Comparative Example 14 except that the compound CH4 in the emitting layer of Comparative Example 14 was replaced with the compound CH2.

A device arrangement of the organic EL device of Comparative Example 16 is roughly shown as follows.

ITO(130)/HI(5)/HT1(80)/HT2(10)/mCP(5)/CH2: H2: YD (25, 49%, 1%)/HB(5)/ET(20)/LiF(1)/Al(80)

A main peak wavelength $\lambda_p$ of each of the prepared organic EL devices was evaluated in the same manner as described above. Table 15 shows the evaluation results.

TABLE 15

|  | First Compound | Second Compound | Third Compound | $\lambda_p$ [nm] |
|---|---|---|---|---|
| Comp. 14 | H2 | YD | CH4 | 553 |
| Comp. 15 | H2 | YD | CH1 | 555 |
| Comp. 16 | H2 | YD | CH2 | 555 |

TABLE 14

|  | First Compound | Second Compound | Third Compound | Voltage [V] | CIEx | CIEy | $\lambda_p$ [nm] | LT50 [hrs] |
|---|---|---|---|---|---|---|---|---|
| Ex. 14 | H2 | BD | CH4 | 3.3 | 0.205 | 0.253 | 453 | 28 |

None of the organic EL devices of Comparative Examples 14 to 16 emitted blue light.

The invention claimed is:

1. An organic electroluminescence device, comprising:
an anode;
an emitting layer; and
a cathode,
wherein:
the emitting layer comprises:
a delayed fluorescent first compound represented by formula (1):

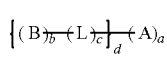
(1)

a fluorescent second compound; and
a third compound represented by a formula (3A):

Cz-Az   (3A);

the second compound emits light with a main peak wavelength ranging from 430 nm to 540 nm;
A is a group with a moiety selected from formula (a-1) to (a-7):

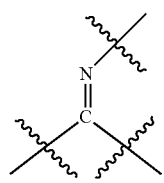
(a-1)

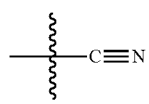
(a-2)

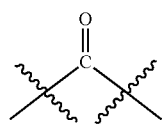
(a-3)

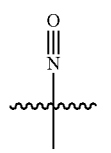
(a-4)

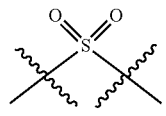
(a-5)

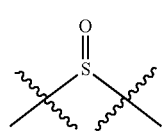
(a-6)

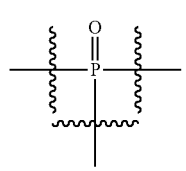
(a-7)

plural A moieties being the same or different and bonded together to form a saturated or unsaturated ring or forming no ring;
B is a group with a moiety selected from formula (b-1) to (b-6) below

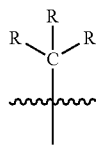
(b-1)

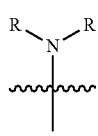
(b-2)

(b-3)

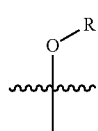

(b-4)

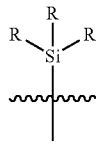
(b-5)

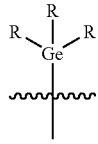
(b-6)

R are each independently a hydrogen atom or a substituent, R as a substituent being selected from the group consisting of a substituted or unsubstituted aromatic hydrocarbon group having 6 to 30 ring carbon atoms, a substituted or unsubstituted heterocyclic group having 5 to 30 ring atoms, and a substituted or unsubstituted alkyl group having 1 to 20 carbon atoms, plural R moieties being mutually the same or different and being bonded together to form a saturated or unsaturated ring or forming no ring;
plural B moieties being mutually the same or different and being bonded together to form a saturated or unsaturated ring or forming no ring;
a, b and d are each independently an integer of 1 to 5;
c is an integer of 0 to 5;
when c is 0, A and B are single-bonded or spiro-bonded to each other; and
when c is an integer of 1 to 5, L is a linking group selected from the group consisting of a substituted or unsubstituted aromatic hydrocarbon group having 6 to 30 ring carbon atoms and a substituted or unsubstituted heterocyclic group having 5 to 30 ring atoms, plural L being mutually the same or different and being bonded together to form a saturated or unsaturated ring or forming no ring;

Az is a cyclic structure selected from the group consisting of a substituted or unsubstituted pyrimidine ring and a substituted or unsubstituted triazine ring;

Cz is represented by a formula (a1), a formula (b1) or a formula (c) below:

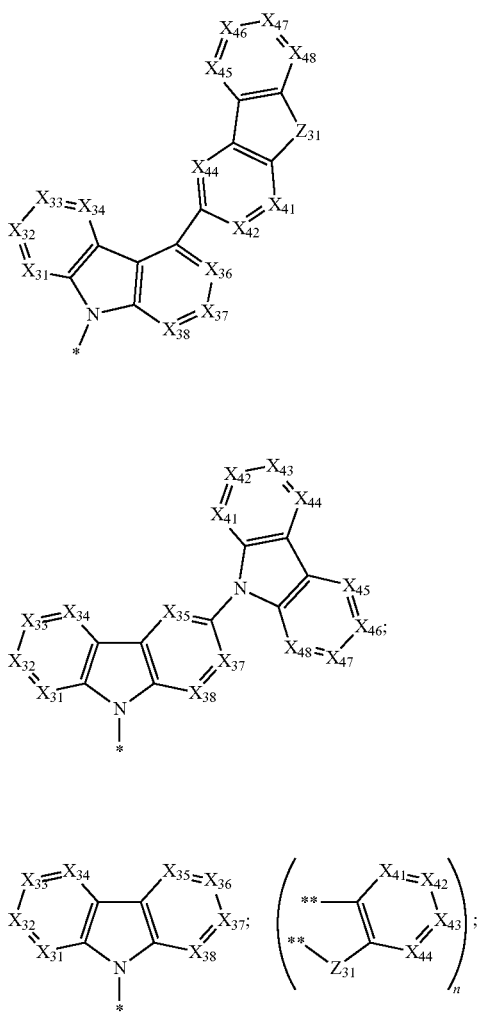

$X_{31}$ to $X_{38}$ and $X_{41}$ to $X_{48}$ are each independently C-Rx;

Rx are each independently a hydrogen atom;

$Z_{31}$ is an oxygen atom or a sulfur atom;

n is 1 or 2; and

* represents a bonding site to a carbon atom in the cyclic structure represented by Az, wherein the organic electroluminescence device emits blue light and has an LT50 (hrs) of at least 6.

2. The organic electroluminescence device according to claim 1, wherein:

Cz is represented by the formula (a1) or the formula (b1).

3. The organic electroluminescence device according to claim 1, wherein:

Cz is represented by the formula (c); and n is 1.

4. The organic electroluminescence device according to claim 3, wherein:

Cz is represented by a formula (c1):

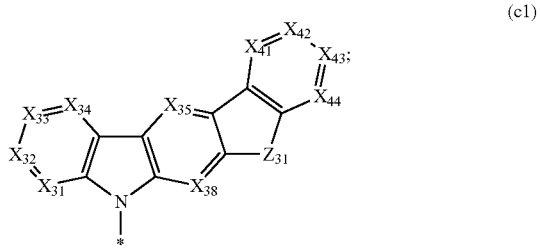

$X_{31}$ to $X_{35}$, $X_{38}$, and $X_{41}$ to $X_{44}$ are each independently C-Rx;

$R_x$ are each independently a hydrogen;

$Z_{31}$ is an oxygen atom or a sulfur atom; and

* represents a bonding site to a carbon atom in the cyclic structure represented by Az.

5. The organic electroluminescence device according to claim 1, wherein:

Az is a cyclic structure selected from the group consisting of a substituted pyrimidine ring and a substituted triazine ring; and a substituent for the pyrimidine ring and the triazine ring is a substituted or unsubstituted aryl group having 6 to 30 ring carbon atoms and a substituted or unsubstituted heteroaryl group having 5 to 30 ring atoms.

6. The organic electroluminescence device according to claim 1, wherein Az comprises a substituted or unsubstituted aryl group as a substituent, the substituent is selected from the group consisting of a substituted or unsubstituted phenyl group, a substituted or unsubstituted biphenyl group, a substituted or unsubstituted naphthyl group, a substituted or unsubstituted phenanthryl group, a substituted or unsubstituted terphenyl group, and a substituted or unsubstituted fluorenyl group.

7. The organic electroluminescence device according to claim 1, wherein Az comprises a substituted or unsubstituted aryl group as a substituent, the substituent is selected from the group consisting of a substituted or unsubstituted phenyl group, a substituted or unsubstituted biphenyl group, and a substituted or unsubstituted naphthyl group.

8. The organic electroluminescence device according to claim 1, wherein Az comprises a substituted or unsubstituted heteroaryl group as a substituent, the substituent is selected from the group consisting of a substituted or unsubstituted carbazolyl group, a substituted or unsubstituted dibenzofuranyl group, and a substituted or unsubstituted dibenzothienyl group.

9. The organic electroluminescence device according to claim 1, wherein the second compound emits light with a main peak wavelength ranging from 430 nm to 480 nm.

10. The organic electroluminescence device according to claim 1, wherein the second compound emits light with a main peak wavelength ranging from 445 nm to 480 nm.

11. The organic electroluminescence device according to claim 1, wherein a singlet energy $S_1(M1)$ of the first compound and a singlet energy $S_1(M2)$ of the second compound satisfy Numerical Expression 1:

$$S_1(M1) > S_1(M2) \qquad \text{(Numerical Expression 1).}$$

12. The organic electroluminescence device according to claim 1, wherein a singlet energy $S_1(M1)$ of the first compound and a singlet energy $S_1(M3)$ of the third compound satisfy Numerical Expression 2:

$$S_1(M3) > S_1(M1) \quad \text{(Numerical Expression 2)}$$

13. The organic electroluminescence device according to claim 1, further comprising:
    a hole transporting layer between the anode and the emitting layer.

14. The organic electroluminescence device according to claim 1, further comprising:
    an electron transporting layer between the cathode and the emitting layer.

15. An electronic device, comprising the organic electroluminescence device according to claim 1.

16. The organic electroluminescence device according to claim 1, wherein
    A in the formula (1) is a group with a moiety selected from the formula (a-1) to the formula (a-2);
    B in the formula (1) is a group with a moiety of the formula (b-2); and
    Cz in the formula (3A) is represented by the formula (c).

17. The organic electroluminescence device according to claim 1, wherein
    A in the formula (1) is a group with a moiety of the formula (a-2);
    B in the formula (1) is a group with a moiety of the formula (b-2); and
    Cz in the formula (3A) is represented by the formula (c).

18. The organic electroluminescence device according to claim 16, wherein
    A in the formula (1) is a group with a moiety of formula (a-2), and
    Cz in the formula (3A) is represented by a formula (c1):

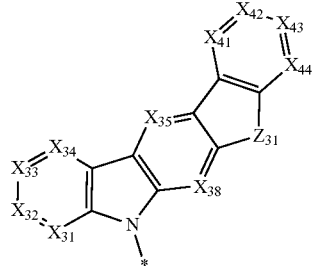

(c1)

$X_{31}$ to $X_{35}$, $X_{38}$, and $X_{41}$ to $X_{44}$ are each independently C-Rx;
Rx are each independently a hydrogen atom;
$Z_{31}$ is an oxygen atom or a sulfur atom; and
* represents a bonding site to a carbon atom in the cyclic structure represented by Az.

19. The organic electroluminescence device according to claim 18, wherein
    a substituent(s) bonded to L in the formula (1) is a heteroaryl group(s) derived from any one of moieties represented by a formula (XY-1) to (XY-6);

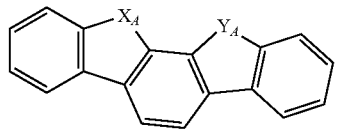

(XY-1)

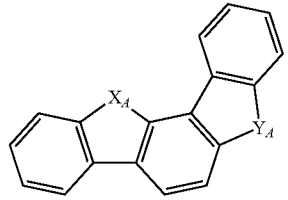

(XY-2)

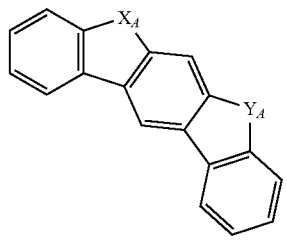

(XY-3)

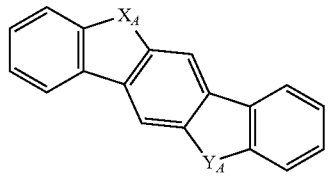

(XY-4)

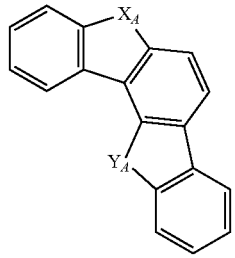

(XY-5)

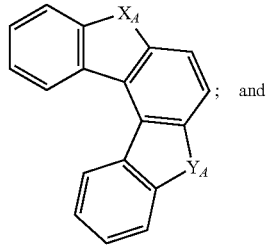

(XY-6)

; and $X_A$ and $Y_A$ are each independently a hetero atom.

20. The organic electroluminescence device according to claim 1, which has an LT50 (hrs) of 6 to 24.

* * * * *